United States Patent
Kuwata et al.

(10) Patent No.: US 11,484,280 B2
(45) Date of Patent: Nov. 1, 2022

(54) RADIOGRAPHIC IMAGE CAPTURING SYSTEM

(71) Applicant: Konica Minolta, Inc., Tokyo (JP)

(72) Inventors: Masahiro Kuwata, Machida (JP); Hidetake Tezuka, Tachikawa (JP); Satoshi Komiya, Hino (JP); Nobuyuki Miyake, Yokohama (JP); Hiroyuki Nakagawa, Hino (JP); Ichirou Hamamoto, Fuchu (JP); Shintaro Muraoka, Hachioji (JP); Kazuhiko Katsushima, Hino (JP); Tomoyasu Yokoyama, Tsurugashima (JP); Akira Hiroshige, Kokubunji (JP); Takanori Kakigi, Kodaira (JP); Tomoya Ogawa, Hachioji (JP); Tetsu Hosoki, Konagei (JP); Tomonori Gido, Kawasaki (JP); Makoto Sumi, Tokorozawa (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 17/108,392

(22) Filed: Dec. 1, 2020

(65) Prior Publication Data

US 2021/0077051 A1    Mar. 18, 2021

Related U.S. Application Data

(62) Division of application No. 16/011,687, filed on Jun. 19, 2018, now Pat. No. 10,881,370.

(30) Foreign Application Priority Data

Jun. 22, 2017    (JP) .............................. JP2017-122570

(51) Int. Cl.
*A61B 6/00*        (2006.01)
*G16H 30/20*    (2018.01)
(Continued)

(52) U.S. Cl.
CPC ............ *A61B 6/5205* (2013.01); *A61B 6/486* (2013.01); *A61B 6/5217* (2013.01); *A61B 6/54* (2013.01);
(Continued)

(58) Field of Classification Search
CPC ..... A61B 6/5205; A61B 6/486; A61B 6/5217; A61B 6/54; A61B 6/56; A61B 6/563;
(Continued)

(56) References Cited

U.S. PATENT DOCUMENTS 6,413,217 B1 * 7/2002 Mo ..................... G01S 7/52034
                                                                        600/440
7,549,961 B1 * 6/2009 Hwang ................ H04N 19/162
                                                                        600/440
(Continued)

FOREIGN PATENT DOCUMENTS

CN        103957800 A        7/2014
CN        105073007 A        11/2015
(Continued)

OTHER PUBLICATIONS

Extended European Search Report issued in corresponding EP Application 18178324.2, dated Nov. 12, 2018.
(Continued)

*Primary Examiner* — Blake C Riddick
(74) *Attorney, Agent, or Firm* — BakerHostetler

(57) ABSTRACT

A radiographic image capturing system is described. If a hardware processor determines that an image processor and an image analyzing unit are capable of sharing image data via an identical memory, the image processor stores image data in the memory and the image analyzing unit analyzes the image data with reference to the memory. If the hardware processor determines that the image processor and the image analyzing unit can send and receive the data via a wired
(Continued)

network, the image processor transfers the data to the image analyzing unit, and the image analyzing unit analyzes the data. If the hardware processor determines that the image processor and the image analyzing unit can send and receive the data via a wireless network, the image processor compresses the data or decimates partial data and transfers the data to the image analyzing unit, and the image analyzing unit decompresses and analyzes the data.

11 Claims, 31 Drawing Sheets

(51) Int. Cl.
*G06T 7/00* (2017.01)
*G16H 50/20* (2018.01)
*G16H 30/40* (2018.01)
*G16H 40/60* (2018.01)
*H04L 69/04* (2022.01)
*H03M 7/30* (2006.01)
*H04N 19/00* (2014.01)
*H04L 67/12* (2022.01)

(52) U.S. Cl.
CPC ............... *A61B 6/56* (2013.01); *A61B 6/563* (2013.01); *G06T 7/0012* (2013.01); *G16H 30/20* (2018.01); *G16H 30/40* (2018.01); *G16H 40/60* (2018.01); *G16H 50/20* (2018.01); *G06T 2207/10116* (2013.01); *H03M 7/30* (2013.01); *H04L 67/12* (2013.01); *H04L 69/04* (2013.01); *H04N 19/00* (2013.01)

(58) Field of Classification Search
CPC ........ G16H 50/20; G16H 40/60; G16H 30/20; G16H 30/40; G06T 7/0012; G06T 2207/10116; H03M 7/30; H04L 67/12; H04L 69/04
See application file for complete search history.

(56) References Cited

U.S. PATENT DOCUMENTS

| | | | |
|---|---|---|---|
| 2006/0017028 A1 | 1/2006 | Ohara et al. | |
| 2006/0257031 A1 | 11/2006 | Abramoff et al. | |
| 2007/0239001 A1* | 10/2007 | Mehi ................... | G10K 11/341 600/437 |
| 2009/0248036 A1* | 10/2009 | Hoffman ............... | A61B 34/30 606/130 |
| 2010/0246925 A1* | 9/2010 | Nagatsuka ........... | A61B 5/1135 382/132 |
| 2011/0158385 A1 | 6/2011 | Nakatsugawa et al. | |
| 2011/0170669 A1 | 7/2011 | Nakatsugawa et al. | |
| 2011/0182406 A1 | 7/2011 | Nelson et al. | |
| 2012/0181437 A1 | 7/2012 | Nelson et al. | |
| 2013/0051704 A1 | 2/2013 | Koishi | |
| 2014/0276056 A1 | 9/2014 | Ohta et al. | |
| 2015/0029821 A1* | 1/2015 | Miyaki ............... | G01S 7/52017 367/7 |
| 2015/0142461 A1 | 5/2015 | Darty et al. | |
| 2015/0363926 A1 | 12/2015 | Enomoto | |
| 2016/0074015 A1* | 3/2016 | Eda ..................... | A61B 8/5269 600/443 |
| 2016/0228087 A1 | 8/2016 | Oda et al. | |
| 2018/0097944 A1* | 4/2018 | Otake .................. | G06F 3/1203 |

FOREIGN PATENT DOCUMENTS

| | | |
|---|---|---|
| JP | 2012-045179 A | 3/2012 |
| JP | 2014-128687 A | 7/2014 |
| JP | 2019-005073 A | 1/2019 |
| WO | WO 2013/047069 A1 | 4/2013 |
| WO | WO 2013/081042 A1 | 6/2013 |

OTHER PUBLICATIONS

European Patent Application No. 18178324.2; Office Action—94(3); dated Jun. 24, 2020; 7 pages.
China Patent Application No. 201810630679.0; Office Action; dated Jul. 12, 2021; 21 pages.
Japan Patent Application No. 2021-133773; Notice of Reasons for Refusal; dated Sep. 6, 2022; 8 pages.

* cited by examiner

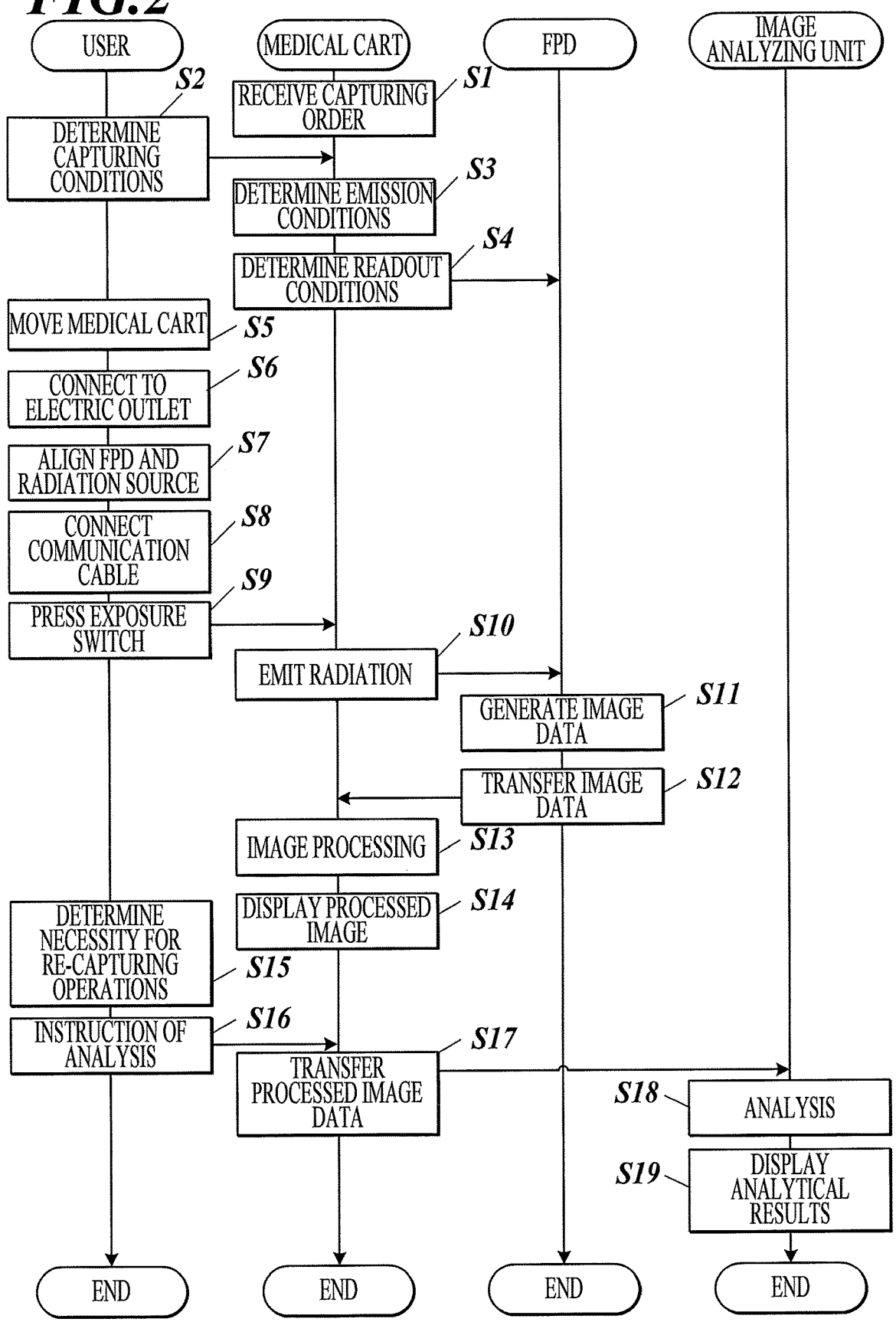

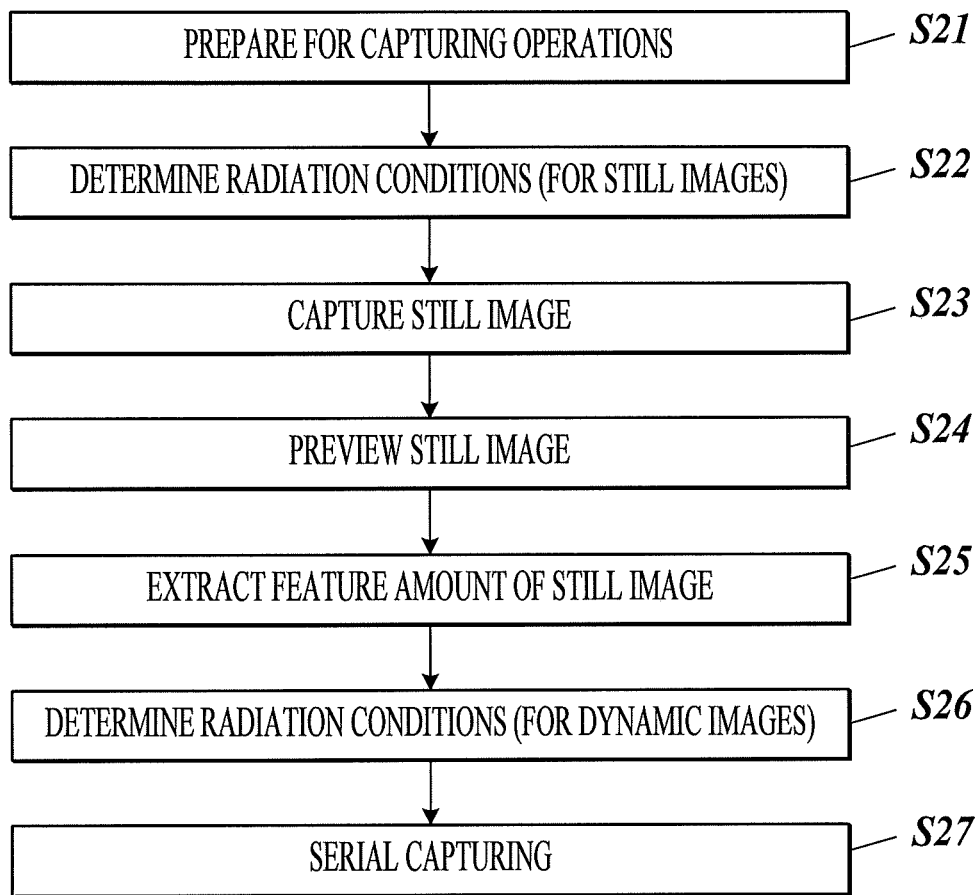
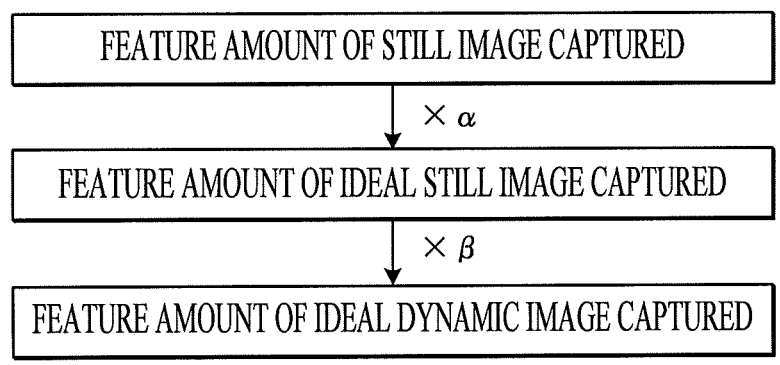

RADIOGRAPHIC IMAGE CAPTURING SYSTEM

The present U.S. Patent Application is a divisional application of U.S. patent application Ser. No. 16/011,687 filed Jun. 19, 2018, which claims priority to Japanese Patent Application No. 2017-122570 filed on Jun. 22, 2017, the entire disclosures of which are incorporated herein by reference in their entireties.

BACKGROUND

Technological Field

The present invention relates to a radiographic image capturing system.

Description of the Related Art

In recent years, portable radiographic capturing apparatuses (flat panel detectors (FPD)) have been used for capturing dynamic images of target portions of subjects for diagnosis purpose. The dynamic images refer to a series of images acquired through repeated capturing cycles several times per second with a radiographic capturing apparatus that can read and delete image data at a high rate. Continuous display of these multiple images facilitates recognition of a series of dynamic states of the target portion.

These images are analyzed to generate information on, for example, lung functions, such as ventilation and lung perfusion.

For example, Japanese Unexamined Patent Application Publication No. 2014-128687 discloses a dynamic image diagnosis supporting system which performs serial capturing operations of a breathing chest to acquire multiple frame images showing the dynamic state of the chest and analyzes these frame images to generate information on the bloodstream.

The system has a radiographic capturing apparatus and a capturing console that ate connected via a communication cable, and the capturing console and a diagnosis console that are connected via a communication network, such as a local area network (LAN). The capturing console is used to determine capturing conditions. The diagnosis console is used to analyze the images. Upon receipt of a series of dynamic frame images from the capturing console, the diagnosis console sums to analyze the frame images and displays the analytical results on a display.

In a system equipped with the capturing console and the diagnosis console shown in Japanese Unexamined Patent Application Publication No 2014-128687, the capturing console and the diagnosis console may be connected with a wired or wireless network. In general the wired network has a higher communication rate than the wireless network. The time to send image data to the diagnosis console varies, depending on a connection scheme. In particular, dynamic images have a data volume significantly greater than still images, resulting in a significant difference in transfer time. The traditional system has a significant variance in time from the capture of images to display of the analytical results, depending on a connection scheme between the capturing console and the diagnosis console, which adversely affects the usability.

SUMMARY

An object of the present invention, which has been made to overcome the disadvantages of the conventional techniques described above, is to provide: a radiographic image capturing system equipped with an image analyzing means that reduces a variance in time for a user to wait for the completion of the image analysis after capture of the image to enhance the usability.

To achieve at least one of the abovementioned objects, according to an aspect of the present invention, a radiographic image capturing system reflecting one aspect of the present invention includes, a radiographic capturing apparatus which captures radiographic images several times at a predetermined frame rate to generate multiple pieces of image data; a radiation emitting apparatus which emits continuous radiation rays or emits pulsed radiation rays toward the radiographic capturing apparatus; an image processor which processes the multiple pieces of image data generated at the radiographic capturing apparatus to generate multiple pieces of processed image data, an image analyzing unit which analyzes the multiple pieces of processed image data to generate diagnosis supporting information: and a hardware processor which determines a system configuration between the image processor and the image analyzing unit; wherein if the hardware processor determines that the image processor and the image analyzing unit are capable of sharing the image data via an identical memory, the image processor stores the multiple pieces of processed image data in the memory and the image analyzing unit analyzes the multiple pieces of processed image data with reference to the memory, if the hardware processor determines that the image processor and the image analyzing unit are capable of sending and receiving the image data via a wired network, the image processor transfers the multiple pieces of processed image data to the image analyzing unit over the wired network, and the image analyzing unit analyzes the transferred multiple pieces of processed image data, and if the hardware processor determines that the image processor and the image analyzing unit are capable of sending and receiving the image data via a wireless network, the image processor compresses the multiple pieces of processed image data into compressed image data or decimates partial processed image data of the multiple pieces of processed image data to generate decimated image data and transfers the compressed or decimated image data to the image analyzing unit via the wireless network, and the image analyzing unit decompresses and analyzes the transferred compressed image data or analyzes the transferred decimated image data.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

FIG. 2 is a ladder chart illustrating an inspection flow using the radiographic image capturing system according to the first embodiment.

FIG. 7 is a flow chart of the control process of the radiographic image capturing system according to Example 2 of the first to third embodiments.

FIG. 8 is another flow chart of the control process of the radiographic image capturing system according to Example 2 of the first to third embodiments.

DETAILED DESCRIPTION OF EMBODIMENTS

Hereinafter one or more embodiments of the present invention will be described with reference to the drawings. However, the scope of the invention is not limited to the disclosed embodiments.

First Embodiment

A first embodiment of the present invention will now be described with reference to the drawings.

Figure 1A:
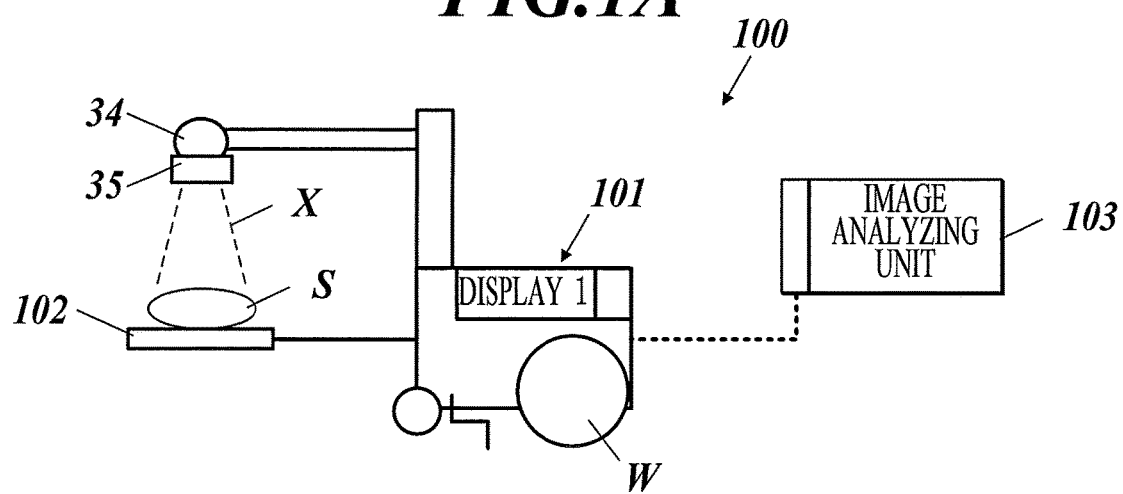
FIG. 1A is a side view of a radiographic image capturing system according to a first embodiment of the present invention.
Figure 1B:
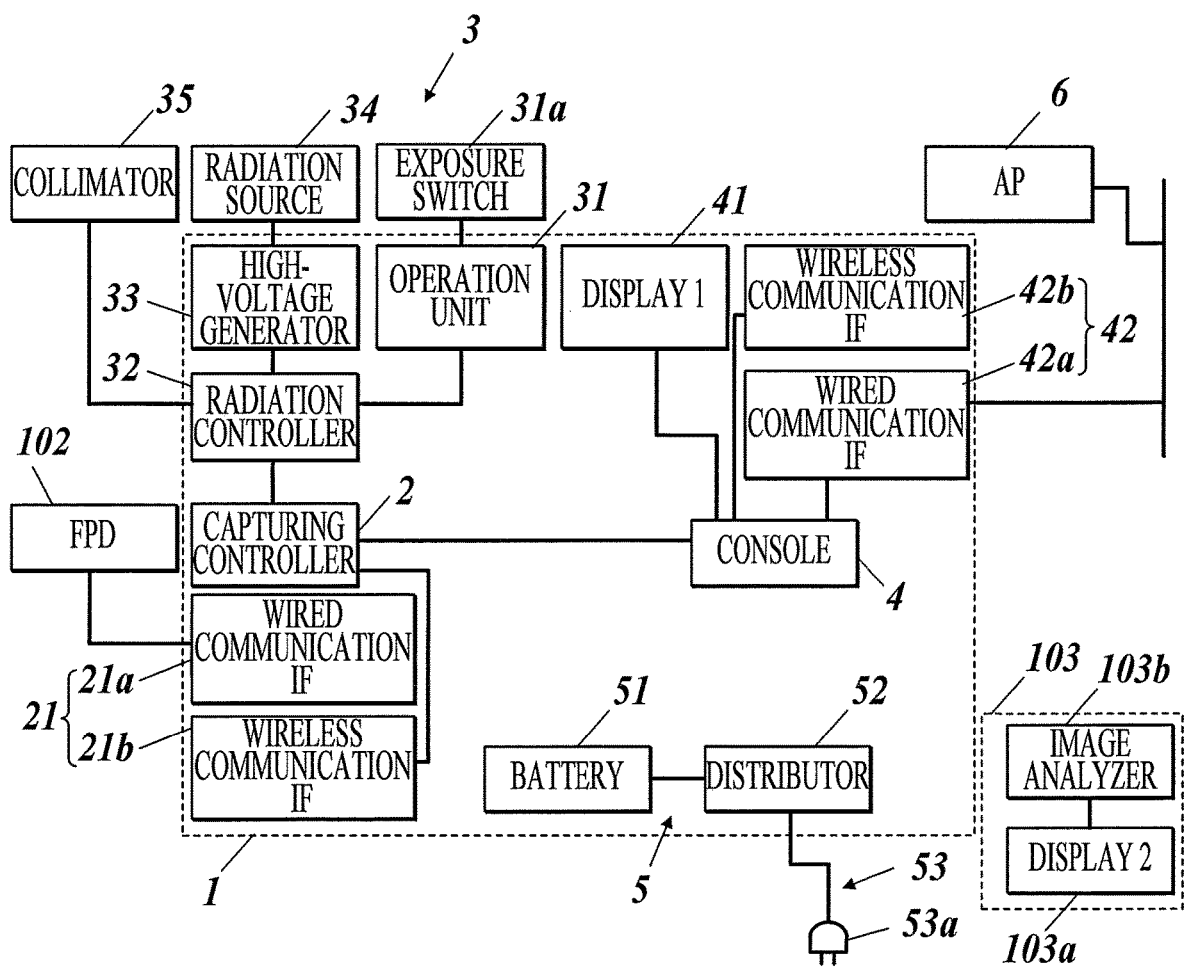
FIG. 1B is a block diagram illustrating the configuration of the radiographic image capturing system according to the first embodiment of the present invention.

A radiographic image capturing system 100 according to the first embodiment will now be outlined. FIG. 1A is a side view of the radiographic image capturing system 100 according to this embodiment. FIG. 1B is a block diagram illustrating the configuration of the radiographic image capturing system 100.

With reference to FIG. 1A, the radiographic image capturing system 100 according to this embodiment includes a body 101, one or more radiographic capturing apparatuses (flat panel detectors (FDP)s) 102, and an image analyzing apparatus 103 (image analyzing means).

The radiographic image capturing system 100 may be connected with a radiology information system (RIS) (not shown) or a picture archiving and communication system (PACS) (not shown) with a wired or wireless network.

The radiographic image capturing system 100 according to this embodiment enables rounds of subjects (or objects of shooting) having a walking difficulty to capture radiographic images. In detail, the body 101 includes wheels W and is a movable medical cart. The body 101 is hereinafter referred to as the medical cart 101

The radiographic image capturing system 100 according to this embodiment may be fixed in, for example, a radiation chamber of a hospital.

The medical cart 101 is designed to determine various capturing conditions, emit radiation rays to a subject (or the FPD 102), perform predetermined image processing on image data sent from the FPD 102, display images, and output image data to the image analyzing apparatus 103.

The medical cart 101 will be described below in detail.

The FPD 102 includes a substrate, a readout circuit, a controller, a communication unit, and a connector, although these components are not shown. The substrate includes radiation detecting elements and pixels disposed thereon in a two-dimensional array (matrix). The radiation detecting elements generate electric charges in proportion to the dose of radiation rays X incident thereon. The pixels include switching elements that accumulate and release electric charges. The readout circuit reads the amount of electric charges released from each pixel as a signal value. The controller generates image data from multiple signal values read from the readout circuit. The communication unit sends image data and various signals to the medical cart 101 via a wired or wireless network. The connector receives a cable connected to the medical cart 101.

The FPD 102 may include a scintillator. The scintillator in the FPD 102 converts incident radiation rays X into light with a different wavelength, such as visible light, and generates electric charges in proportion to the converted light (indirect type). Alternatively, the FPD 102 may generate electric charges directly from radiation rays X without the scintillator (direct type).

The FPD 102 is connected to the medical cart 101 with a communication cable to enable a wired communication between the FPD 102 and the medical cart 101. In detail, the FPD 102 receives various control signals from the medical cart 101 via the communication cable and sends generated image data to the medical cart 101.

The image analyzing apparatus 103 is a computer or dedicated control unit. With reference to FIG. 1B. the image analyzing apparatus 103 includes a second display 103a, an image analyzer 103b, a memory 103c, a communication unit 103d, and an operation unit 103e (see FIG. 17).

The image analyzing apparatus 103 is connected to the medical cart 101 with a wired or wireless network to allow the image analyzing apparatus 103 to send/receive various image data to/from the medical cart 101.

The image analyzing apparatus 103 performs image analysis on the received image data and displays the analytical results on the second display 103a or sends the analytical results to the medical cart 101 or PACS.

The "image analysis" refers to analysis of functional information included in the captured image data and generation of the analytical result data (diagnosis support information).

The radiographic image capturing system 100 according to this embodiment having the above mentioned configuration can perform serial capturing operations by emitting radiation (X-ray) to a subject in front of the FPD 102 from the medical cart 101.

The "serial capturing operation" according to this embodiment refers to acquisition of a series of images through repeated cycles, in the FPD 102, of accumulation of electric charges and readout of signal values in a short time in response to a single capturing operation (press of an exposure switch described below).

A series of images acquired through the serial capturing operations is hereinafter referred to as a "dynamic image" and each of images constituting the dynamic images is referred to as a "frame image".

The medical cart 101 of the radiographic image capturing system 100 will now be described in detail.

The medical cart 101 includes a housing 1 equipped with wheels W, a capturing controller 2, a radiation emitting apparatus 3, a console 4, and a power supply 5.

The capturing controller 2 includes a central processing unit (CPU) (not shown), a random access memory (RAM) (not shown), a memory (not shown), and a crystal oscillator (not shown).

The CPU in the capturing controller 2 leads OS programs and various application programs from the memory onto the RAM and controls the operations of various units of the medical cart 101 according to the read programs.

The memory of the capturing controller 2 includes a nonvolatile semiconductor memory or a hard disk containing various programs executed by the capturing controller 2 and parameters necessary to execute these programs. The memory can also contain data, such as processing results.

The communication unit 21 includes a wired communication interface 21a and a wireless interface 21b. The wired communication interface 21a enables a wired communication with the FPD 102 over a communication cable extending from the FPD 102 (hereinafter referred to as "wired communication IF"). The wireless interface 21b enables a wireless communication with the FPD 102 (hereinafter referred to as "wireless communication IF"). This configuration allows the connection scheme to be switched between wired and wireless networks in response to a control signal from the CPU.

The radiation emitting apparatus 3 includes an operation unit 31, a radiation controller 32, a high-voltage generator 33, a radiation source (tube) 34, and a collimator 35.

The operation unit 31 includes buttons and a touch panel which are operable by a user. The operation unit 31 detects a user operation (the type of a button pressed or the touched position of a finger or a touch pen) and outputs the detected information to the radiation controller 32 as operational information.

The operation unit 31 has an exposure switch 31a connected thereto to allow a user to instruct the emission of radiation rays X. The exposure switch 31a is a two-step switch.

The operation unit 31 detects which operation step is performed to the exposure switch 31a and outputs the detected information to the radiation controller 32 as exposure switch information.

The exposure switch 31a may lie connected to the medical cart 101 via a wired or wireless network to enable remote control. This configuration allows the user to control radiation exposure from a place remote from the radiation emitting apparatus 3 in the medical cart 101.

The radiation controller 32 can determine various capturing conditions based on operational information from the operation unit 31. The capturing conditions include subject conditions, such as the target site and physical constitution of the subject, and radiation conditions, such as the voltage and current of the X-ray tube, the irradiation time, and the product of the current and time.

Upon receipt of the exposure switch information, the radiation controller 32 sends control information to the high-voltage generator 33 to instruct it to start applying a voltage (emitting radiation rays).

Upon receipt of the control signal from the radiation controller 32, the high-voltage generator 33 applies a predetermined voltage suitable for the radiation conditions to the radiation source 34.

Capturing may be performed not in a radiation chamber having a function to prevent leakage of radiation rays but in a medical ward where a patient stays. In consideration of the situation, the radiation emitting apparatus 3 in the medical cart 101 may have a lower radiation output than that from the radiation emitting apparatus fixed in the radiation chamber during the capturing operation. In this case, the high-voltage generator 33 may operate at a lower power than that fixed in the radiation chamber.

The radiation source 34 includes, for example, a rotary anode (not shown) and a filament (not shown). In response to application of a voltage from the high-voltage generator, the filament emits electron beams in proportion to the applied voltage to the rotary anode. The rotary anode generates a dose of radiation rays X in proportion to the intensity of the electron beams.

In detail, the radiation source 34 continuously emits radiation rays in response to a continuous application of voltage from the high-voltage generator, while the radiation source 34 emits pulsed radiation rays in response to application of a pulsed voltage.

The radiation emitting apparatus according to this embodiment can handle any type of capturing operations, i.e., still-image capturing operations, serial capturing operations by continuous radiation, and serial capturing operations by pulsed radiation.

The collimator 35 is provided at a radiation port of the radiation source 34 (the path on the radiation rays X).

The collimator 35 has four shield blades and an adjuster mechanism (not shown). The shield blades are disposed, for example, above and below and on the right and left of the path on the radiation rays X such that a rectangular opening is formed. The adjuster mechanism moves the shielding blades. In response to a control signal from the radiation controller 32, the collimator 35 instructs the adjuster mechanism to shift the position of the shield blades to control the irradiation field.

The console 4 is a computer or dedicated control unit and includes a controller (not shown), a memory (not shown) and an operator (not shown).

Upon receipt of image data from the FPD 102, the console 4 performs image processing, such as predetermined correction, on the image data automatically or based on user's predetermined operations to generate a processed image.

The "image processing" refers to adjustment of the visibility of an image through modification of the brightness or density of the image.

The console 4 determines the system configuration, in detail, a connection scheme between the console itself and the image analyzing apparatus 103.

Based on the determined system configuration, the console 4 can compress the processed image data to generate compressed image data or decimate partial frame image data of the processed image data to generate decimated image data.

The console 4 can send at least one of the processed image data, the compressed image data, and the decimated image data to the image analyzing apparatus 103 via the communication unit 42.

The display 41 includes a monitor, such as a liquid crystal display (LCD) or a cathode ray tube (CRT), to display capturing order information or a captured image in accordance with display signals input from the controller of the console 4 or from the capturing controller 2 via the console 4.

The display 41 displays an image based on processed image data.

The display 41 may be connected to the medical cart 101 via a wired or wireless network to enable remote display. This configuration allows the user to confirm various pieces of information from a place remote from the radiation emitting apparatus 3 in the medical cart 101.

Alternatively, a sub-monitor which is distinct from the display 41, may be connected via a wired or wireless network.

The communication unit 42 includes the wired communication IF 42a and the wireless communication IF 42b. The wired communication IF 42a is in wired communication with the image analyzing apparatus 103 through a communication cable extending from the image analyzing apparatus 103. The wireless communication IF 42b is in wireless communication with the image analyzing apparatus 103. The communication unit 42 allows the connection scheme to be switched between wired and wireless networks based on control signals sent front the controller.

The power supply 5 includes a battery (built-in power supply) 51, a distributor 52, and a power cable 53.

The battery 51 can feed power stored therein to the distributor 52 and store power fed from the distributor 52.

The distributor 52 has a power cable 53 provided with a plug 53a at the tip. The distributor 52 can receive external power via the plug 53a inserted into a near-by electric outlet.

The distributor 52 distributes power supplied from the battery 51 or the external source to various units of the medical cart 101.

Figure 11:
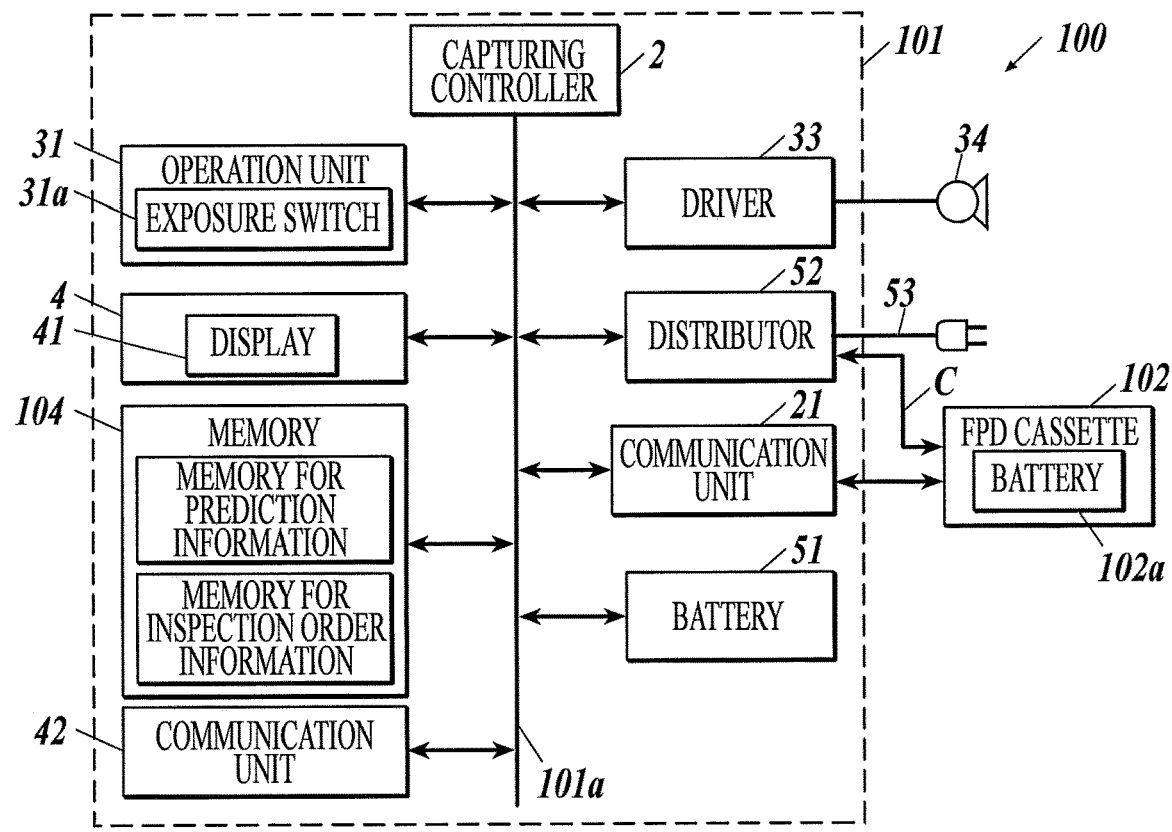
FIG. 11 is a block diagram illustrating a configuration of a radiographic image capturing system according to Example 7 of the first to third embodiments.

Wiring for distributing the power from the distributor 52 to various units is omitted in FIGS. 1B and 3B (described below). However, the distributor 52 and various units are electrically connected via, for example, a line 101a as shown in FIG. 11.

The distributor 52 can accept voltages of, for example, 100V and 200V and frequencies of 50 Hz and 60 Hz. The distributor 52 can thereby receive power from either domestic or commercial power sources.

The voltages and frequencies are exemplary ones in use of the radiographic image capturing system 100 in Japan. The radiographic image capturing system 100 can be used in other countries or regions after the specifications of the distributor 52 are modified.

An inspection flow using the radiographic image capturing system 100 will now be described. FIG. 2 is a ladder chart illustrating the inspection flow using the radiographic image capturing system according to the present invention.

In the initial preparation for the capturing operation, the console 4 receives a capturing order from, for example, RIS via an access point 6 (Step S1).

A user determines various capturing conditions based on the received capturing order (Step S2). In detail, the user selects appropriate capturing conditions or enters numeric values through the operation of the operation unit 31. In the case of serial capturing operations, the frame rate, the capturing time, and the number of frames are also determined.

After the determination of the capturing conditions, the capturing controller 2 of the medical cart 101 determines the radiation conditions of the high-voltage generator 33, the capturing range of the collimator 35, and the type of a filter based on the input to the operation unit 31 in response to an instruction from the console 4 (Step S3). The capturing controller 2 then determines readout conditions for the FPD 102 (the scope of binning) (Step S4).

Alternatively, the console 4 may automatically determine various capturing conditions without user intervention.

In the ease of a radiographic image capturing system 100 equipped with two or more FPDs 102, any one of them is selected.

After the completion of the preparative operation, the user starts a positioning operation.

In the positioning operation, the user moves the medical cart 101 to a place closer to a subject (Step S5). The user inserts the plug 53a of the power cable 53 into an electric outlet to enable power supply from the outside (Step S6). The power supply 5 of the medical cart 101, which can receive power from domestic and commercial power sources as described above, can receive power at an operation room, an intensive-care unit, a medical ward, or the house of a home-care patient.

The user then aligns the FPD 102, the radiation source 34, and the subject at positions suitable for the capturing operation (Step S7). For example, the user puts the FPD 102 between a target site of the subject lying on a bed and the bed, or puts the FPD 102 into contact with a side of the subject such that the radiation source 34 faces the FPD 102 via the subject.

The user then connects a communication cable between the medical cart and the FPD 102 (Step S8). The communication cable is preferably covered with a cover to prevent detachment.

Alternatively, Step S8 (cable connection) may be performed before Step S7 (positioning of the FPD 102).

Alternatively, the communication cable may be integrated with the cover.

As described above, in the case where the exposure switch 31a or the display 41 of the console 4 is connected to the housing 1 of the medical cart 101 with a wired or wireless network such that the exposure switch 31a or the display 41 can be placed separately from the housing 1, the device may be placed distant from the housing 1.

At any timing up to this step, the user connects the medical cart 101 to the image analyzing apparatus 103 via a wireless network.

Instead of the direct connection of the medical cart 101 to the image analyzing apparatus 103 via a wireless network, the user may connect the access point 6 (see FIG. 1B) to the wireless communication IF 42b of the medical cart 101 via a wireless network and then connect the access point 6 to the image analyzing apparatus 103 via a wired network.

The image analyzing apparatus 103 according to this embodiment, which is connected to the medical cart 101 via a wireless network, may be an image analyzer in a remote computer. The external image analyzer may be, for example, installed in a computer in the server room of a hospital or placed m analyzing operator's room in a hospital or in a work room adjacent to a radiation chamber. Alternatively, an external image analyzing unit may be placed in a server room having a connection to an external network.

In this case, image data should be sent/received to/from the medical cart 101 over a P2P network. The P2P network allows transfer of image data at a higher rate than that on a network having a large number of computers connected thereto.

After the positioning is completed, the user starts the capturing operation.

In the capturing operation, user presses the exposure switch 31a (Step S9). The capturing controller 2 adjusts the timing between the high-voltage generator 33 and the FPD 102 before the capturing operation. In detail, in response to the press of the first step of the exposure switch 31a, the capturing controller 2 instructs the radiation source 34 to prepare for operations (activation of the rotor in the case of a rotary anode) and puts the FPD 102 in a capture-ready state.

The user determines whether the imitation emitting apparatus 3 and the FPD 102 are ready for the capturing operation. In the case of a medical cart 101 is provided with a state display section that indicates whether the radiation emitting apparatus 3 and the FPD 102 are ready for the capturing operation, the user checks for the state display section. This configuration allows the user to determine the capture-ready state at a glance without checking displays also showing various other information, such as the display 41 of the console 4, thus facilitating checking of the capture-ready state.

After the capture-ready state is confirmed, the user presses the second step of the exposure switch. The radiation controller 32 instructs the high-voltage generator 33 to emit radiation rays continuously for a predetermined time or emit pulsed radiation rays at a predetermined cycle (Step S10). The capturing controller 2 instructs the FPD 102 to repeat a cycle of accumulation of electric charges and readout of image data at a frame rate predetermined for the FPD 102 (to generate image data)(Step S11).

After the elapse of the predetermined capturing time, the capturing controller 2 instructs the high-voltage generator 33 to stop the emission of radiation rays and the FPD 102 to stop the readout of the image data. In response to the release of the exposure switch during the capturing operation, the capturing controller 2 also instructs the high-voltage generator 33 to stop the emission and the FPD 102 to stop the readout.

After the capturing operation is completed, the radiographic image capturing system 100 starts to verify the captured images.

The FPD 102 transfers the generated dynamic image data to the console 4 via the communication unit 21 of the medical cart. 101 (Step S12). The console 4 sequentially processes multiple pieces of frame image data constituting the transferred dynamic image data to generate processed dynamic image data (Step S13).

The console 4 displays dynamic images based on the processed dynamic image data on the display 41 (Step S14). During the capturing operation, a simplified image processing may be employed for prompted display of dynamic images.

After the process of all frame image data following the capturing operation, the user can verify the dynamic images on the display 41. In response to user's requests, the dynamic images may be displayed at the same frame rate as that during the capturing operation, continuously with mouse operations, or at a higher rate than the actual rate.

The user verifies the dynamic images displayed on the display 41 to determine whether re-capturing is necessary (Step S15).

Serial capturing operations at a low frame rate may generate discontinuous dynamic images. Such discontinuous dynamic images cannot satisfactorily express the actual continuous movement, not enabling the user to determine whether such dynamic images are suitable for diagnosis.

To cope with this problem, an interpolated frame image is generated based on the preceding and succeeding frame images and inserted between the preceding and succeeding frame images during image processing at the console 4. Such interpolation allows dynamic images that move more smoothly and continuously to be generated and displayed. For example, in the case of serial capturing operations at a frame rate of 7.5 Hz, three interpolated frame images are inserted between each pair of the preceding and succeeding frame images to generate dynamic images equivalent to those captured at a frame rate of 30 Hz. Such interpolated frame images can be acquired readily by linearly interpolating the pixel densities of the two original frame images.

Such interpolation facilitates the user to determine whether generated dynamic images are suitable for diagnosis.

If the user determines that no re-capturing operation is required (the capturing operation is successful) based on the results of image verification, the user instructs the console 4 to start image analysis (Step S16). In response to this instruction, the radiographic image capturing system 100 starts image analysis.

The console 4 transfers the processed dynamic image data to the image analyzing apparatus 103 via the wireless communication IF 42b of the communication unit 42 (Step S17).

The image analyzing apparatus 103 analyzes the processed dynamic image data that has been transferred for any functional information and performs the analysis to generate analytical result data (diagnosis support information) (Step S18).

In the analysis, the image analyzing apparatus 103 does not use the interpolated images generated at the console 4 during the image processing.

After the analysis is completed, the image analyzing apparatus 103 displays an analyzed image on a display 103a based on the analytical data (Step S19). If the radiographic image capturing system 100 is used in, for example, an operation room, the analyzed image may be displayed on a large monitor installed on a wall in the room.

Medical doctors look at the analyzed image appearing on the display 103a for diagnosis.

A series of inspection processes is thereby completed.

In the above inspection processes, the medical cart 101 is connected to the image analyzing apparatus 103 via a wireless network. Alternatively, the medical cart 101 may be connected to the image analyzing apparatus 103 via a wired network (by plugging a communication cable extending from the image analyzing apparatus 103 into the connector of the wired communication IF 42a). The radiographic image capturing system 100 according to this embodiment sends image data to the image analyzing apparatus 103 via the communication cable.

In the case of detachment of the communication cable during the preparative operation, the capturing operation, or the image transfer after the capturing operation in the above verification process, a connection detecting function for the wired connection may detect the detachment of the communication cable.

In response to the detection of detachment of the communication cable by the FPD 102, the FPD 102 may send a signal indicating the detachment of the communication cable via a wireless network to the wireless communication IF 21b of the medical cart 101.

Such a connection detecting function for the communication cable may detect detachment, if any, and send a notice. Alternatively, such a connection detecting function may confirm the connection state by continuously monitoring the connection at predetermined intervals during the preparative operation, the capturing operation, or the image transfer after the capturing operation.

In response to the detection of an unexpected disconnection of the wired network during the preparative operation, the capturing operation, or the image transfer after the capturing, the console 4 displays the notice of the disconnection on the display 41 and suspends the operation sequence performed during the preparative operation, the capturing operation, or during the image transfer after the capturing operation.

The user notices the disconnection of the wired network, reconnects the communication cable to restore the connection, and resumes the operation sequence from where it was left off during the preparative operation, during the capturing operation, or during the image transfer after the capturing operation due to the disconnected wired network. Alternatively, the user may return to a re-executable point from the point where the operation sequence was left off during the preparative operation, during the capturing operation, or during the image transfer after the capturing operation due to the disconnected wired network, delete all the data, including for the suspended sequence, back to the re-executable point, and retries the operation from the re-executable point.

The radiographic image capturing system 100, which involves dynamic state analysis, receives original dynamic image data in the image analyzing apparatus 103 and analyzes analytical result data, which is also dynamic images in many cases. Such dynamic images have a data volume significantly greater than still images, resulting in a longer time to transfer and analyze the data.

During rounds to medical wards using the medical cart 101, the user may be requested to verify the results of the dynamic state analysis of a subject immediately after the capturing operation. To meet such a request, the time to wait for the analytical results to be displayed, including the time to transfer and analyze the data, should be reduced.

The image analyzing apparatus 103 according to this embodiment is provided separately from the medical cart 101. This configuration provides a communication environment with adequate network bandwidth. Such a communication environment can reduce time to wait for the analytical results to be confirmed immediately after the capturing operation during rounds to medical wards.

The radiographic image capturing system 100 also enables stable permanent connection and selection of a large and high-performance stationary PC. This allows dynamic state analysis normally conducted in a hospital to be conducted on a large external server.

Second Embodiment

The second embodiment of the present invention will now be described.

Only differences from the first embodiment will now be described (The configurations, variations and operations omitted are basically the same as those of the first embodiment).

Figure 3A:
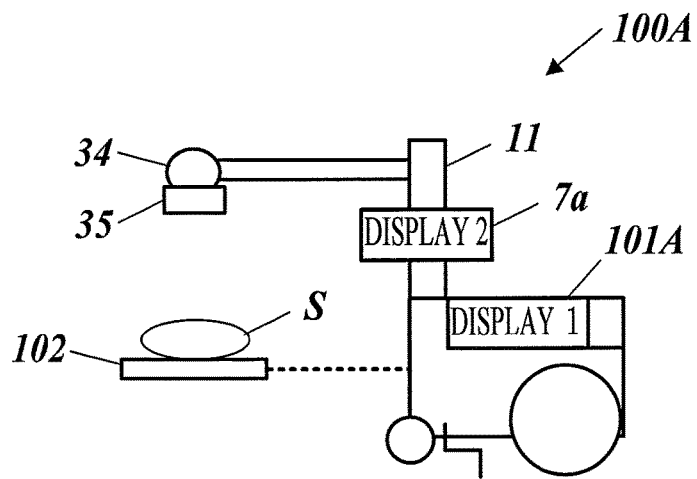
FIG. 3A is a side view of a radiographic image capturing system according to a second embodiment of the present invention.
Figure 3B:
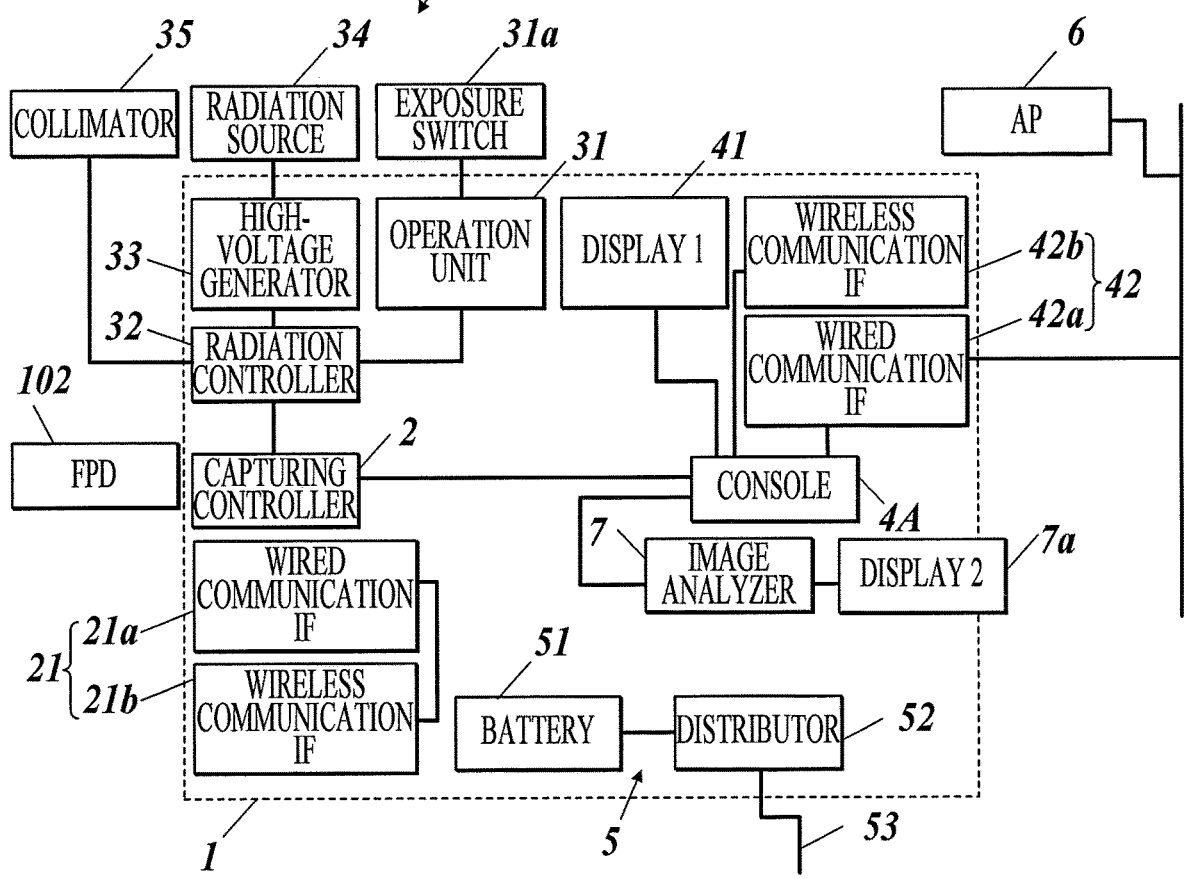
FIG. 3B is a block diagram illustrating the configuration of the radiographic image capturing system according to the second embodiment of the present invention.

FIG. 3A is a side view of the radiographic image capturing system 100A according to the second embodiment and FIG. 3B is a block diagram illustrating the configuration of the radiographic image capturing system 100A.

The image analyzing apparatus 103 according to the first embodiment is separate from the medical cart 101 and connected with the medical cart 101 via a wireless network. With reference to FIG. 3B, the radiographic image capturing system 100A according to this embodiment includes an image analyzer 7 in the medical cart 101A. The image analyzer 7 corresponds to the image analyzing apparatus 103, including the second display. The image analyzer 7 and the console 4A are connected via a wired network. In other words, the connection scheme between the console 4A and the image analyzer 7 cannot be selected in this embodiment.

The second display 7a is provided on, for example, an arm 11 of the medical cart 101.

The image analyzer 7 in the medical cart 101A may reside in a computer connected to the console 4A in the medical cart 101A or in another computer in the medical cart 101A. Alternatively, the image analyzer 7 may be distributed to processors in a computer in the medical cart 101A or in a core area lot calculation.

Figure 4:
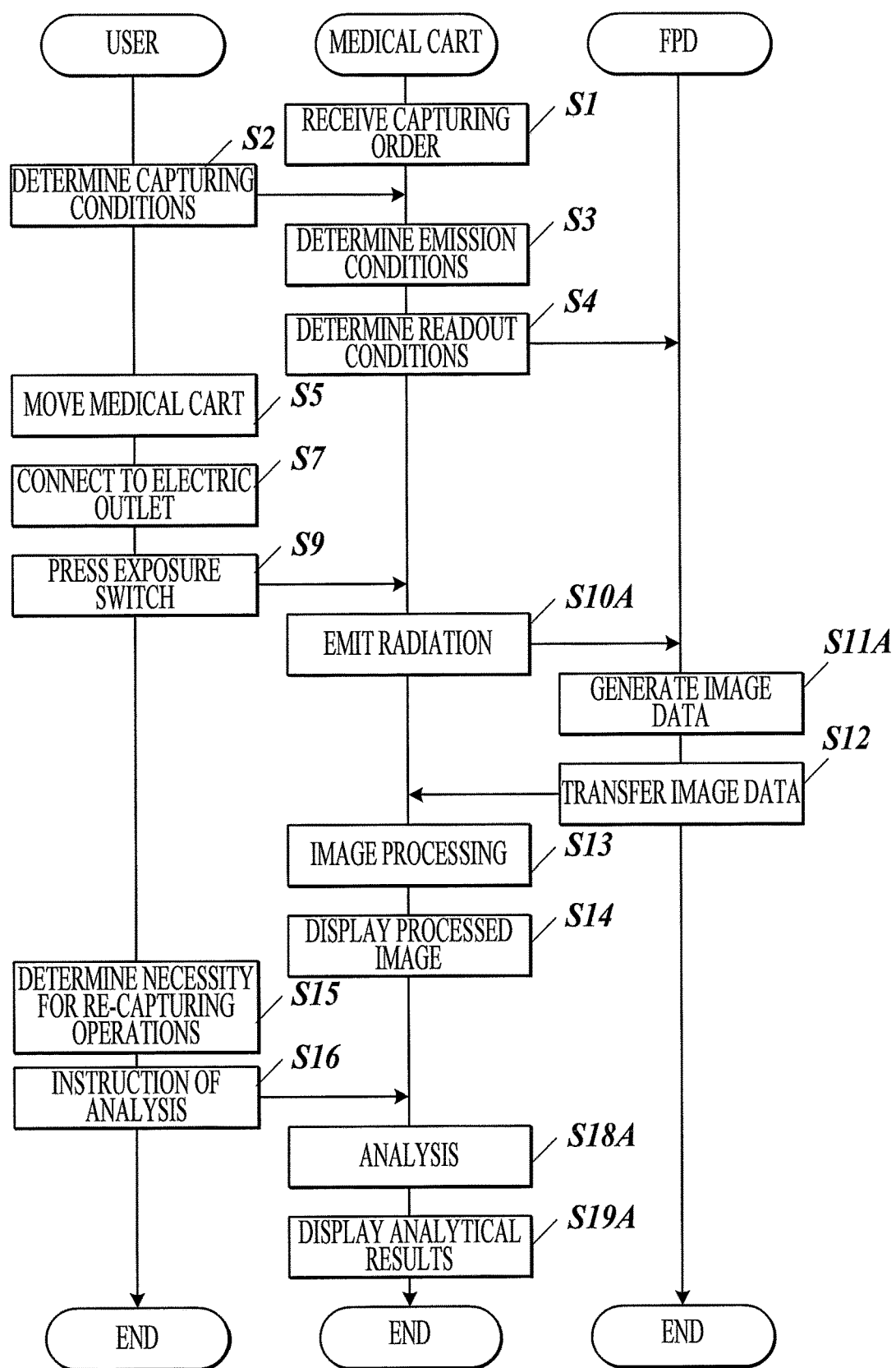
FIG. 4 is a ladder chart illustrating an inspection flow using the radiographic image capturing system according to the second embodiment or a third embodiment.

An inspection flow with the radiographic image capturing system 100A according to this embodiment will now be described. FIG. 4 is a ladder chart illustrating an inspection flow with the radiographic image capturing system according to this embodiment and a third embodiment described below.

The inspection flow with the radiographic image capturing system 100A according to this embodiment is the same as that of the first embodiment up to Step S5. The battery 51 of the medical cart 101A is already in the charged state at Step S5. Since the radiographic image capturing system according to this embodiment uses power of the battery 51, Step S6 (connection of the power cable to an electric outlet) is omitted and Step S7 (positioning) is performed.

In this embodiment, the medical cart 101A is connected to the FPD 102 via a wireless network. Thus, the battery in the FPD 102 also needs to be in the charged state at this step (for example, the FPD 102 is preliminarily connected to the battery 51 of the medical cart 101A). In this embodiment, Step S8 (connection of the communication cable and prevention of detachment) is omitted and Step S9 (press of the exposure switch) is performed.

At the next Steps S10A and S11A, the capturing controller 2 adjusts the timing between the high-voltage generator 33 and the FDP 102 before the capturing operation, which is different from Steps S10 and S11. In detail, in response to the press of the first step of the exposure switch, the medical cart 101 drives the radiation emitting apparatus 3 and sends a drive signal to the FPD 102.

In response to the drive signal, the FPD 102 terminates the resetting process, applies an off-voltage to each scanning line to shift to an electric charge accumulation state, and sends an interlock release signal to the medical cart 101.

In response to the interlock release signal after the press of the second step of the exposure switch 31a, the medical cart 101 calculates the radiation start time and the readout start time at the FPD 102 based on predetermined radiation conditions and sends the calculated time to the FPD 102. The medical cart 101 emits (pulsed) radiation at the calculated start time.

The FPD 102 sequentially applies on-voltage to each scanning line to read image data as described above. Upon completion of the readout process for a scanning line, the FPD 102 performs the readout process for the next scanning line and determines whether the radiation emission period is synchronized with the electric charge accumulation period based on the amount of electric charge for the next scanning line. In the case of synchronization mismatch, the FPD 102 adjusts the out-of-sync state.

In this embodiment, the medical cart 101A and the FPD 102 are connected via a wireless network. Such a configuration may cause delay in stopping readouts. In this case, unexposed frame images may be included in generated frame images. These unexposed frame images may be determined as such and deleted in the signal processing in the FPD 102. Alternatively, all of these unexposed frame images may be transferred to the console 4A, and determined as such and deleted in the image processing in the console 4A. Alternatively, these unexposed frame images may be manually deleted by the user.

Since the wireless communication during readout may add noise to images, image transfer is not performed during the capturing operation in Step S11A, unlike Step S11 in the first embodiment. However, image transfer via the wireless communication may be performed only while readout is not performed. In this case, images may be decimated in the signal processing in the FPD 102 and the decimated or contracted images may be transferred.

After the capturing operation is completed, dynamic image data is transferred to the medical cart 101A via the wireless network (Step S12) and the process goes to Step S13. Alternatively, the FPD 102 may be connected to the medical cart 101A with a wired network after the capturing operation and the dynamic image data may be transferred via the wired network.

The inspection flow from Step S13 (image processing) to Step S16 (instruction to start analysis) is same as that of the first embodiment. After Step S16, the medical cart 101A performs image analysis on processed image data without transferring the processed image data outside the medical cart (Step S18A). In detail, the console 4 of the medical cart 101 transfers the processed image data to the image analyzer 2 in the medical cart 101 and the image analyzer 7 performs image analysis. In this embodiment, winch involves no external communication, the medical cart can perform analysis solely.

The medical cart 101 displays the analyzed image on the second display 7a (Step S19A).

Medical doctors look at the analyzed image appearing on the second display 7a for diagnosis.

A series of inspection processes is thereby completed.

Third Embodiment

A third embodiment of the present invention will now be described.

Only differences from the first embodiment will now be described (The configurations, variations and operations omitted are basically the same as those of the first embodiment.)

Figure 5A:
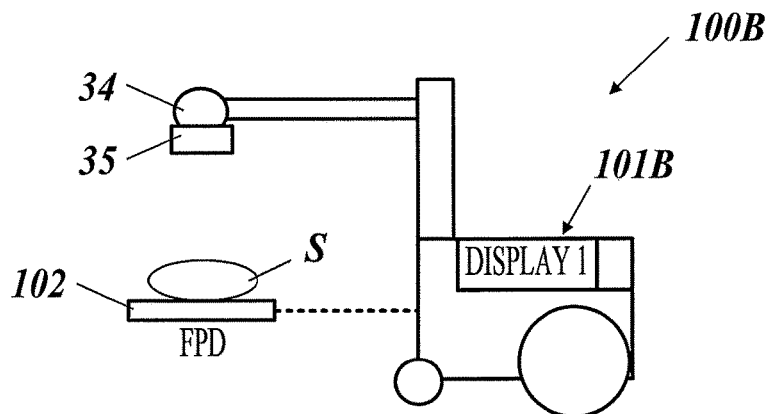
FIG. 5A is a side view of a radiographic image capturing system according to the third embodiment of the present invention.
Figure 5B:
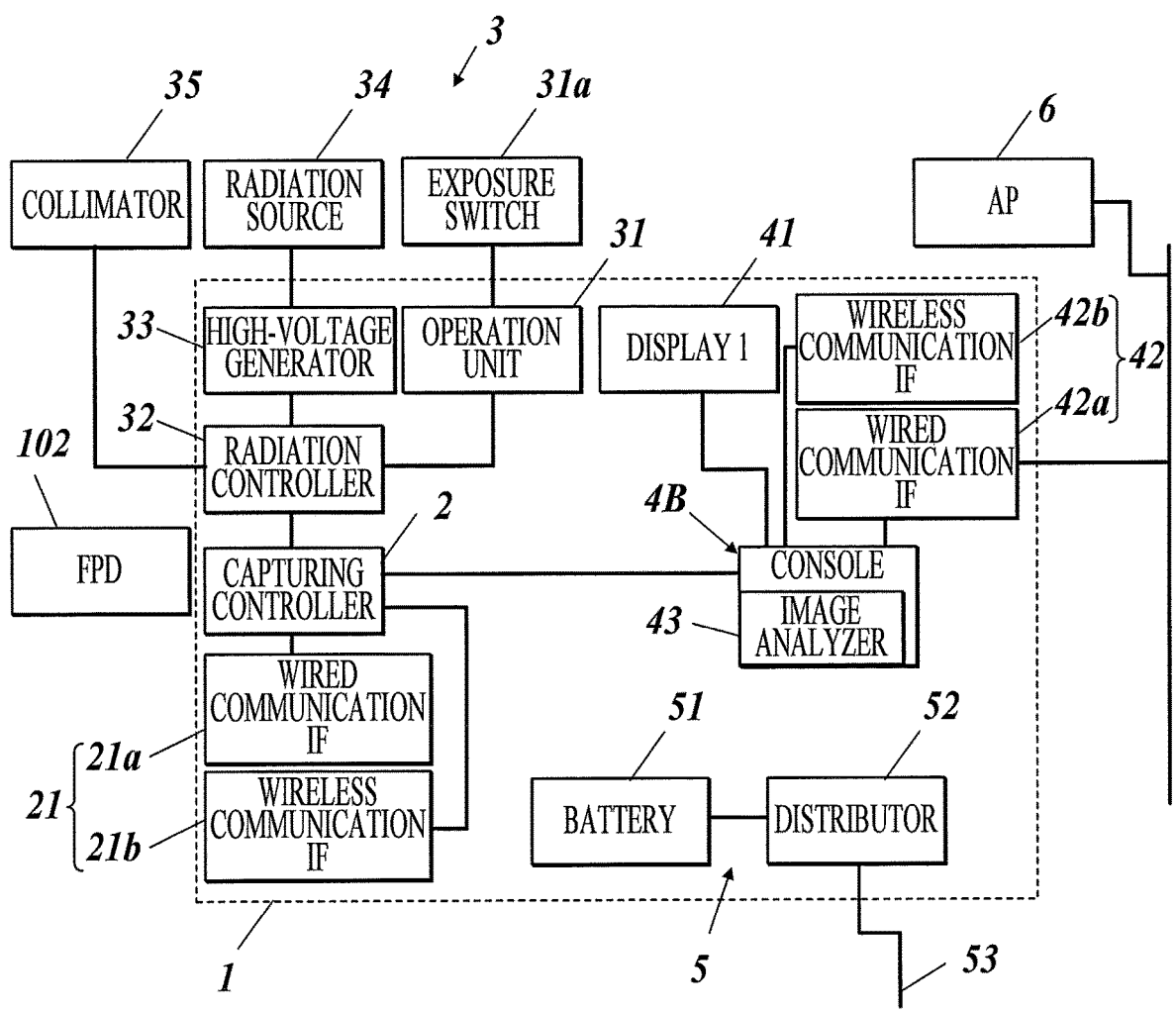
FIG. 5B is a block diagram illustrating the configuration of the radiation image capturing system according to the third embodiment of the present invention.

The image analyzing apparatus 103 according to the first embodiment is separate from the medical cart 101 and connected with the medical cart 101 via a wireless network. With reference to FIG. 5B, the radiographic image capturing system 100B according to this embodiment includes a medical cart 101B that includes an image analyzer 43 in the console 4. The image analyzer 43 corresponds to the image analyzing apparatus 103 in the first embodiment. This configuration allows the image analyzer 43 to directly read image data stored in a memory of the console 4.

The radiographic image capturing system 100B according to this embodiment does not include a display corresponding to the second display 103a and displays the results of image analysis performed at the image analyzer 43 on the display 41 of the console 4.

An inspection flow using the radiographic image capturing system 100B according to this embodiment will now be described.

The inspection flow with the radiographic image capturing system 100B according to this embodiment is the same as that of the first embodiment up to Step S5. The battery 51 of the medical cart 101 is already in the charged state at Step S5. Since the radiographic image capturing system according to this embodiment uses power of the battery 51, Step S6 (connection of the power cable to an electric outlet) is omitted and Step S7 (positioning) is performed.

In this embodiment, the medical cart 101 is connected to the FPD 102 via a wireless network. Thus, the battery in the FPD 102 is also in the charged state at this step (for example, the FPD 102 is preliminarily connected to the battery 51 of the medical cart 101A). In this embodiment, Step S8 (connection of the communication cable and prevention of detachment) is omitted and Step S9 (press of the exposure switch) is performed.

At next Steps S10A and S11A, the radiation controller 32 instructs the high-voltage generator 33 to emit radiation rays and the FPD 102 to generate image data. Unlike Steps S10 and S11, the capturing controller 2 adjusts the timing between the high-voltage generator 33 and the FPD 102 before the capturing operation. In detail, in response to the press of the first step of the exposure switch, the medical cart 101 activates the radiation emitting apparatus 3 and sends an activation signal to the FPD 102.

In response to the activation signal, the FPD 102 terminates a resetting process, applies an off-voltage to each scanning line to shift to an electric charge accumulation state, and sends an interlock release signal to the medical cart 101.

In response to the interlock release signal after the press of the second step of the exposure switch 31a, the medical cart 101 calculates radiation start time and readout start time by the FPD 102 based on predetermined radiation conditions and sends the calculated times to the FPD 102. The medical cart 101 emits (pulsed) radiation at the calculated start time.

The FPD 102 sequentially applies on-voltage to each scanning line to read image data as described above. Upon completion of the readout process for a scanning line, the FPD 102 performs the readout process for the next scanning line and determines whether the radiation emission period is synchronized with the electric charge accumulation period based on the amount of electric charges for the next scanning line. In the case of synchronization mismatch, the FPD 102 adjusts the out-of-sync state.

In this embodiment, the medical cart 101 and the FPD 102 are connected via a wireless network. Such a configuration may cause delay in stopping readouts. In this case, unexposed frame images may be included in generated frame images. These unexposed frame images may be determined as such and deleted in the signal processing in the FPD 102. Alternatively, all of these unexposed frame images may be transferred to the console 4, and determined as such and deleted in the image processing in the console 4. Alternatively, these unexposed frame images may be manually deleted by the user.

Since the wireless communication during readout may add noise to images, image transfer is not performed during the capturing operation in Step S11a, unlike Step S11 in the first embodiment. However, image transfer via the wireless communication may be performed only while readout is not performed. In this case, images may be decimated in the signal processing in the FPD 102 and the decimated or contracted images may be transferred.

After the capturing operation is completed, dynamic image data is transferred to the medical cart 101A via the wireless network (Step S12) and the process goes to Step S13. Alternatively, the FPD 102 may be connected to the medical cart 101 with a wired network after the capturing operation and the dynamic image data may be transferred via the wired network.

The inspection flow from Step S13 (image processing) to Step S16 (instruction to start analysis) is same as that of the first embodiment. After Step S16, the medical cart 101A performs image analysis on processed image data without transferring the processed image data outside of the medical cart 101A (Step S18A). In detail, the console 4 of the medical cart 101A transfers the processed image data to the image analyzer 7 in the medical cart 101A and the image analyzer 7 performs image analysis. In this embodiment, the console 4 and the image analyzer 43 are disposed in the same PC and share a memory, allowing the medical cart to perform analysis promptly and solely.

The medical cart 101 displays the analyzed image on the display 41 (Step S19A).

Medical doctors look at the analyzed image appearing on the display 41 for diagnosis.

A series of inspection processes is thereby completed.

The radiographic image capturing system 100, which involves dynamic state analysis, receives original dynamic image data in the image analyzing unit or the image analyzer and analyzes analytical result data, which is also dynamic images in many cases. Such dynamic images have a data volume significantly greater than still images, resulting in a longer time to transfer and analyze the data.

During rounds to medical wards using the medical cart, the user may be requested to verify the results of the dynamic state analysis of a subject immediately after the capturing operation. To meet such a request, the time to wait for the analytical results to be displayed, including the time to transfer and analyze the data, should be reduced.

The radiographic image capturing system according to this embodiment can save the time to transfer a large volume of dynamic image data and/or analytical result data to an external server and allows the user to confirm analytical results in a relatively short time immediately after the capturing operation during rounds to the medical ward.

The radiographic image capturing system according to this embodiment is less affected by a temporal reduction in bandwidth or a disconnection, which is generally problematic in a communication environment of external servers (in the case of rounds to medical wards, a wireless LAN is used m many cases).

In the inspection with the radiographic image capturing system 100, 100A, or 100B according to the first, second or third embodiment, image data is transferred from the FPD 102 to the capturing controller 2 in the medical cart 101, 101A or 101B, or from the FPD 102 to the image analyzing apparatus 103 (or to the image analyzer 7 or 43) via the console 4, 4A or 4B. In such transfer, each transfer unit involving the transfer of image data from the FPD 102 to the capturing controller 2 in the medical cart 101, 101A or 101B, or to the console 4, 4A or 4B, or the transfer of images from the image controller or from the console 4, 4A, or 4B to the image analyzer 7 or 43 in the medical cart or to the image analyzing apparatus 103 disposed outside the medical cart does not wait for all the image data to be available before the start of the transfer, transfers image data that is ready sequentially according to the bucket brigade rules.

In the case of transfer according to the bucket brigade rules, the order of transfer may be controlled such that information necessary for analysis is transferred in preference. For example, information, such as a total capturing time, a capturing frame rate, the size of each frame image, and the total number of frames, may be transferred first and then image data may be sequentially transferred in the chronological order of the capturing time according to the bucket brigade rules. Such control of the order of the transfer allows an arithmetic operation to be conducted on frame images in the order of the transfer to analyze the intracorporeal movement of a subject based on differences between frame images chronologically arranged. This allows analysis to be started even if all the image data is not available, thus reducing the time to complete the analysis.

Regardless of use or non-use of the bucket brigade rules, the image data may be checked for the transfer state at each transfer unit through which image data passes during the transfer. This can prevent the transfer of some damaged frame images.

If image data is transferred to the image analyzing apparatus 103 or the image analyzer 7 or 43 for analysis, dynamic images may be displayed first and then image analysis is performed during the display of the dynamic images.

EXAMPLE

Various problems relevant to the implementation of the radiographic image capturing systems 100, 100A, and 100B according to the first to third embodiments and specific examples according to the first to third embodiments to solve these problems will be now described.

For components common throughout these embodiments, reference numerals used for the first embodiment are used.

Example 1

The medical cart 101 sends dynamic images used to analyze the dynamic state, for example, from the console 4 to the image analyzing apparatus 103 or to the image analyzer 7 or 43.

As described above, the medical cart according to the present invention has various system configurations: (1) the image analyzing apparatus 103 resides outside the medical cart 101 and is connected to the console 4 via a wired or wireless network (first embodiment), (2) the image analyzer resides in the medical cart 101A and is connected to the console 4 via a wired connection (second embodiment), and (3) the image analyzer is integrated with the console 4B in the medical cart 101B (third embodiment).

The time to send the dynamic image data from the console 4 to the image analyzing apparatus 103 (or the image analyzer 7 or 43) varies depending on the system configuration. Thus, the wireless connection in configuration (1), which has a narrow communication bandwidth than a wired network, takes longer to transfer image data, resulting in the user having to wait for the completion of analysis longer.

The radiographic image capturing system 100 according to Example 1 includes a system configuration determining means for determining the configuration of the medical cart and a radiographic image compressing means in the controller of the console 4. More specifically, the system configuration determining means determines a connection scheme (wired and wireless) between the console 4 and the image analyzing apparatus 103. The radiographic image compressing means compresses image data based on the determined results.

In detail, the memory of the console 4 has a table containing, for example, connection schemes (wired and wireless) and their corresponding actions to be taken (compression, decimation, and inaction). The controller of the console 4 determines the action to be taken in response to the determined results by referring so the table.

If the controller of the console 4 determines that the console 4 and the image analyzing apparatus 103 are connected via a wireless network, the image data sent to the image analyzing apparatus 103 is compressed or decimated. If the controller of the console 4 determines that the console 4 and the image analyzing apparatus 103 are connected via a wired network, the image data sent to the image analyzing apparatus 103 is not compressed.

The medical cart 101 according to Example 1 includes a means for determining whether received image data is compressed or not and a radiographic image decompressing means for decompressing the compressed image data in the controller of the image analyzing apparatus 103.

The controller of the image analyzing apparatus 103 performs image analysis based on compressed or decompressed image data, as needed.

This configuration can reduce user's wait time from the capturing operation to the completion of analysis to an optimal time for each system configuration, thus enhancing the usability of the medical cart.

<Positional Alignment of Units>

Example 2

Figure 6:
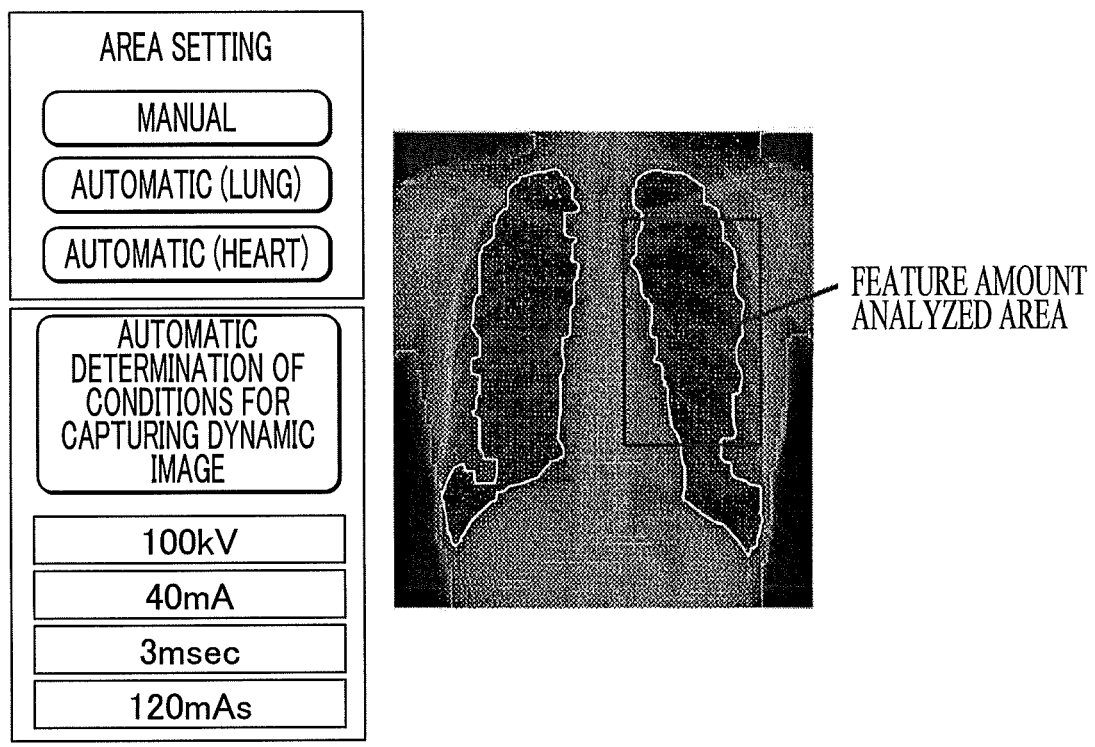
FIG. 6 illustrates an exemplary display on a display of a radiographic image capturing system according to Example 2 of the first to third embodiment.

Radiation conditions must be determined before a user can perform serial capturing operations with the medical cart. The radiation dose predetermined for each target site may be used. The predetermined values may be selected from a screen, as shown in FIG. 6. However, the radiation dose needs to be adjusted in accordance with the physical constitution of a subject.

For a subject who is thinner than the standard physical constitution, the radiation dose should be lower than the predetermined value to avoid unnecessary exposure. For a subject who is thicker than the standard physical constitution, the radiation dose should be increased from the predetermined value because the intensity of radiation is reduced as it passes through the subject until it reaches the FPD 102.

In the case of a subject with a disease, in particular, acquiring an image with an adequate contrast for a diseased portion is important for diagnosis. Unfortunately, the radiation dose absorbed at the diseased portion may differ from that of healthy portions, precluding the proper determination of the adjusted dose only from the visibly apparent physical constitution.

For serial capturing operations with the radiographic image capturing system according to Example 2, the user prepares for the capturing operation (Step S21), as shown in FIG. 7. The preparatory operation includes preparation for emitting radiation, preparation of the FPD 102, the subject, and a radiation target, and positioning of the FPD 102.

To confirm that the area the user wants to capture is within a capturing range properly, radiation conditions tor still images are determined (Step S22) and still-image capturing is performed (Step S23). The medical cart 101 previews the capturing results (Step S24). The user confirms the capturing results.

The console 4 then extracts the feature amount to determine the radiation dose based on a captured still image (Step S25). More specifically, the amount of light incident on the FPD 102 during still-image capturing is calculated based on FPD 102 output. The ratio of the calculated amount of light to the amount of light the FPD 102 needs to receive to achieve an ideal contrast suitable for diagnosis is calculated. The ratio can be used to calculate the correction factor $\alpha$ for calculating the amount of light required for achieving an ideal contrast during still-image capturing. As shown in FIG. 8, the feature amount of an ideal still image captured can be acquired by multiplying the feature amount extracted by the correction factor $\alpha$.

The correlation between the radiation dose for still-image capturing and the dynamic image radiation dose is preliminarily determined. The collection factor $\beta$ is then calculated from this correlation to determine the serial-capturing radiation dose. The collection factor $\beta$ may be a constant or equation. Alternatively, the correction factor $\beta$ is a constant or equation for each target site. Alternatively, the correction factor $\beta$ may be selected from a look-up table for individual target sites or radiation doses of ideal still images.

With reference to FIG. 8, the feature amount of an ideal still image is determined by multiplying the extracted feature amount by the correction factor $\alpha$. The feature amount of an ideal dynamic image is determined by multiplying the feature amount of the ideal still image by the correction factor $\beta$.

The radiation dose A for still-image capturing operations and the radiation dose B for serial capturing operations can be expressed by Expression (1):

$$B = \alpha \times \beta A \quad (1)$$

The radiation dose may be determined by the product of the voltage and current of the X-ray tube and the irradiation time for each pulse, or the product of X-ray tube current and the irradiation time for each pulse.

The following four serial capturing settings are available for a still-image capturing setting:

Case (1): mA setting for dynamic image=$\alpha \times \beta \times$mA setting for still image (without any other change)

Case (2): ms setting for dynamic image=$\alpha \times \beta \times$ms setting for still image (without any other change)

Case (3): mA setting for dynamic image=$\sqrt{(\alpha \times \beta)} \times$mA setting for still image, ms setting for dynamic image=$\sqrt{(\alpha \times \beta)} \times$ms setting for still image Case (4): mAs setting for dynamic image=$\alpha \times \beta \times$mAs setting for still image Radiation conditions are determined in such a manner (Step S26) and serial capturing operations are performed (Step S27).

Example 2 have the following variation:

Standard still-image settings, are predetermined for each target site.

The ratio $\gamma$ of the standard still-image settings to ideal settings is calculated fused on a captured still image.

Standard dynamic-image settings are predetermined for each target site.

Actual serial-capturing settings are determined by multiplying the standard settings by the ratio $\gamma$ and then serial capturing operations are performed.

In this case, the product $\alpha \times \beta$ in the correction defined in Cases (1) to (4) may be replaced with the ratio $\gamma$.

A radiation automatic exposure control (AEC) may be disposed between the radiation source 34 anti the FPD 102 during still-image capturing to control the radiation dose with the AEC.

An area dosimeter (DAP) may be positioned between the radiation source and the FPD 102 to measure the radiation dose.

The radiation dose may be controlled and measured during still-image capturing through emission from the AEC and determination of the radiation dose from DAP output.

The relation between DAP output and the voltage and current of the X-ray tube and the irradiation time for each pulse is preliminarily stored in the console memory in the form of a table. The voltage and current of the X-ray tube and the irradiation time for each pulse are calculated from the DAP output through table search or with a conversion formula. The voltage and current of the X-ray tube and the irradiation time for each pulse during the serial capturing operation can be acquired by the above method.

To calculate and determine a radiation field, an analyzed area in a dynamic image is determined using a captured still image. More specifically, an image with an ideal captured area is overlapped on the captured image to tune the overlapping position to minimize the difference between these images. This allows the target sites of the two images to match as much as possible.

The ideal captured area and the captured image are compared to calculate a difference. These two images are moved by, for example, varying the position of the FPD 102 or the radiation source or the radiation field controlled by the collimator 35 disposed between the radiation source 34 and the FPD 102 so as to reduce the difference. The radiation field controlled by the collimator 35 disposed between the radiation source 34 and the FPD 102, in particular, may be automatically corrected through electric control of the collimator 35.

Serial capturing under radiation conditions determined from the radiation dose absorbed at the captured area based on the resulting captured still image can prevent capturing of dynamic images, such as an unclear dynamic image or a low-contrast dynamic image due to a low radiation dose, unsuitable for diagnosis.

Such serial capturing operations can prevent exposure of a subject to radiation with a dose greater than that necessary to capture dynamic images suitable for diagnosis.

Example 3

During capturing of a lying subject, the subject may apply the body weight to either the right or left of the body axis. A significant bias in the applied body weight may result in a greater deformation of internal structures (bones and internal organs) of the subject than no bias in the applied body weight, resulting in a captured image unsuitable for diagnosis.

Accurate capturing requires correction of such a bias in applied body weight, however the direction of the applied body weight is difficult for the user to determine from the appearance of the subject.

Figure 9A:
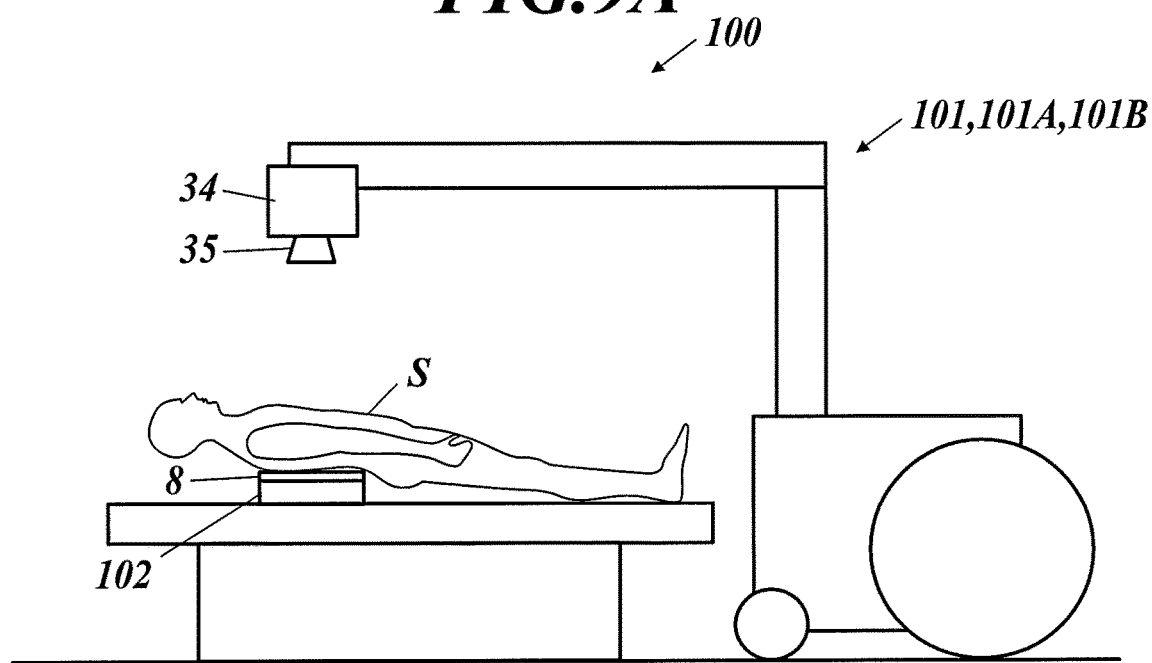
FIG. 9A is a side view of a radiographic image capturing system according to Example 3 of the first to third embodiments.

To cope with this problem, the radiographic image capturing system 100 according to Example 3 is provided with a pressure sensor 8 (or a pressure sensor array) capable of measuring the pressure on the top of the FPD 102 (the top surface of the FPD 102 placed on a bed), as shown in FIG. 9A.

The pressure sensor 8 is connected to the capturing controller 2 (see FIG. 1B) via a wired or wireless network or via the FPD 102 to send the measured pressure to the capturing controller 2.

Figure 9B:
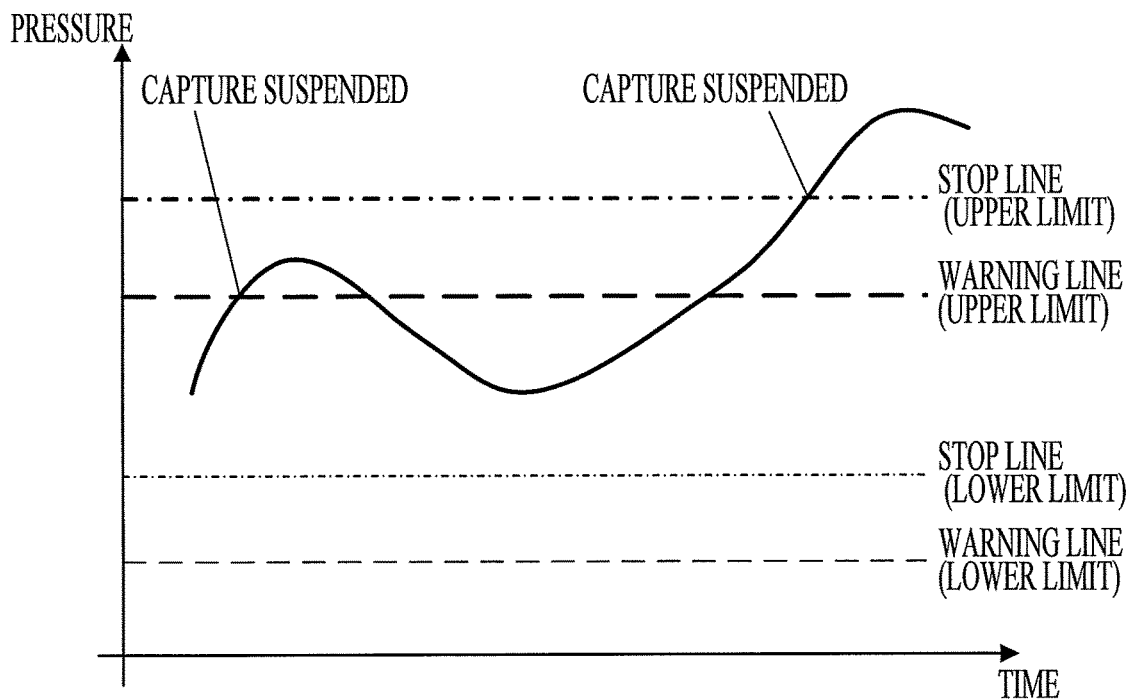
FIG. 9B is an exemplary graph on a display of the radiographic image capturing system according to Example 3 of the first to third embodiments.

The capturing controller 2 also has a function to display a graph or surface distribution diagram of the pressure values acquired from the pressure sensor 8 or the pressure sensor array, for example, on the display 41, as shown in FIG. 9B.

A strain sensor may be used in place of the pressure sensor.

This configuration allows the user to check for the pressure applied to the FPD 102 or pressure distribution displayed on the display 41 to recognize the direction of the pressure applied to the FPD 102. For example, if the user finds that the subject applies an excess force to the left side and that the body inclines to the left side, the user can instruct the subject to correct the position by shifting the weight to the right so that the pressure is applied evenly.

Example 4

During serial capturing operations, the movements of breathing lungs or a beating heart is captured. A significant body motion of a subject may add the body motion to the movements of the lungs or heart in a resulting dynamic image. Such a dynamic image containing the body motion cannot be used for diagnosis, resulting m excess exposure of the subject.

To prevent such an excess exposure, it is required that the user can immediately recognize any significant body motion.

The radiographic image capturing system 100 according to Example 4 is provided with a pressure sensor 8 (or pressure sensor array), similar to Example 3.

The capturing controller 2 determines whether the pressure, the variation in pressure per unit time, the difference in maximum and minimum pressures during the capturing period, or the feature amount calculated from the pressure exceeds its predetermined threshold. If the parameter exceeds the threshold, the capturing controller 2 displays a warning of the possibility of a significant body motion on, for example, the display 41 and instructs the radiation emitting apparatus 3 to stop emission of radiation rays.

The warning needs not be always visual; it may be auditory, or visual and auditory indications may be used in combination.

This configuration allows the user or subject to recognize the occurrence of body motion in the subject by the warning even if the user fails to notice it. This can reduce the body motion.

In response to determination that the body motion in the subject exceeds the threshold (or makes the captured image unsuitable for diagnosis), the capturing is stopped, even if the user fails to notice it. This can prevent excess exposure of the subject.

Example 5

In the case of capturing at an operation room, a movable surgical bed forces, the user to determine the relative positions of the three units of the FPD 102, the radiation source 34, and the surgical bed concurrently, resulting in burdensome preparative operations.

In the capturing operation with the radiographic image capturing system according to Example 5, the positions of the FPD 102 and the radiation source 34 are determined with reference to the position of the surgical bed. In detail, the surgical bed may be provided with, for example, a concave (not shown) which can fit to the FPD 102. The concave is fit to the FPD 102 before the capturing operation.

Alternatively, the surgical bed may be provided with a part fit to the medical cart or marked with a dot at which the medical cart is stopped. The positioning of the medical cart 101 is automatically followed by the positioning of the radiation source 34.

One of the FPD 102 and the radiation source 34 positioned to the surgical bed is then positioned to the other. A subject is then positioned to the reference position of the surgical bed before the capturing operation.

This configuration requires positioning of only the FPD 102 and the radiation source 34, saving the trouble of the preparative operation.

Example 6

The medical cart 101, 101A, or 101B according to this embodiment is substantially c-shaped in side view and includes an arm provided with the radiation source 34 at the end of the arm and the FPD 102 on the other end (hereinafter referred to as the C arm 12). The medical cart 101 provided with the C arm 12 is disposed such that a subject S lying on a surgical bed T is disposed between the radiation source 34 and the FPD 102. The C arm 12 determines the relative positions of the radiation source 34 and the FPD 102, facilitating the positioning. The C arm is movable, hence the user can capture the subject S from any direction.

If the radiation source 34 is disposed above the subject S, the FPD 102 is disposed below the subject S and radiation is emitted to the subject from above. Thus, the surgical bed T is disposed between the subject and the FPD 102 and the subject is distant from the FPD 102. This configuration may produce low-quality captured images.

Figure 10:
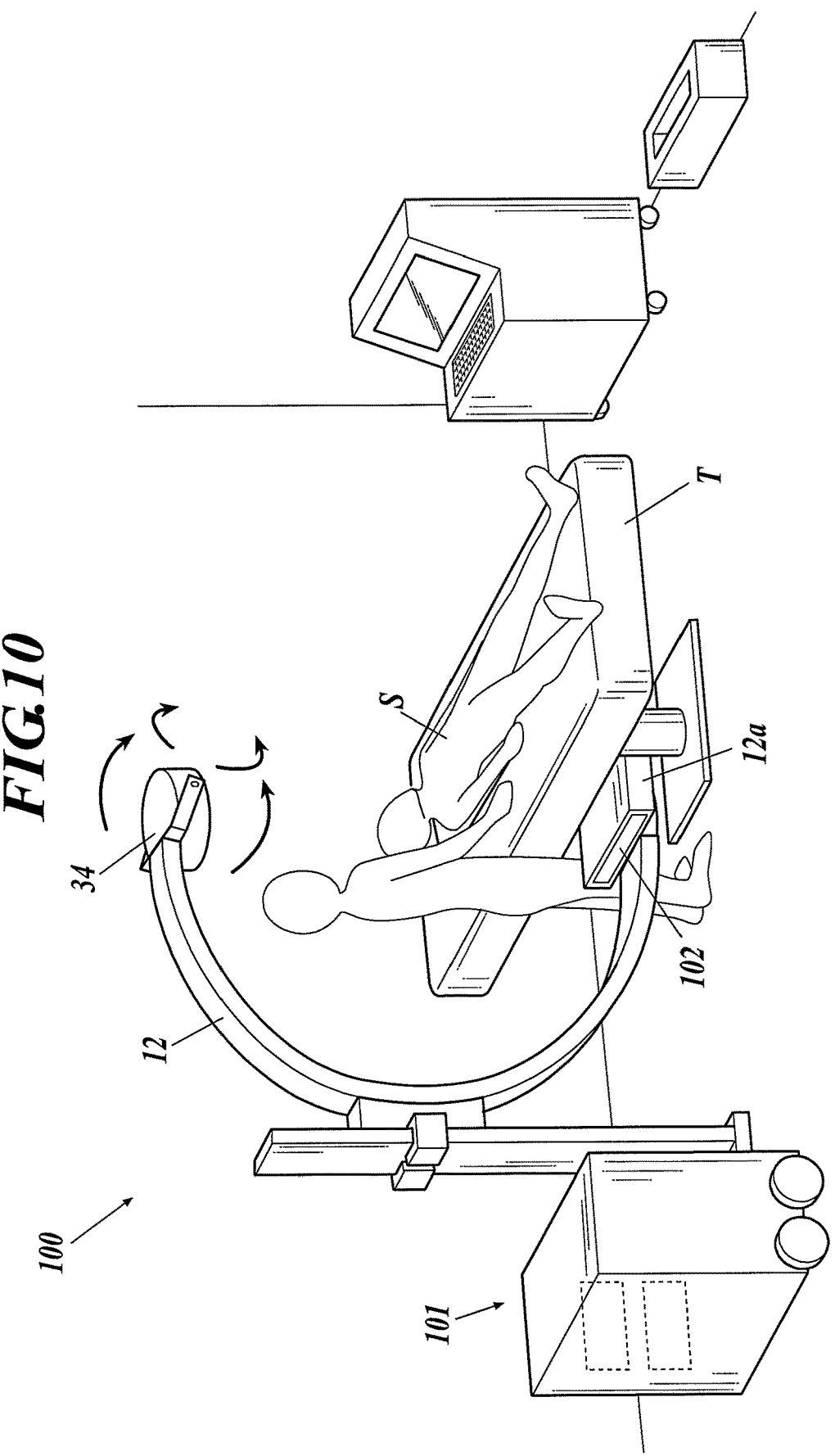
FIG. 10 is a perspective view of a radiographic image capturing system according to Example 6 of the first to third embodiments.

With reference to FIG. 10, the C arm 12 of the radiographic image capturing system 100 according to Example 6 is provided with the radiation source 34 fixed at one end of the C arm 12 and a FPD holder 12a at the other end. The FPD holder 12a detachably holds the FPD 102.

A tip of the communication cable extending from the communication unit 21 of the medical cart 101 may be attached to the FPD holder 12a. After the FPD 102 is mounted in the FPD holder 12a, the FPD 102 is connected to the communication cable, enabling a wired communication between the FPD 102 and the medical cart 101.

If the FPD 102 is not mounted in the FPD holder 12a, the user may be notified of a simple message. For example, in response to the press of the first step of the exposure switch, a warning message is displayed on the display 41 of the console.

Alternatively, the FPD holder may be provided with a function to identify the FPD 102. If the mounted FPD 102 does not have a serial capturing function (can capture only still images), the FPD holder may issue a warning or restrict the exposure.

In the case of the FPD 102 connected to the medical cart 101 via a wireless network, the angle of view of a captured image may be reduced to shorten the time to transfer images between the FPD 102 and the wireless interface 21b of the medical cart 101. The radiation controller 32 may control the collimator 35 to reduce the amount of light passing through the collimator 35 in line with the angle of view of the captured image. The radiation controller 32 may decimate frame images if image data transfer cannot be promptly or timely performed.

A grid may be provided on the face, opposite to the FPD holder 12a, of the radiation source 34.

This configuration, including the FPD holder 12a holding the FPD 102, allows capturing to be performed while maintaining the benefits of the medical cart provided with a C arm, such as being ready for positioning and capturing from any angle. In order to dispose the FPD 102 immediately below the subject, the FPD 102 is removed from the FPD holder and placed between the subject S and the surgical bed T. This allows the subject S to be captured while the FPD 102 is kept close to the subject S with no surgical bed T between the subject S and the FPD holder.

The removable FPD 102 can be readily replaced if it fails, resulting in prompt restoration.

<Battery>

Example 7

The battery in the FPD 102 has a predetermined capacity and the FPD 102 cannot be connected to an electric outlet during the capturing operation at a round destination. A user should pay attention to the battery level during the capturing operation to prevent the FPD 102 from being inoperative during rounds due to running out of battery.

The distributor 52 of the medical cart 101 of the radiographic image capturing system 100 according to Example 7 is provided with a connector. A power cable C extending from the FPD 102 is to be connected to the connector.

With reference to FIG. 11, the medical cart 101 is connected to the FPD 102 with the connector via the power cable C. This allows the battery 102a in the FPD 102 to be charged with power from the battery 51 in the medical cart 101.

The power fed from the medical cart 101 via the power cable need not be used to charge the battery 102a; the power may be used to directly drive the FPD 102.

This configuration allows power to be fed to the FPD 102 from the battery 51 in the medical cart, which has a relatively larger capacity than the battery 102a in the FPD 102, saving the trouble to check the battery 102a in the FPD 102 for the battery level.

Example 8

To address the problem, described in Example 7, that attention should be paid to the charge level of the battery 102a in the FPD 102, the radiographic image capturing system 100 according to Example 8 monitors a power switch of the FPD 102 while the capturing controller 2 is connected to the FPD 102. Upon detection of turning on of the power switch, the radiographic image capturing system 100 drives various units of the medical cart 101.

When the power switch of the medical cart 101 is turned on while the power switch of the FPD 102 is not, the capturing controller 2 sends to the FPD 102 a control signal to instruct the FPD 102 to start.

In response to the control signal to start the FPD 102 from the capturing controller 2, the FPD 102 can start regardless of the operation of its power switch.

This configuration allows both the medical cart 101 and the FPD 102 to be started concurrently if the power switch of one of the medical cart 101 and the FPD 102 is pressed. This saves trouble to activate both the medical cart 101 and the FPD 102 with separate processes, facilitating preparative operations.

<Wireless Capturing>

Example 9

A wireless network may be more unstable than a wired network. A high transfer rate for frame images may deteriorate communication conditions during transfer of dynamic image data over a wireless network and preclude complete transmission of a planned frame image, results in unstable transfer, for example, delay in transfer of the next frame image.

Figure 12:
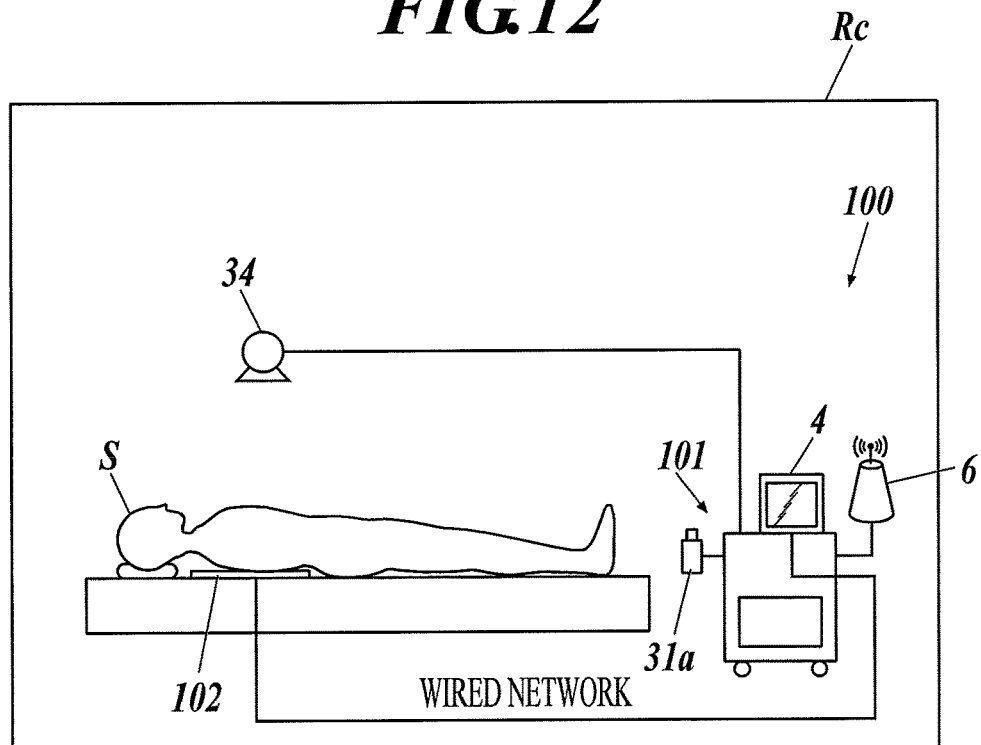
FIG. 12 is a side view of a radiographic image capturing system according to Example 9 of the first to third embodiments.

With reference to FIG. 12, the radiographic image capturing system 100 according to Example 9 is equivalent to the radiographic image capturing system according to the first embodiment, where the medical cart 101 and the FPD 102 are connected via a communication cable. In the radiographic image capturing system, the capturing controller 2 monitors the wireless communication environment using, for example, the access point 6.

If the capturing controller 2 determines that frame images can be transferred at a rate higher than a predetermined transfer rate even over a wireless network; then the wireless network is maintained between the medical cart 101 and the FPD 102. If the capturing controller 2 determines that frame images can only be transferred at a rate lower than a predetermined transfer rate, the connection scheme between the medical cart 101 and the FPD 102 is switched to the wired network.

This configuration allows image data to be transferred without delay even if the communication conditions are deteriorated during image data transfer.

<Synchronization of Exposure and Prevention of Erroneous Exposure>

Example 10

Figure 13:
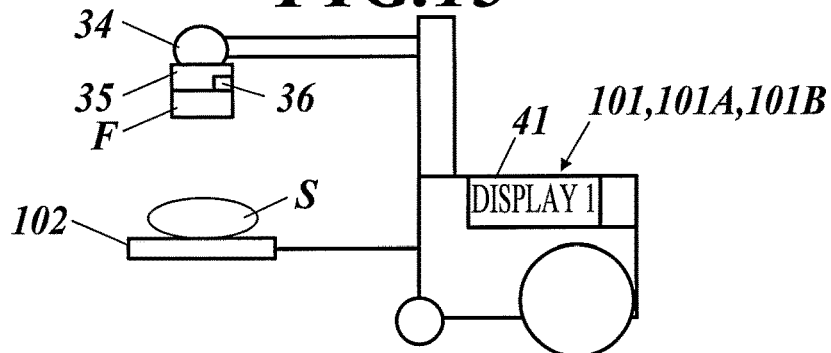
FIG. 13 is a side view of a radiographic image capturing system according to Example 10 of the first to third embodiments.

With reference to FIG. 13, the collimator 35 of the radiographic image capturing system 100 according to Example 10 may include an additional filter F and is provided with a sensor 36 that detects the mount of the additional filter F and determines the type of filter, if mounted.

When the user selects the serial capturing mode or starts the exposure in the serial capturing mode (presses the first step of the exposure button), the radiation emitting apparatus 3 instructs the sensor 36 to detect the additional filter and determine the type of filter, and checks for the mount of the additional filter or the type of filter for the specified capturing mode.

The radiation emitting apparatus 3 matches the information on the additional filter and the type of fiber detected by the sensor with that determined by the sensor for the specified capturing mode. If the radiation emitting apparatus 3 determines that a proper additional filter is not mounted, a warning is issued on the display 41.

Figure 14:
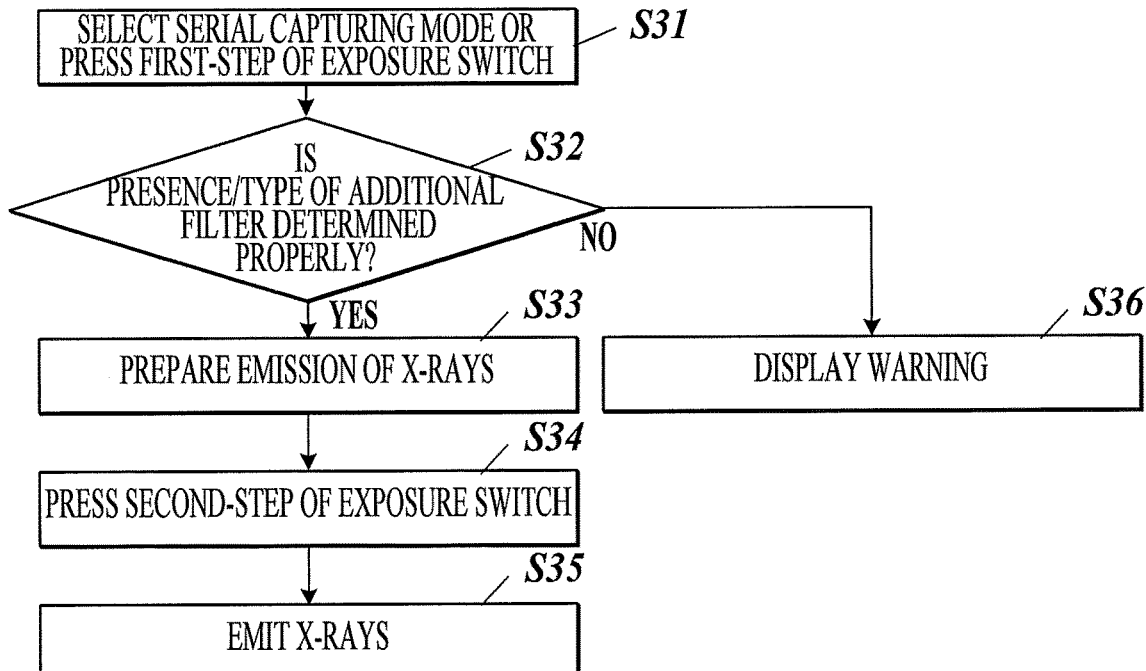
FIG. 14 is a flow chart of a control process of the radiographic image capturing system according to Example 10 of the first to third embodiments.

In response to the selection of the serial capturing mode or the start of exposure in the serial capturing mode by the user (Step S31), the radiation emitting apparatus 3 of the radiographic image capturing system 100 according to Example 10 matches the information on the additional filter and the type of filter detected by the sensor with that determined for the specified capturing mode (Step S32), as shown in FIG. 14.

If a proper additional filter is determined to be mounted at Step S32 (Step S32: Yes), the radiographic image capturing system prepares emission of radiation rays and waits for the press of the second-step of the exposure switch 31a (Step S33).

In response to the press of the second-step of the exposure switch 31a by the user (Step S34), the radiation source 34 emits radiation rays (Step S35).

If a proper additional filter is not determined to be mounted at Step S32 (Step S32: No), a warning is issued (Step S36).

If the exposure operation is continued (i.e., the second step of the exposure button is pressed) after issue of the warning, the exposure operation may be performed or restricted.

This configuration can prevent the user from continuing the capturing operation while the user misrecognizes the presence of the additional filter or a wrong filter type is mounted.

Example 11

In the radiographic image capturing system 100 according to Example 11, the console 4 acquires a first frame image and measures the brightness of the first frame image immediately after the acquisition during the serial capturing operation.

Furthermore the console 4 also issues a warning indicating that the user may misrecognize the presence of the additional filter or use a wrong filter type if the measured brightness is outside of a predetermined range, in other words, the radiation dose is high.

Figure 15:
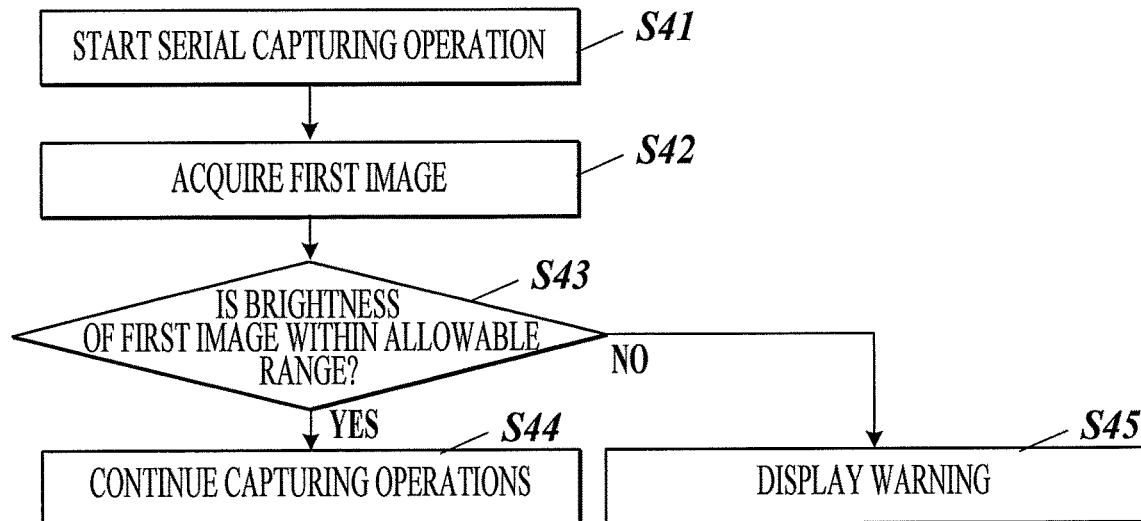
FIG. 15 is a flow chart of a control process of a radiographic image capturing system according to Example 11 of the first to third embodiments.

With reference to FIG. 15, the console 4, having the above function, of the radiographic image capturing system 100 according to Example 11 acquires a first frame image (Step S42) in response to the start of serial capturing operations (Step S41). The console 4 measures the brightness of the acquired first image and determines whether the brightness is within the predetermined range (Step S43).

If the measured brightness is within the predetermined range (Step S43: Yes); then the capturing operation continues (Step S44).

If the measured brightness is outside the predetermined range (Step S43: No), a warning is issued (Step S45). After Step S45, exposure may be continued or stopped.

This configuration can prevent the user from continuing the capturing operation while the user misrecognizes the presence of the additional filter or a wrong filler is mounted, similar to Example 10.

Example 12

In the serial capturing operation by pulsed radiation, the FPD 102 is put in the electric charge accumulation state during the emission of pulsed radiation rays and performs readout after the completion of emission. A higher frame rate is required for a smoother playback of dynamic images. To increase the frame rate, the electric charge accumulation time and/or readout time should be reduced. Unfortunately, a reduction in the readout time of the FPD 102 results in complicated optimization of the operational parameters for readout ICs. Thus, the electric charge accumulation time should be reduced without modification of the readout time.

However, reduced electric charge accumulation time also requires a reduction in radiation irradiation time per frame. In addition, a minimum irradiation time varies depending on the high-voltage generator. Some high-voltage generators may preclude the completion of the emission of pulsed radiation rays within the electric charge accumulation time.

To cope with these problems, the radiation controller 32 of the radiographic image capturing system 100 according to Example 12 stores a predetermined threshold. The threshold is an inverse of a minimum irradiation time of pulsed radiation rays which can be emitted by the radiation emitting apparatus 3. In response to the selection of the pulsed capturing mode and the setting of a frame rate, the radiation controller 32 compares the frame rate setting with the threshold. If the set frame rate is equal to or less than the threshold (the minimum irradiation time does not exceed the electric charge accumulation time of the FDP 102); pulsed radiation is performed. If the set frame rate is more than the threshold (the minimum irradiation time exceeds the electric charge accumulation time of the FPD 102), continuous radiation is performed.

This configuration enables serial capturing operations at a high frame rate even with a radiation emitting apparatus with a minimum radiation irradiation time that cannot be short enough.

Example 13

The serial capturing operation is intended to capture variations in a target site involved in respiration of a subject. This requires the timing of respiration to be matched with the timing of capturing. In the serial capturing operation, capturing is performed while the timing of respiration of the subject is instructed by the user or automated voice.

Unfortunately, the user has no means to know whether the subject respires in accordance with the instruction during the capturing operation and has to confirm it with a captured image. In other words, if the subject fails to respire in accordance with the instruction, the image captured at that time cannot be used for diagnosis, resulting in an excess exposure of the subject.

The radiographic image capturing system 100 according to Example 13 is provided with a pressure sensor 8 (or a pressure sensor array) capable of measuring the pressure on the top of the FPD 102, similar to Example 3.

The pressure sensor 8 is connected to the capturing controller 2 to send the measured pressure to the capturing controller 2.

The capturing controller 2 displays a chronological variation in measured pressure, for example, on the display 41 of the console 4. The displayed content may be a graph where the capturing period is on the horizontal axis and the pressure or feature amount calculated from the pressures is on the vertical axis.

The timing in the variation in the displayed pressure represents the timing of the respiration.

This configuration allows the user to confirm that respiration is performed at a right timing during the capturing operation and can effectively prevent the capturing operation from continuing despite the respiration at a wrong timing, and thus prevent an excess exposure of the subject.

<Handling of Dynamic Images (Heavy Data), Data Flow, and Allocation of SW>

Example 14

The radiographic image capturing system 100, which involves dynamic state analysis, receives original dynamic image data in the image analyzing apparatus 103 or the image analyzer 7 or 43 and analyzes analytical data (analytical results), which is also dynamic images in many cases. Such dynamic images have a data volume significantly greater than still images, resulting in a longer time to transfer and analyze the data.

During rounds to medical wards using the medical cart 101, the user may be requested to verify the results of the dynamic state analysis of a subject immediately after the capturing operation. To meet such a request, the time to wait for the analytical results to be displayed, including the time to transfer and analyze the data, should be reduced.

Figure 16:
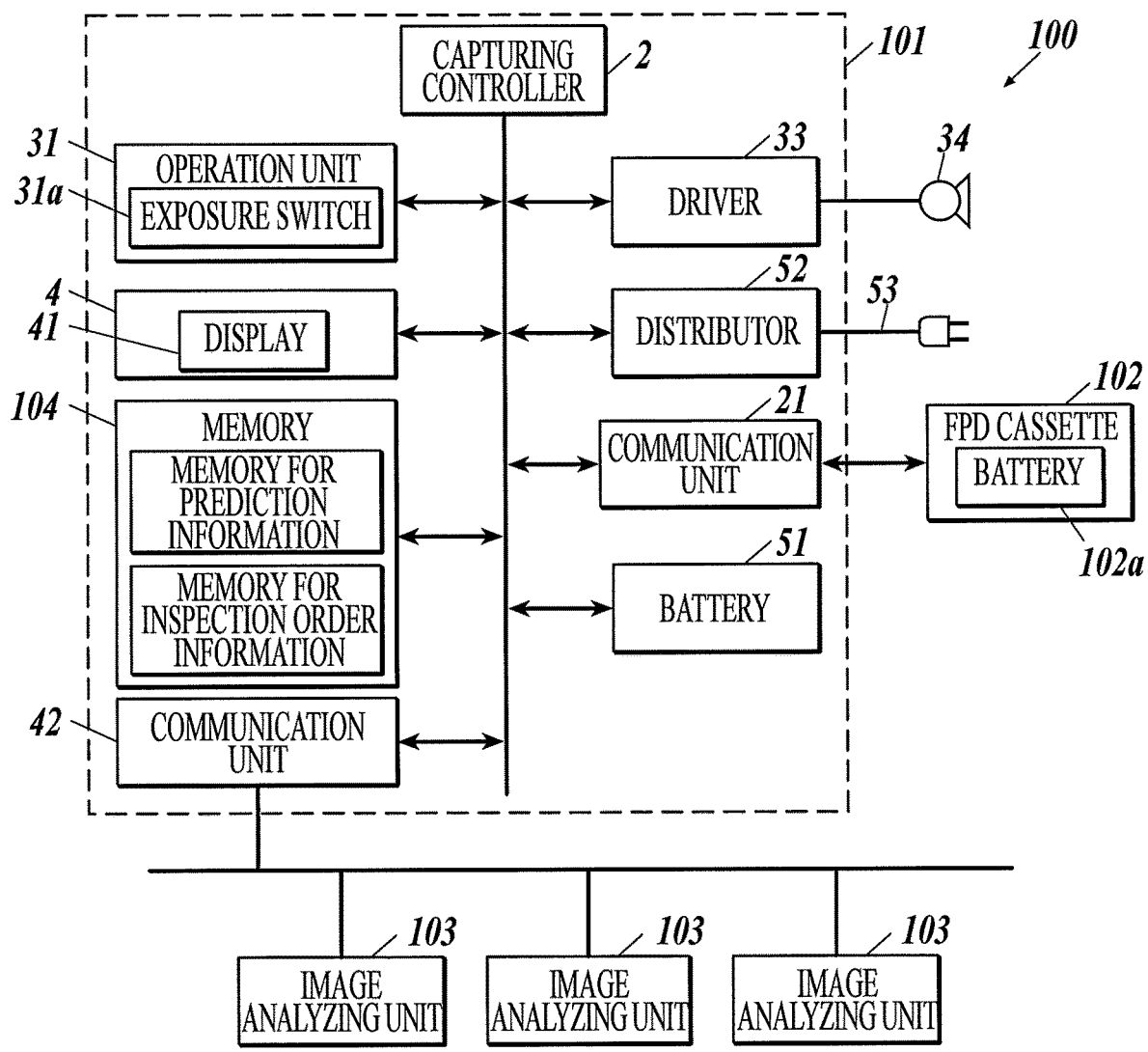
FIG. 16 is a block diagram illustrating a configuration of a radiographic image capturing system according to Example 14 of the first to third embodiments.

With reference to FIG. 16, the radiographic image capturing system 100 according to Example 14 includes multiple image analyzing units 103.

In detail, the image analyzing apparatus 103 may be an unused external analytical server around the medical cart. A server that imposes a low load on network during transfer (for example, close to the medical cart or a wide network bandwidth) or has a high analytical capacity (high-end PC or a large unused resource) should be selected as an external analytical server.

The selection of such a server can further reduce time to wait for the analytical results to be displayed.

Example 15

Figure 17:
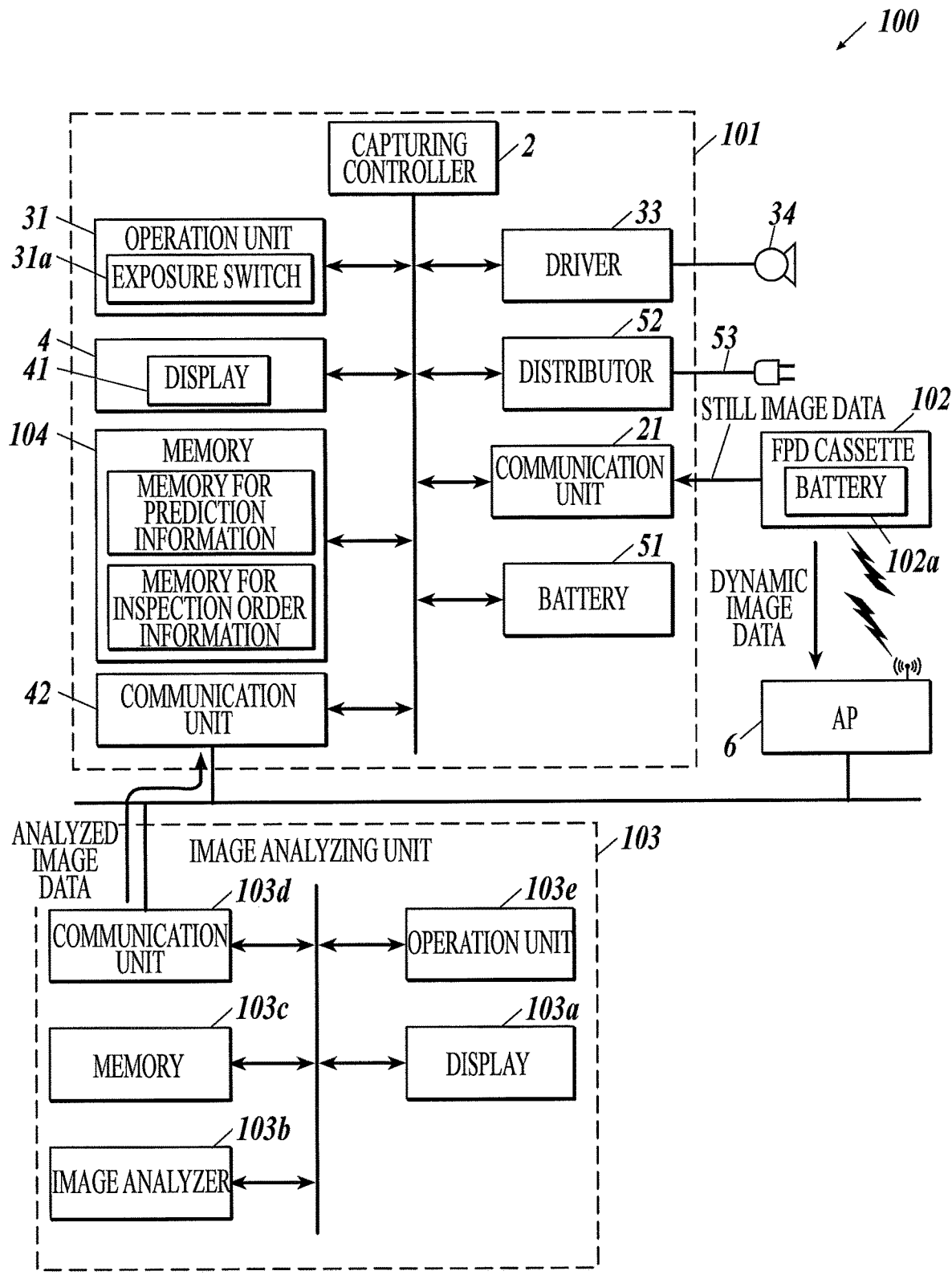
FIG. 17 is a block diagram illustrating a configuration of a radiographic image capturing system according to Example 15 of the first to third embodiments.

In order to shorten the waiting time for the display of analytical results at a round destination, as described in Example 14, the FPD 102 of the radiographic image capturing system 100 according to Variation 15 can directly send dynamic image data to the image analyzing apparatus 103 (or the image analyzer) via the access point 6, as shown in FIG. 17.

In the case of the generation of still image data, the controller of the FPD 102 sends the generated image data to the medical cart 101 via the communication unit 21. In the case of the generation of dynamic image data, the controller of the FPD 102 sends the generated image data to the image analyzing apparatus 103 via the access point 6.

The console 4 receives the analytical result data from the image analyzing apparatus 103 and displays the analyzed image based on the analytical result data on the display 41.

This configuration allows dynamic image data, which requites much transfer and analytical time, to be directly transferred from the FPD 102 to the image analyzing apparatus 103 and only the analytical results to be sent back to the console of the medical cart 101. This can reduce the waiting time for the display of the analytical results by the time for sending image data from the console 4 to the image analyzing apparatus 103.

During a round that requires both still-image capturing and serial capturing operations to be performed, the still-image capturing operation can be performed, while analysis is performed (on the background) at the image analyzing apparatus 103 after capturing of dynamic images. This increases the efficiency of the capturing operation.

Example 16

Figure 18:
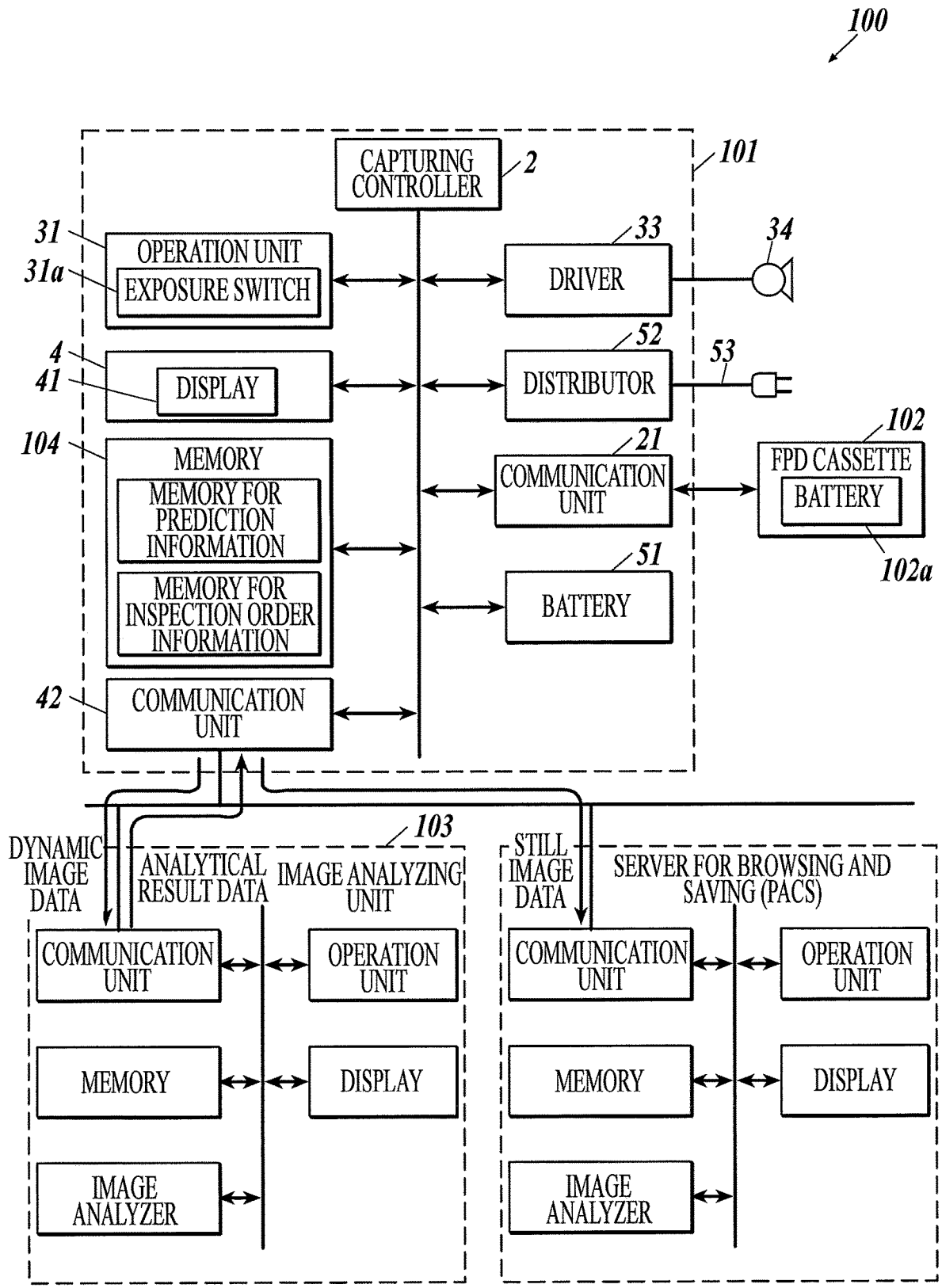
FIG. 18 is a block diagram illustrating a configuration of a radiographic image capturing system according to Example 16 of the first to third embodiments.

In order to shorten the waiting time for the display of analytical results at a round destination, as described in Example 14, the image analyzing apparatus 103 of the radiographic image capturing system 100 according to Variation 16 can transfer analytical result data to the console 4, in the radiographic image capturing system 100 according to the first embodiment, as shown in FIG. 18.

The console 4 displays an analyzed result image based on analytical result data received from the image analyzing apparatus 103 on the display 41.

Still image data is directly sent from the console 4 to an external server for browsing and saving (PACS).

This configuration allows a still image to be captured while the image analyzing apparatus 103 is performing analysis (on the background) after the capturing of dynamic images during a round that requires both still-image capturing and serial capturing operations to be performed as described in Example 14. This improves the efficiency of the capturing operation.

Example 17

Figure 19:
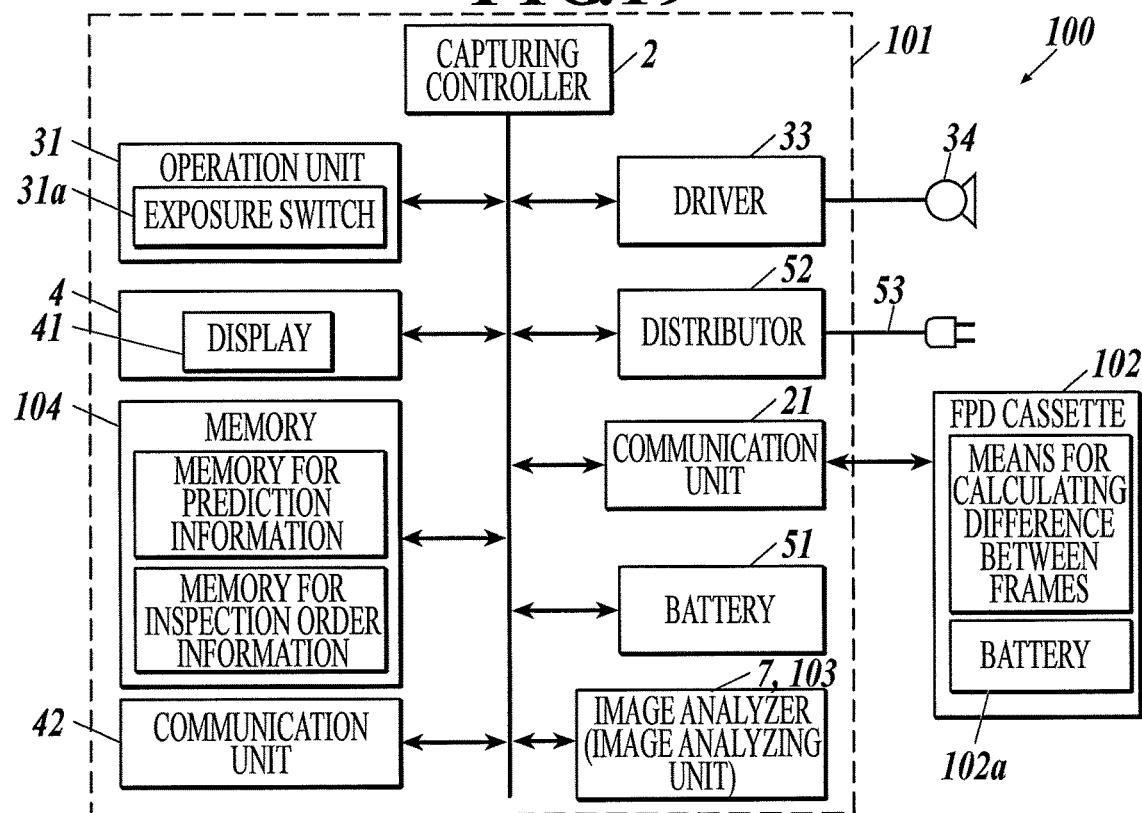
FIG. 19 is a block diagram illustrating a configuration of a radiographic image capturing system according to Example 17 of the first to third embodiments.

In order to shorten the waiting time for the display of analytical results at a round destination, as described in Example 14, the controller of the FPD 102 of the radiographic image capturing system 100 according to Example 17 has a difference calculating means for calculating a difference between frames, as shown in FIG. 19. The difference calculating means can send the acquired differential data to the medical cart 101.

The console 4 processes the differential data from the FPD 102 to generate dynamic image data and display a dynamic image based on the generated dynamic image data on the display 41.

The image analyzing apparatus 103 (or the image analyzer 7) analyzes the dynamic image data generated from the differential data from the console 4 to generate analytical result data and display an analyzed result image based on the analytical result data on the display unit.

The differential data between adjacent frames can reduce the data volume by, for example, converting two-byte data into one-byte data.

A dynamic image and an analyzed result image based on such differential data can be used for diagnosis by medical doctors or determination of re-capturing, because such an image can identify outlines, just as a dynamic image and an analyzed result image based on the original frame image data.

This configuration can increase a transfer rate between the FPD 102 and the medical cart 101 or between the medical cart 101 and the image analyzing apparatus 103 and speed up the analysis performed by the image analyzing apparatus 103.

<Countermeasures Against Heat>

Example 18

The FPD 102, which can capture both still images and serial images, cannot perform capturing when the temperature in the FPD 102 exceeds a certain level. In that case, the user has to stop the use of the FPD 102 and waits for a decrease in temperature to a predetermined level.

Figure 20:
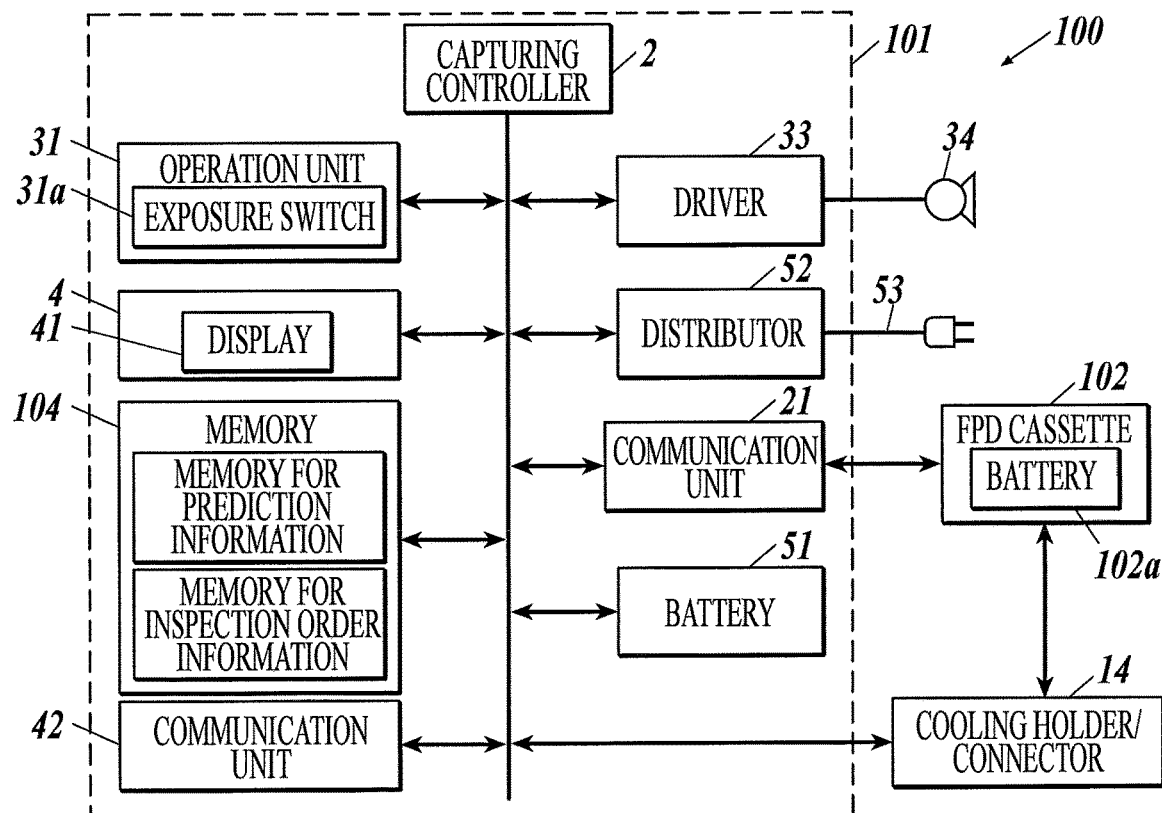
FIG. 20 is a block diagram illustrating a configuration of a radiographic image capturing system according to Example 18 of the first to third embodiments.

With reference to FIG. 20, the radiographic image capturing system 100 according to Example 18 can accommodate the FPD 102 in the medical cart 101 and includes an FPD holder 14 capable of cooling the accommodated FPD.

The FPD holder 14 includes a terminal connected to the distributor 52 of the medical cart 101 and plugged into the connector in the FPD 102 when the FPD 102 is accommodated. When this terminal is plugged into the connector in the FPD 102, the FPD 102 is charged with power from the battery 51 in the medical cart 101.

This configuration enables concurrent cooling and charging of the FPD 102 accommodated in the FPD holder between the capturing operations. This can prevent suspension of the capturing operations due to the dead battery or a rise in temperature of the FPD 102.

Example 19

To solve the problem of the temperature rise in the FPD 102, as described in Example 18, the radiographic image capturing system 100 according to Example 19 allows the FPD holder similar to that in Example 18 to be removed from the medical cart 101, while the FPD holder is left connected to the medical cart 101 via a cable.

Figure 21:
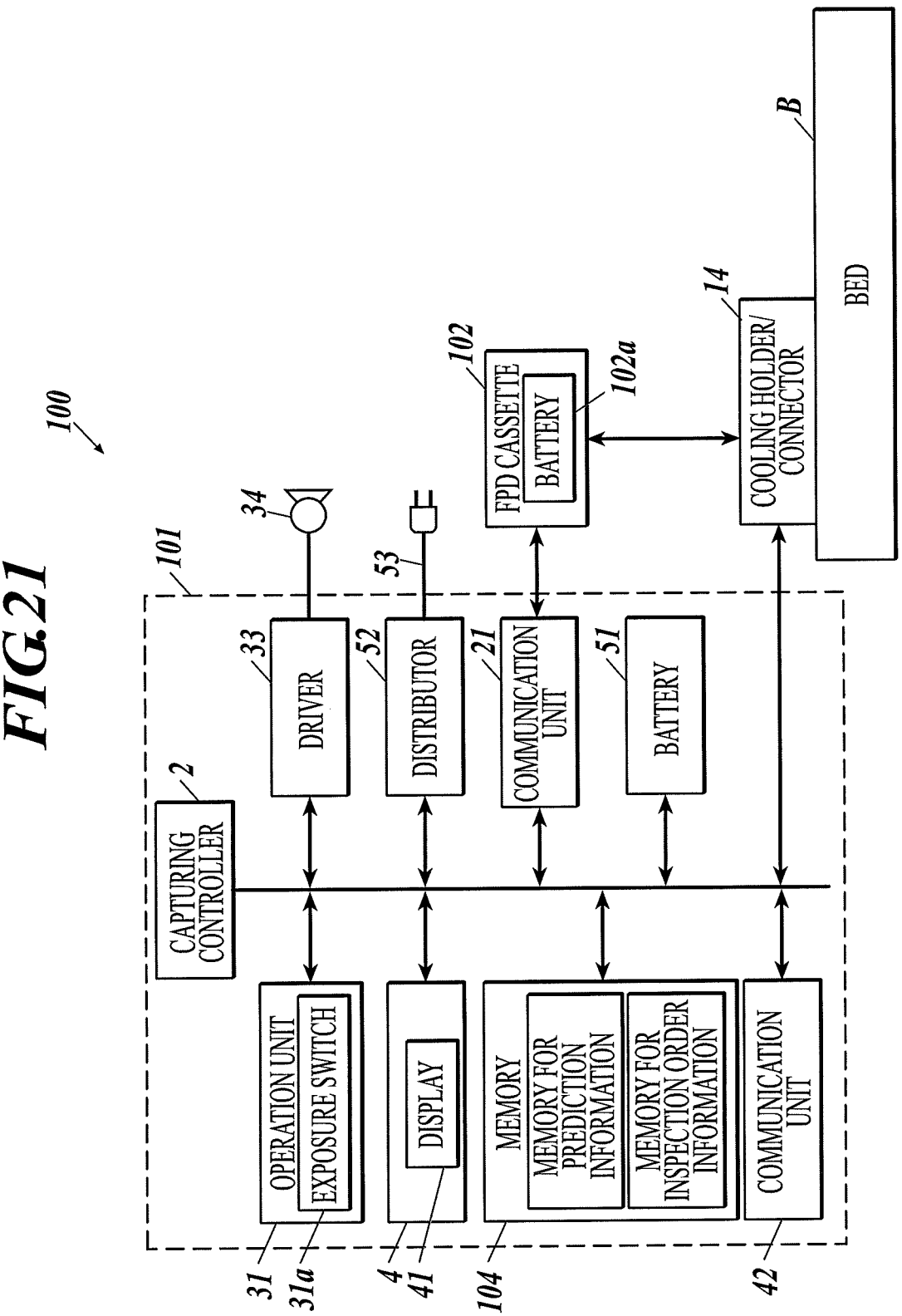
FIG. 21 is a block diagram illustrating a configuration of a radiographic image capturing system according to Example 19 of the first to third embodiments.

This configuration allows the FPD holder 14 to be used on, for example, a bed B, as shown in FIG. 21. The FPD 102 is accommodated in the FPD holder 14 on the bed B and a subject is laid on the FPD holder 14. This allows the capturing operation to be performed while the FPD 102 is cooled and charged. Continued capturing operations do not cause the dead battery or raise the temperature, thus preventing the suspension of the capturing operations for this reason.

Example 20

To solve the problem of the temperature rise in the FPD 102, as described in Example 18, the radiographic image capturing system 100 according to Example 20 includes a thermal sensor in the FPD 102.

The FPD 102 notifies the console 4 of its own temperature.

The console 4 stores image samples corresponding to capturing temperatures.

Variations in the quality of the image data received from the FPD 102, such as offset, image defects, and uneven gains, may occur due to heat or continued operations. The console corrects such variations based on the temperature information of the FPD 102, which is received together with the image data at the time of the capturing cycles, and the image samples.

This configuration allows image data to be properly corrected despite variations in the temperature of the FPD 102 due to continued capturing operations.

Example 21

Figure 22:
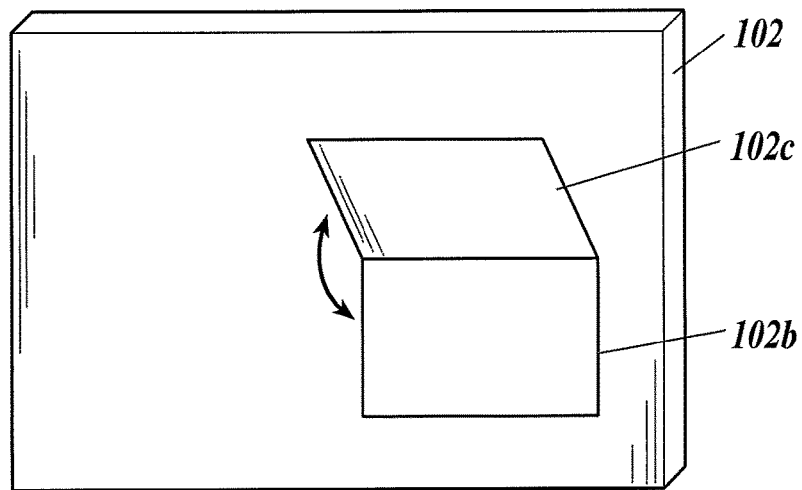
FIG. 22 is a perspective view of a radiographic image capturing system according to Example 21 of the first to third embodiments.

To solve the problem of the temperature rise in the FPD 102, as described in Example 17, the FPD 102 of the radiographic image capturing system according to Example 21 includes an opening 102b in the housing, as shown in FIG. 22, to facilitate dissipation of the internal heat.

The opening 102b is provided with a door 102c. The door 102c is openable and includes a packing on the perimeter of the opening on the rear of the FPD 102. When the door 102c is closed, the opening 102b is blocked such that the waterproof performance equivalent to that of the housing without an opening is achieved.

This configuration can reduce the temperature in the FPD 102 by opening the door 102c of the FPD 102 while the capturing operation is not performed, preventing the suspension of the capturing operation due to a rise in temperature.

Example 22

The temperature in the FPD 102 capable of serial capturing operations must be higher than a certain level before dynamic images of adequate quality can be produced. Unfortunately, the FPD temperature is so low that the serial capturing operations may result in several initial frame images having inadequate quality at the first capturing cycle.

Figure 23:
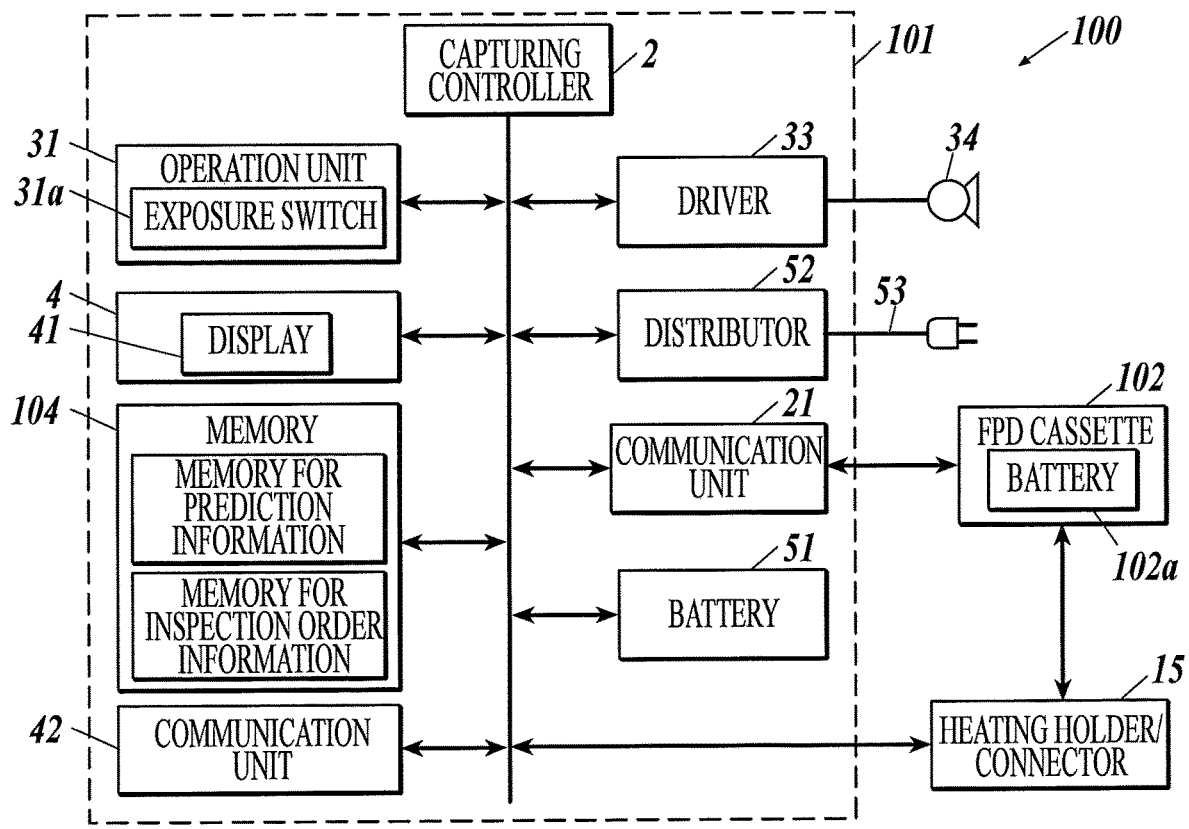
FIG. 23 is a block diagram illustrating a configuration of a radiographic image capturing system according to Example 22 of the first to third embodiments.

The radiographic image capturing system 100 according to Example 22 includes the FPD 102 accommodated in the medical cart 101 and the FPD holder 15 that can heat the accommodated FPD 102, as shown in FIG. 23.

The FPD holder 15 includes a terminal connected to the distributor 52 of the medical cart 101 and plugged into the connector in the FPD 102 after the FPD 102 is accommodated. After this terminal is plugged into the connector in the FPD 102, the FPD 102 is charged with power from the battery 51 in the medical cart 101.

This configuration allows the first frame images to have adequate quality even at the first capturing cycle.

Figure 24:
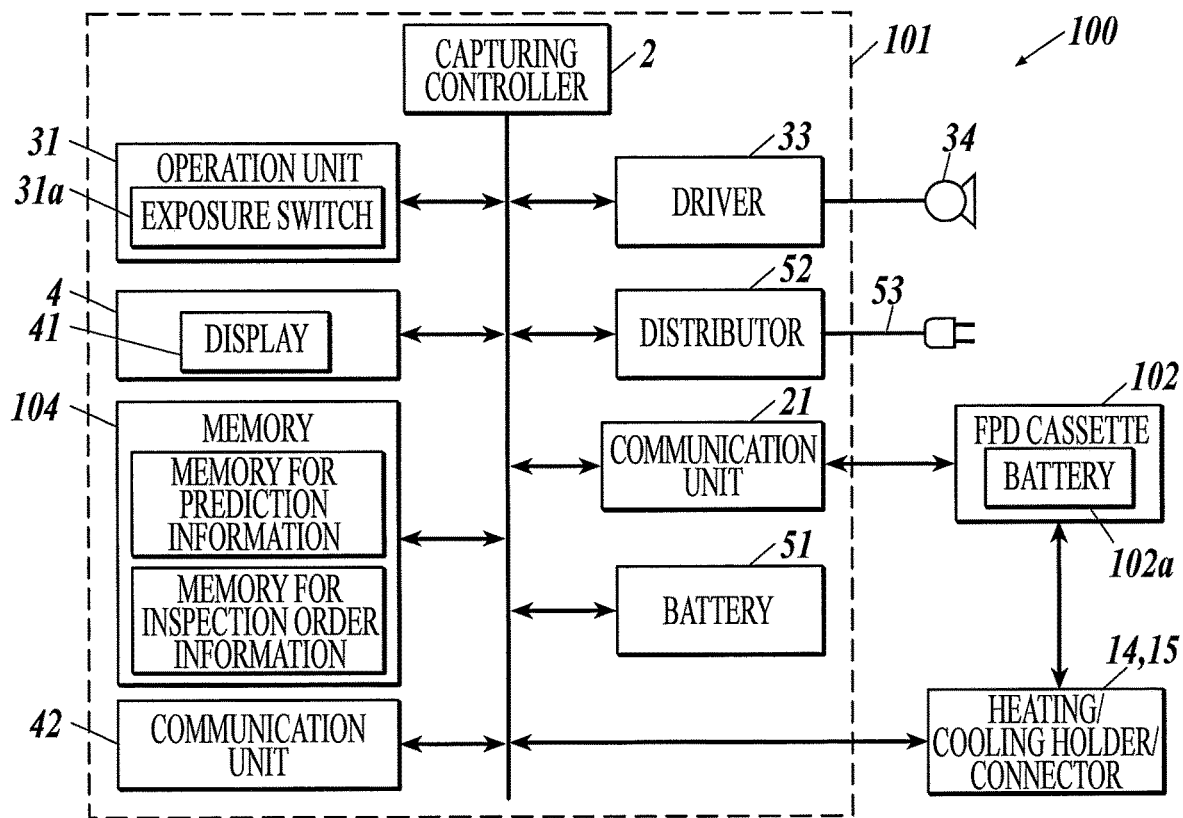
FIG. 24 is a block diagram illustrating a configuration of a radiographic image capturing system according to a variation of Example 22 of the first to third embodiments.

With reference to FIG. 24, the FPD holder 15 in the medical cart 101 according to Example 22 may be provided with the cooling function as described in Example 18. Such an FPD holder may have a configuration similar to that of, for example, a storage unit having both heating and cooling functions.

Alternatively, the FPD holder 14 having the cooling function may be provided separately from the FPD holder 15 having the heating function.

Example 23

To solve the problem of the temperature rise in the FPD 102, as described in Example 18, the radiographic image capturing system 100 according to Example 23 includes several FPDs 102, for example, two FPDs 102.

The medical cart 101 automatically switches between the FPD holders 14 and 15, described in the above-mentioned Examples, when the FPD 102 is put in one of the FPD holders 14 and 15.

This allows a single medical cart 101 to include two or more FPDs 102. If a first FPD 102 is no longer usable after serial capturing operations because of a high temperature, a second FPD 102 can be used in place of the first FPD 102. The first FPD 102 is cooled down during capturing operations with the second FPD 102 and becomes usable again. Several FPDs 102 in turn enable continuous capturing operations.

Example 24

To solve the problem of the temperature rise in the FPD 102, as described in Example 18, the FPD 102 of the radiographic image capturing system 100 according to Example 24 includes a thermal sensor.

The FPD 102 includes a table having capturing modes (still-image capturing and serial capturing operations) and the corresponding allowable capturing temperatures. For the serial capturing operations, different allowable temperatures may be set for the different numbers of captured images.

In response to setting of a capturing mode, the FPD 102 references the table and determines whether the FPD 102 temperature detected by the thermal sensor is allowable for the set capturing mode.

The FPD 102 also displays the results of the determination. In detail, the FPD 102 changes the lighting state of its indicator or sends the results to the medical cart 101 to display them on the display 41 of the console 4.

This configuration can reduce the waiting time for the capturing operation that has been suspended due to a rise in temperature in the FPD 102 to be resumed.

Example 25

To solve the problem of the temperature rise in the FPD 102, as described in Example 18, the radiographic image capturing system 100 according to Example 25 takes differences between captured images that require no consideration of offset variations to display dynamic images or analyze the dynamic state.

The radiographic image capturing system 100 displays and controls thermal capturing conditions for still images separately from those for dynamic images.

This eliminates the necessity for offset correction for serial capturing operations.

<Consecutive Capturing and Reduction in Radiation Dose>

Example 26

The consecutive emission of radiation rays for serial capturing operations raises a problem of radiation scattering to the surrounding environment.

Figure 25:
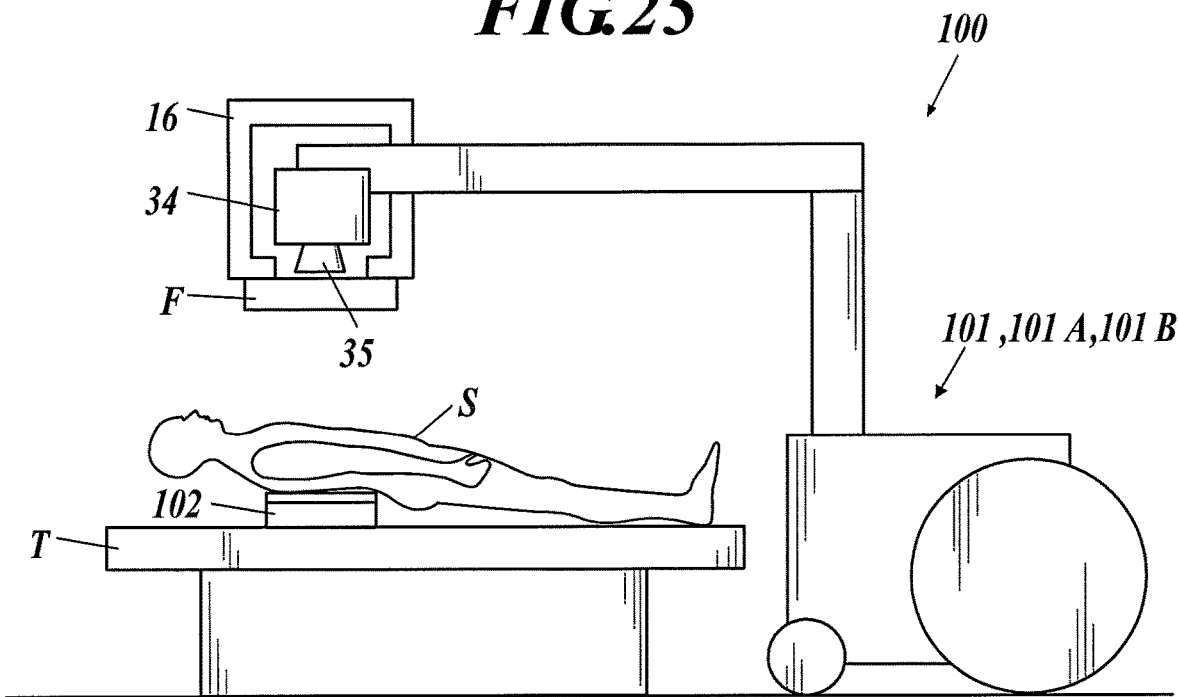
FIG. 25 is a side view of a radiographic image capturing system according to Example 26 of the first to third embodiments.

With reference to FIG. 25, the radiation source 34, excluding the irradiation port and the collimator 35 mounted on the irradiation port, of the radiographic image capturing system 100 according to Example 26 is covered with a box-shaped shield 16 composed of a material that shields radiation, such as lead.

This reduces radiation scattering to the surrounding environment from the radiation source 34 to produce clear captured images less affected by the scattering radiation.

<Difference in Operating Environments and Impact on Disturbing Noises>

Example 27

The medical cart 101 capable of serial capturing operations and capturing operations using the FPD 102 involves the risk of a captured image containing artifact due to the impact of a capturing environment, such as disturbing noises. Such a risk should be reduced.

The radiographic image capturing system 100 according to Example 27 monitors any noise in the surrounding environment during serial capturing operations.

If a disturbing noise is found during the serial capturing operations, the FPD 102 corrects the generated image data to remove the impact of the disturbing noise or prompts the user to stop the capturing operation.

This can reduce the risk of artifact.

Example 28

Figure 26:
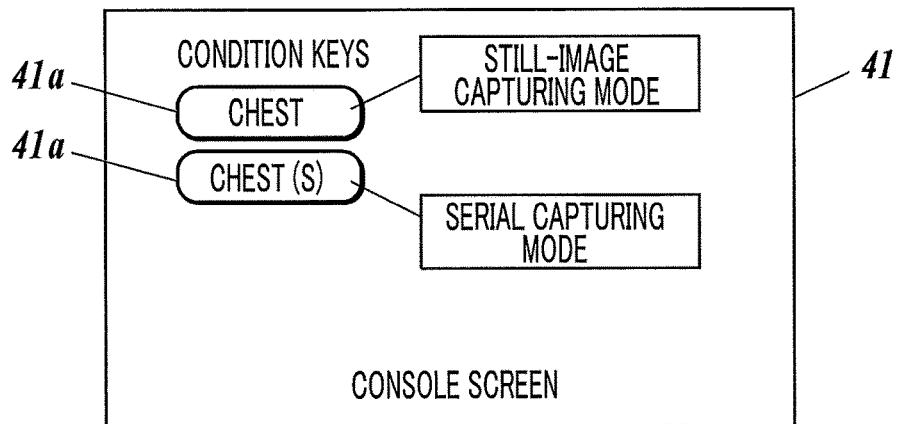
FIG. 26 illustrates an exemplary display on a display of a radiographic image capturing system according to Example 28 of the first to third embodiments.

To reduce the risk of artifact in a capturing environment, as described in Example 27, the radiographic image capturing system 100 according to Example 28 can display, for example, a screen for selecting a capturing condition on the display 41 of the console 4, as shown in FIG. 26. The screen displays multiple capturing condition keys 41a.

Each capturing condition key 41a has a corresponding target site and a corresponding capturing mode (still-image capturing or serial capturing operations). Touching a capturing condition key 41a of "chest(S)" gets the medical cart 101 and the FPD 102 ready for serial capturing operations of the chest.

Selection of a capturing condition key correlates the key with still-image capturing or serial capturing operations to clarify capturing conditions. This can trigger the function to correct the image quality or reduce the impact of disturbance.

Example 29

To reduce the risk of artifact in a capturing environment, as described in Example 27, the radiographic image capturing system 100 according to Example 29 includes a length-measuring sensor in at least one of the FPD 102 and the radiation source 34. The length-measuring sensor measures a distance (SID) between the FPD 102 and the radiation source 34 and sends the results of the measurement to the console 4.

The console 4 contains a predetermined threshold and compares the distance sent from the length-measuring sensor with the threshold. If the distance is greater than the threshold, the console 4 gets the radiographic image capturing system ready for a general capturing operation; if the distance is equal to or less than the threshold, the console 4 gets the radiographic image capturing system ready for a round capturing operation.

In general, SIDs for general capturing are larger in many cases. Specification of a threshold between typical SIDs for general capturing and those for round capturing enables the above mentioned control.

<Switching Synchronization Signals>

Example 30

In the serial capturing operations involving emission of pulsed radiation rays multiple times, the FPD 102 should accumulate electric charges in accurate synchronization with the emission of pulsed radiation rays from the radiation emitting apparatus 3.

Figure 27:
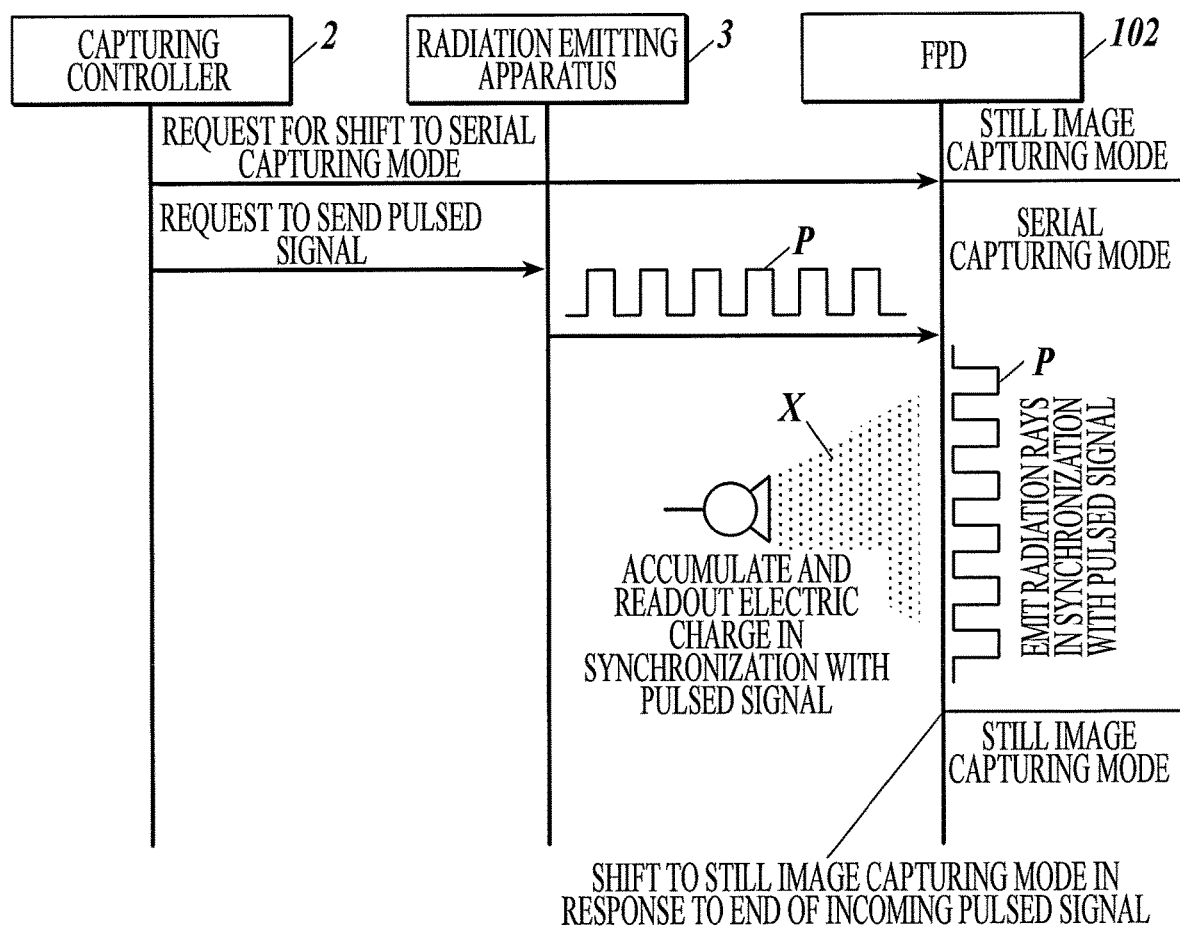
FIG. 27 is a ladder chart illustrating an operation of a radiographic image capturing system according to Example 30 of the first to third embodiments.

When the radiation emitting apparatus 3 receives a signal from the capturing controller 2 instructing the radiation emitting apparatus 3 to send a pulsed signal, as shown in FIG. 27, the radiographic image capturing system 100 according to Example 30 generates pulsed radiation rays X at a predetermined cycle and sends a pulsed signal P to the FPD 102 in synchronization with the radiation.

When the FPD 102 in the still-image capturing mode receives a signal from the capturing controller 2 instructing the FPD 102 to shift the capturing mode to a serial capturing mode, the FPD 102 shifts the capturing mode to the serial capturing mode.

When the FPD 102 in the serial capturing mode detects no incoming pulsed signal P from the radiation emitting apparatus 3, the FPD 102 restores to the still-image capturing mode.

Use of pulsed signals P in synchronization with emissions of pulsed radiation rays allows the FPD 102 to generate frame image data in accurate synchronization with the emission of pulsed radiation rays from the radiation emitting apparatus 3.

When the FPD 102 receives a signal from the capturing controller 2 instructing the FPD 102 to shift the capturing mode to serial capturing mode, the FPD 102 generates a pulsed signal P and sends the generated pulsed signal P to the radiation emitting apparatus 3. This allows the FPD 102 to receive pulsed radiation rays X from the radiation emitting apparatus 3 in accurate synchronization with its own electric charge accumulation state.

<Method for Starting Capturing>

Example 31

During the serial capturing cycle, the width of a pulsed signal sent to the FPD 102 instructing the FPD 102 to read a signal value is varied between pre- and post-emission of radiation rays. Use of different pulse widths between pre- and post-emission allows the FPD 102 to recognize the emission of radiation. Such a function can be readily incorporated in the radiographic image capturing system if the FPD 102 (a receiver of pulsed signals) and the radiation emitting apparatus 3 (a transmitter) are developed concurrently or by the same manufacturer. Unfortunately, if the development of one of these devices has been finished or these devices have been developed by different manufactures, one of these devices should be modified in line with the other, resulting in a high development cost.

The FPD 102 of the radiographic image capturing system 100 according to Example 31 is equipped with a radiation sensor detecting the emission of radiation rays.

The radiation sensor detects the start of the emission of radiation rays, while the FPD 102 receives synchronization signals from the medical cart 101 consecutively and repeats a cycle of accumulation and readout of electric charges.

This configuration allows the FPD 102 to recognize the emission of radiation rays without providing the radiation emitting apparatus 3 with a function to vary the pulse width of radiation rays, thus reducing the development cost.

Example 32

To address the problem of high development cost of varying the pulse width of radiation rays, as described in Example 31, the FPD 102 of the radiographic image capturing system 100 according to Example 32 has a function to calculate the presumed radiation dose. More specifically, the FPD 102 calculates the presumed dose of emitted radiation rays based on the signal values of generated frame images, while the FPD 102 receives synchronization signals from the medical cart 101 consecutively and repeats a cycle of accumulation and readout of electric charges.

The FPD 102 compares the calculated presumed radiation dose with a pre-stored threshold. If the presumed radiation dose is equal to or higher than the threshold, the emission of radiation rays is deemed to have been performed.

This configuration allows the FPD 102 to recognize the emission of radiation rays without providing the radiation emitting apparatus 3 capable of varying the pulse width of radiation rays, thus reducing the development cost.

<Termination of Capturing Operations>

Example 33

Some radiation emitting apparatuses emitting pulsed radiation rays several times for a predetermined term in response to one-time press of the exposure switch may stop emission of radiation rays immediately after release of the exposure switch during emission. In this case, a reduction in the dose of the last pulsed radiation operation results in only the last frame image having a different density. To address this problem, the radiation emitting apparatus 3 needs to be altered so that the emission of radiation rays does not stop immediately or replaced with another radiation emitting apparatus that does not stop emission of radiation rays immediately. Unfortunately, the alternation cost is high and the replacement cost is higher than the alternation cost since such a radiation emitting apparatus is expensive.

Figure 28:
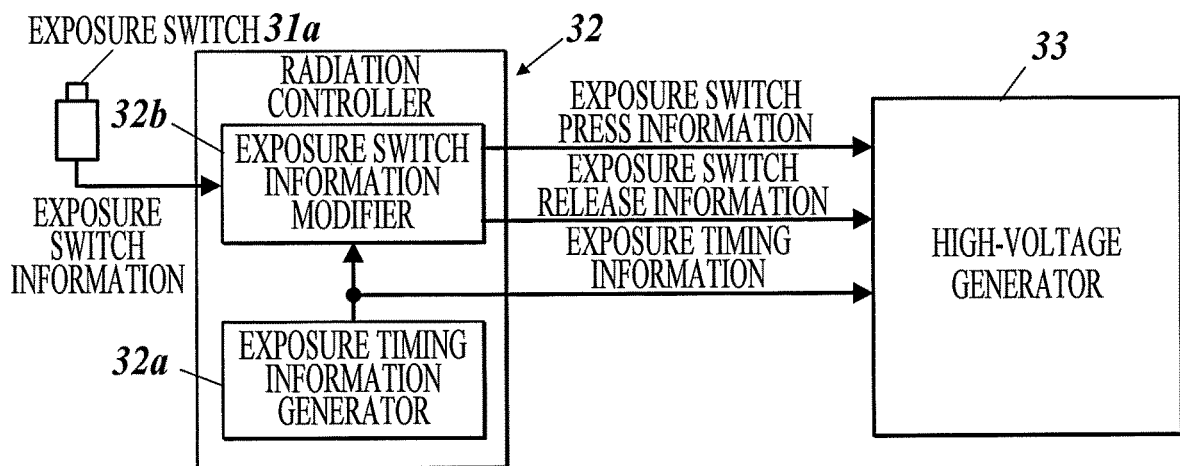
FIG. 28 is a block diagram illustrating a configuration of a radiation emitting apparatus in a radiographic image capturing system according to Example 33 of the first to third embodiments.

With reference to FIG. 28, the radiation controller 32 according to Example 33 includes an exposure timing information generator 32a and an exposure switch information modifier 32b.

The exposure timing information generator 32a sends exposure timing information to the high-voltage generator 33 and the exposure switch information modifier 32b. The exposure timing information is a pulsed signal repeatedly output at the same timing as a predetermined timing for emission of radiation rays. The high-voltage generator 33 and the radiation source 34 generate pulsed radiation rays based on the exposure timing information.

The exposure switch information modifier 32b can receive the exposure switch information from the exposure switch 31a. Upon detection of press of the exposure switch 31a, the exposure switch information modifier 32b sends the exposure switch press information to the high-voltage generator 33. Upon detection of release of the exposure switch 31a, the exposure switch information modifier 32b sends the exposure switch release information to the high-voltage generator 33.

Upon detection of release of the exposure switch 31a while a pulsed signal (exposure timing information) is at a high level, the exposure switch information modifier 32b does not send the exposure switch release information to the high-voltage generator 33 immediately and waits for the pulsed signal to vary from the high to low level before the exposure switch release information is sent.

This configuration ensures that the emission of radiation rays continues for a predetermined pulse width, despite the release of the exposure switch 31a during the emission of pulsed radiation rays, to prevent generation of a frame image with an inadequate radiation dose.

In other words, this configuration ensures that frame images are generated with an adequate radiation dose until the last one, without significantly altering or replacing the radiation emitting apparatus 3 that stops emission of radiation rays immediately in response to the release of the exposure switch even during emission.

Figure 29:
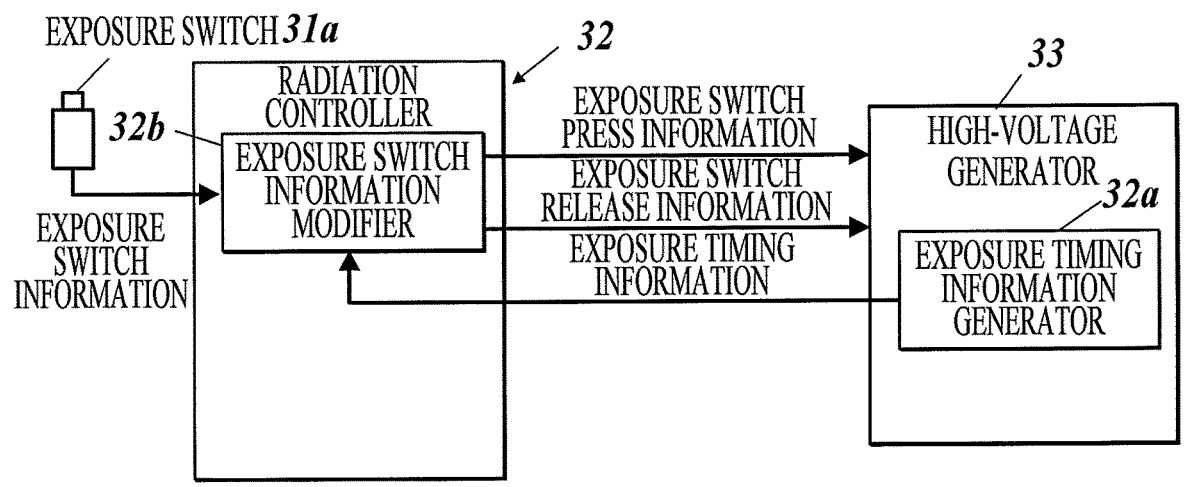
FIG. 29 is a block diagram illustrating a configuration of a radiation emitting apparatus according to a variation of Example 33 of the first to third embodiments.

The exposure timing information generator 32a may be included in the high-voltage generator 33, as shown in FIG. 29.

Example 34

In serial capturing operations with a radiation emitting apparatus that immediately stops emission of radiation rays in response to the release of the exposure switch even during emission, a reduction in the dose of the last pulsed radiation results in only the last frame image having a different density. The user needs to check the frame image captured last to determine the usability for diagnosis. Checking whether or not the last frame image is generated with adequate radiation dose at each capturing operation requires additional work.

Figure 30:
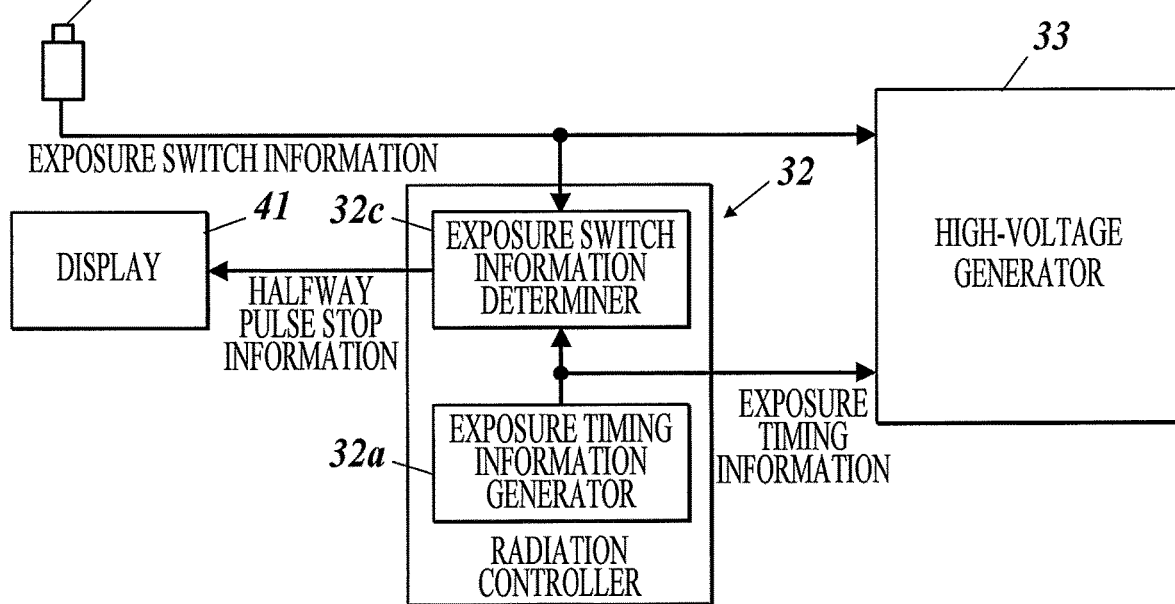
FIG. 30 is a block diagram illustrating a configuration of a radiation emitting apparatus in a radiographic image capturing system according to Example 34 of the first to third embodiments.

With reference to FIG. 30, the radiation emitting apparatus 3 according to Example 34 includes an exposure timing information generator 32a and an exposure switch information determiner 32c.

The exposure timing information generator 32a, which has the same configuration as that of Example 33, sends exposure timing information to the high-voltage generator 33 and the exposure switch information determiner 32c.

The exposure switch information determiner 32c can receive the exposure switch information from the exposure switch 31a. Upon detection of release of the exposure switch 31a while a pulsed signal (exposure timing information) is at a high level, the exposure switch 31a sends halfway pulse stop information to the display 41 of the console. The halfway pulse stop information indicates that the exposure switch 31a has been released in the middle of the emission of radiation rays.

Based on the content of the received halfway pulse stop information, the display 41 displays a message indicating that the exposure switch 31a has been released in the middle of the capturing operation of the last frame image.

If the message indicating that the exposure switch 31a has been released in the middle of the last frame image is not displayed on the display 41, the user needs to check the last frame image; otherwise, the user needs to check the last frame image but one, resulting in saving the trouble of the user to check the image.

Figure 31:
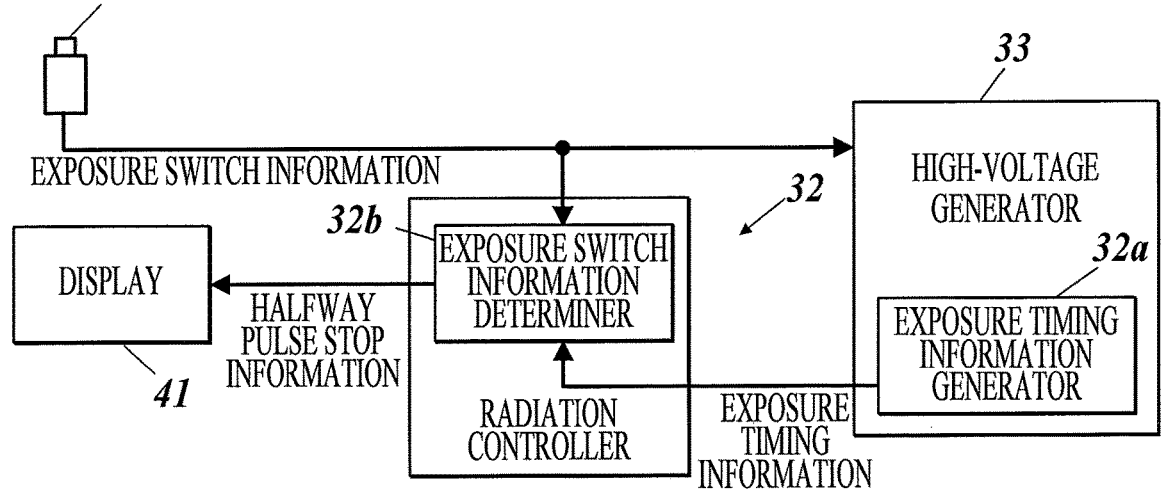
FIG. 31 is a block diagram illustrating a configuration of a radiation emitting apparatus according to a variation according to Example 34 of the first to third embodiments.

Alternatively, the exposure timing information generator 32a may be provided in the high-voltage generator 33, as shown in FIG. 31.

A message indicating that the exposure switch 31a has not been released in the middle of the last frame image may be displayed on the display 41 in place of the message indicating that the exposure switch 31a has been released in the middle of the last frame image. Alternatively, the user may select any one of the messages to be displayed. Adoption of an intuitive message can prevent misrecognition by the user.

Alternatively, a message indicating that the exposure switch 31a has been released or not released in the middle of the last frame image may be displayed together with the captured image. This configuration allows the user, who normally checks the image after capturing operations, to concurrently check the captured image and for the occurrence of a stop of emission in the middle of the last pulse. This can reduce the number of operations and the number of movements of the line of sight, enhancing the usability.

Alternatively, the halfway pulse stop information may be stored in association with a captured dynamic image and the dynamic image when played back may be displayed together with a message indicating that the exposure switch 31a has been released or not released in the middle of the last frame image.

Alternatively, when the captured dynamic image is sent to PACS or a workstation, the halfway pulse stop information may be sent together. This can prevent lack of attention to the last frame image when a stored dynamic image is played back, an image stored in PACS is displayed, or image processing is performed at a workstation.

In response to information indicating that emission has stopped or has not stopped in the middle of the last pulse, the console 4 may delete the last frame of the captured image in the case where emission has stopped in the middle of the last pulse. In addition, the deleting function may be enabled or disabled by the user. This configuration saves the trouble of the user because the last frame image generated with an inadequate radiation dose is automatically deleted in the case where the deleting function is enabled.

Example 35

As described in Example 34, the radiation emitting apparatus that stops emission of radiation rays in the middle in response to the release of the exposure switch requires additional work of checking whether the last frame image has been generated with an adequate radiation dose. To cope with this problem, the console 4 of the radiographic image capturing system 100 according to Example 35 includes a last frame density processing means for measuring the density of the last frame image of a captured dynamic image.

The console 4 also includes a means for calculating a density index value based on the densities of the frame images other than the last.

The console 4 determines whether a difference between the density measured in the last frame image and the density index value calculated based on the densities of other frame images exceeds a predetermined threshold.

If the difference exceeds the threshold, the console 4 displays that effect on the display 41.

Figure 32:
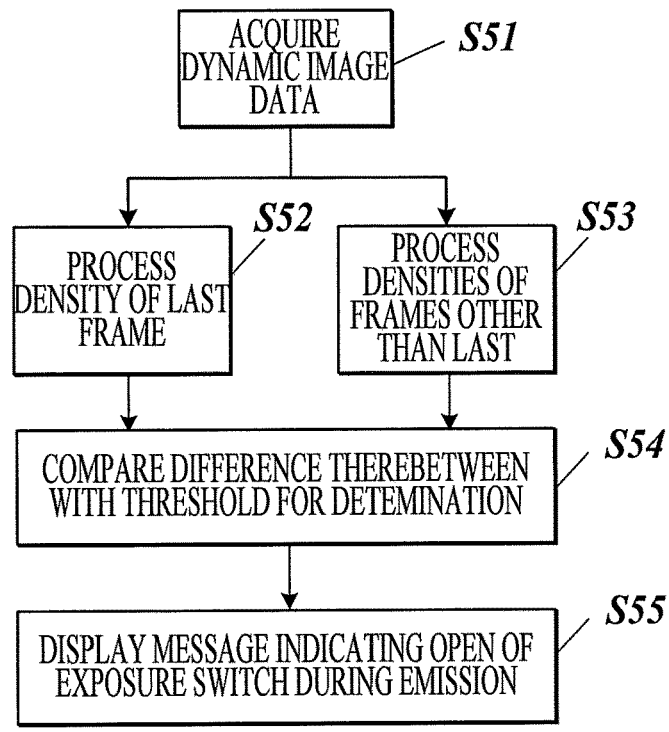
FIG. 32 is a flow chart of a control process of a radiographic image capturing system according to Example 35 of the first to third embodiments.

With reference to FIG. 32, the radiographic image capturing system 100 according to Example 35 provided with the console 4 acquires dynamic image data (Step S51). The radiographic image capturing system 100 acquires the density of the last frame image (Step S52) and calculates the density index value based on the densities of other frame images (Step S53). In FIG. 32, Step S52 and Step S53 are performed in parallel. Alternatively, one of Step S52 and Step S53 may be performed first.

After the density and the density index value are determined, the radiographic image capturing system 100 takes a difference therebetween and compares the difference with a predetermined threshold (Step S54).

If the difference is greater than the threshold at Step S54, then a message indicating that the exposure switch 31a has been released in the middle of the last frame image is displayed on the display 41 (Step S55).

If the difference is equal to or less than the threshold at Step S54, the message indicating so or no message may be displayed.

If the message indicating that the exposure switch 31a has been released in the middle of the last frame image is not displayed on the display 41, the user needs to check the last frame image, otherwise, the user needs to check the frame image one frame before the last frame image, resulting in saving the trouble of the user to check the image.

The density of the frame image one frame before the last frame image may be used as a density index value. Alternatively, the average, weighted average, median, maximum, or minimum value of a predetermined number of frame images going back from the frame image one frame before the last frame image may be used as a density index value.

The results determined through comparison with the threshold may be displayed on the display 41.

If the radiation dose for the last frame image is determined to be inadequate, the last frame may be deleted. In addition, the deleting function may be enabled or disabled by the user.

This configuration saves the trouble of the user because the last frame image generated with an inadequate radiation dose is automatically deleted if the deleting function is enabled.

Example 36

If the user determines that the dynamic image captured during a round is unsuitable for diagnosis, re-capturing operations are needed.

Unfortunately, the process of a dynamic image captured during a round at the console 4 in the medical cart 101 takes much time because the console 4 has a limited image processing capacity. This may force the subject in a capturing mode to wait until the user determines whether the dynamic image is suitable for diagnosis.

Figure 33:
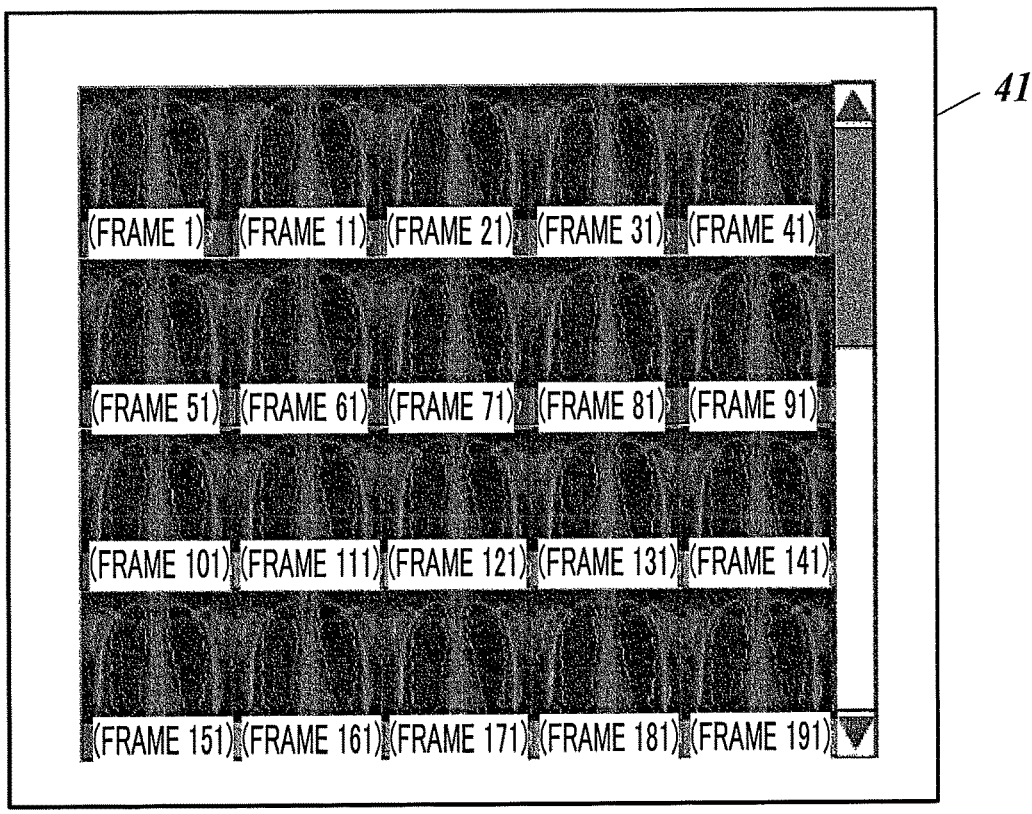
FIG. 33 illustrates an exemplary display on a display of a radiographic image capturing system according to Example 36 of the first to third embodiments.

To cope with this problem, the console 4 according to Example 36 extracts the frame images of a dynamic image from the start of a capturing operation up to the present at predetermined intervals (for example, every ten frames in FIG. 33) and sorts and displays the extracted frame images sequentially in rows, as shown in FIG. 33.

If all the frame images cannot be displayed on the display 41, the user may scroll the screen with the mouse wheel to change frame images displayed.

This allows the user to view frames in succession, check whether any body motion of the subject has adversely affected the capturing operation, and determine the necessity for a re-capturing operation.

In addition, captured frame images are decimated for verification. This allows the user to verify the captured frame images in a shorter time than the actual capturing time.

Example 37

If adequate quality cannot be achieved during capturing operations of a radiographic image, re-capturing operations may be performed. In the case of serial capturing operations, re-capturing operations must start from the beginning. This increases the number of useless images, prolongs the inspection time, and increases the exposure time of a subject to radiation rays, making the user to hesitate to decide re-capturing operations.

To cope with this problem, the console 4 of the radiographic image capturing system 100 according to Example 37 is connectable to an automated voice system or electrocardiograph. This configuration allows the console 4 to receive respiration instructions from the automated voice system and timing information, such as on heartbeats, from the electrocardiograph during serial capturing operations.

The console 4 stores the phase of respiration or heartbeat at which the serial capturing operation is suspended based on the timing information received at the suspension of the serial capturing operation. The phase information takes the form of additional information at a failed capturing operation.

This allows a re-capturing operation to be started at the respiration or heartbeat phase stored in the form of additional information after the suspension of the serial capturing operation. Of the frame images of a dynamic image (or analytical results) acquired in the previous capturing operation, only those for a minimal period after the suspension are acquired through the re-capturing operation. The frame images that were captured after the suspension (i.e., failed frame images) are replaced with these new re-captured frame images to generate a dynamic image equivalent to that originally intended. This re-capturing operation can reduce the number of useless frame images, facilitating the decision of the user to perform re-capturing operations even for serial capturing operations.

Example 38

In the case of serial capturing operations, the user hesitates to decide re-capturing operations since they produce a large number of useless images, as described in Example 37. To cope with this problem, the radiographic image capturing system 100 according to Example 38 includes a transparent observation window made of glass or acrylic resin. The radiographic image capturing system 100 acquires information on automatically detected body motions, the amount of motion of the subject (biological body information), such as the phases of respiration and heartbeat, and a dynamic image corresponding to the number of captured frame images from the console 4. The automatically detected body motions and the amount of motion of the subject (biological body information), such as the phases of respiration and heartbeat, are chronologically displayed on the subject viewed from the observation window. The radiographic image capturing system 100 also includes a projecting means for projecting information on a captured image. The projecting means may be portable or a projector capable of directly projecting information on a window glass of a radiation chamber or the subject.

This configuration allows the user to stop the serial capturing operation in the middle when it fails to reduce the radiation exposure of the subject.

Instructions to the subject or those to the user to start or stop exposure are displayed timely. This allows the user who reads these instructions to issue directions to the subject or perform exposure operations, eliminating the necessity for the automated voice system.

Example 39

In serial capturing operations, a large number of images must be verified before the user can determine the necessity for re-capturing operations. This extends inspection time and the subject needs to wait.

To cope with this problem, the console 4 of the radiographic image capturing apparatus according to Example 39 includes criteria for determining whether each frame image of a dynamic image is captured properly (capturing failure criteria). A capturing failure is determined using signals output from an accelerometer detecting body motions or displacement data. The displacement data is acquired through analysis of body motions of the subject from a subject image taken through serial capturing operations.

The console 4 evaluates various pieces of information acquired against the capturing failure criteria to determine whether the image is captured properly and displays the results of the determination on the display 41.

This helps the user play back and visually check frame images to reduce the time to determine the necessity for re-capturing operations.

Example 40

In serial capturing operations, the user must avoid an excessive cumulative exposure dose, unlike still-image capturing operations.

The radiographic image capturing system 100 according to Example 40 measures the dose of radiation emitted by the radiation source 34 or irradiated to the FPD 102.

The console 4 accumulates the dose of radiation emitted by the radiation source 34 or irradiated to the FPD 102 and determines whether the cumulative dose reaches a predetermined upper limit of the exposure dose.

When the cumulative dose of the radiation dose reaches the upper limit of the exposure dose, the console 4 automatically stops the serial capturing operations.

This ensures that the upper limit of the radiation exposure of the subject is not exceeded.

Example 41

In serial capturing operations, re-capturing operations are needed due to deterioration of quality of communication between the FPD 102 and the medical cart 101, in particular, in the ease of communication over a wireless network, while serial capturing is being performed.

The FPD 102 of the radiographic image capturing system 100 according to Example 41 determines whether the communication between the FPD 102 and the medical cart 101 is established at predetermined intervals (several seconds) during the serial capturing operations. The determination is performed by, for example, calculating a gap between timings of synchronization based on communication rate information. If the gap is not greater than a predetermined gap, the FPD 102 determines that the communication is established and can extend the serial capturing operation for a few seconds until the next communication check point.

If the communication check is successful, the FPD 102 and the radiation emitting apparatus 3 perform serial capturing operations in synchronization with the timings of image accumulation by the FPD 102 and emission by the radiation emitting apparatus 3.

This configuration allows serial capturing operations to be suspended while the quality of communication is deteriorating, reducing radiation exposure of the subject. In the case of serial capturing operations via a wireless network, in particular, capturing operations can be extended while the communication is established.

<Error Handling>

Example 42

Dynamic image data and analytical result data, which are also dynamic images in many cases, have a data volume significantly greater than still images, resulting in a longer time to transfer and analyze the image data.

To verify the results of the dynamic state analysis of a subject immediately after the capturing operation during rounds, the time to wait for the analytical results to be displayed, including the time to transfer and analyze the data, should be reduced.

Figure 34:
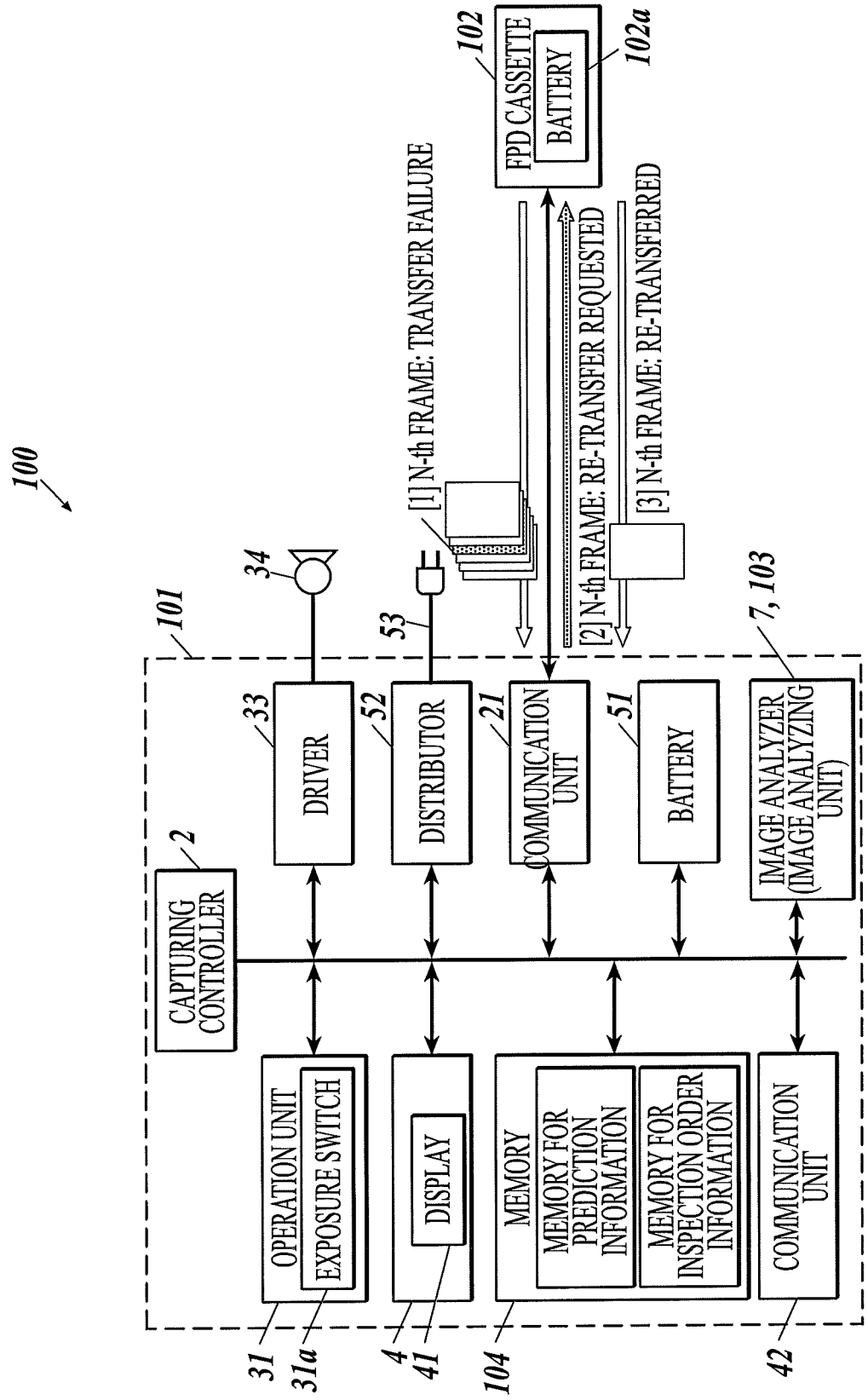
FIG. 34 is a block diagram illustrating a configuration of a radiographic image capturing system according to Example 42 of the first to third embodiments.

With reference to FIG. 34, the capturing controller 2 or the console 4 of the radiographic image capturing system 100 according to Example 42 checks dynamic image data received from the FPD 102. If any data transfer error is found, the capturing controller 2 or the console 4 requests the FPD 102 for bulk re-transfer of all the frame data or re-transfer of only frame data that resulted in an error in the previous transfer.

In detail, in the case where reliability of general data is low due to a poor network environment, bulk re-transfer is requested. In the case where transfer errors may have occurred in a limited period and thus affected data may be limited, retransfer of only relevant frame data is requested by specifying their frame numbers.

This configuration allows reliable dynamic image data to be restored in the shortest time.

<Emission Conditions>

Example 43

Some radiographic image capturing systems capable of capturing both still images and serial images cannot handle serial images in still-image capturing systems.

The console 4 of the radiographic image capturing system 100 according to Example 43 can acquire both still-image capturing orders and serial capturing orders and convert these orders into RIS codes under modality work list management (MWM).

Figure 35:
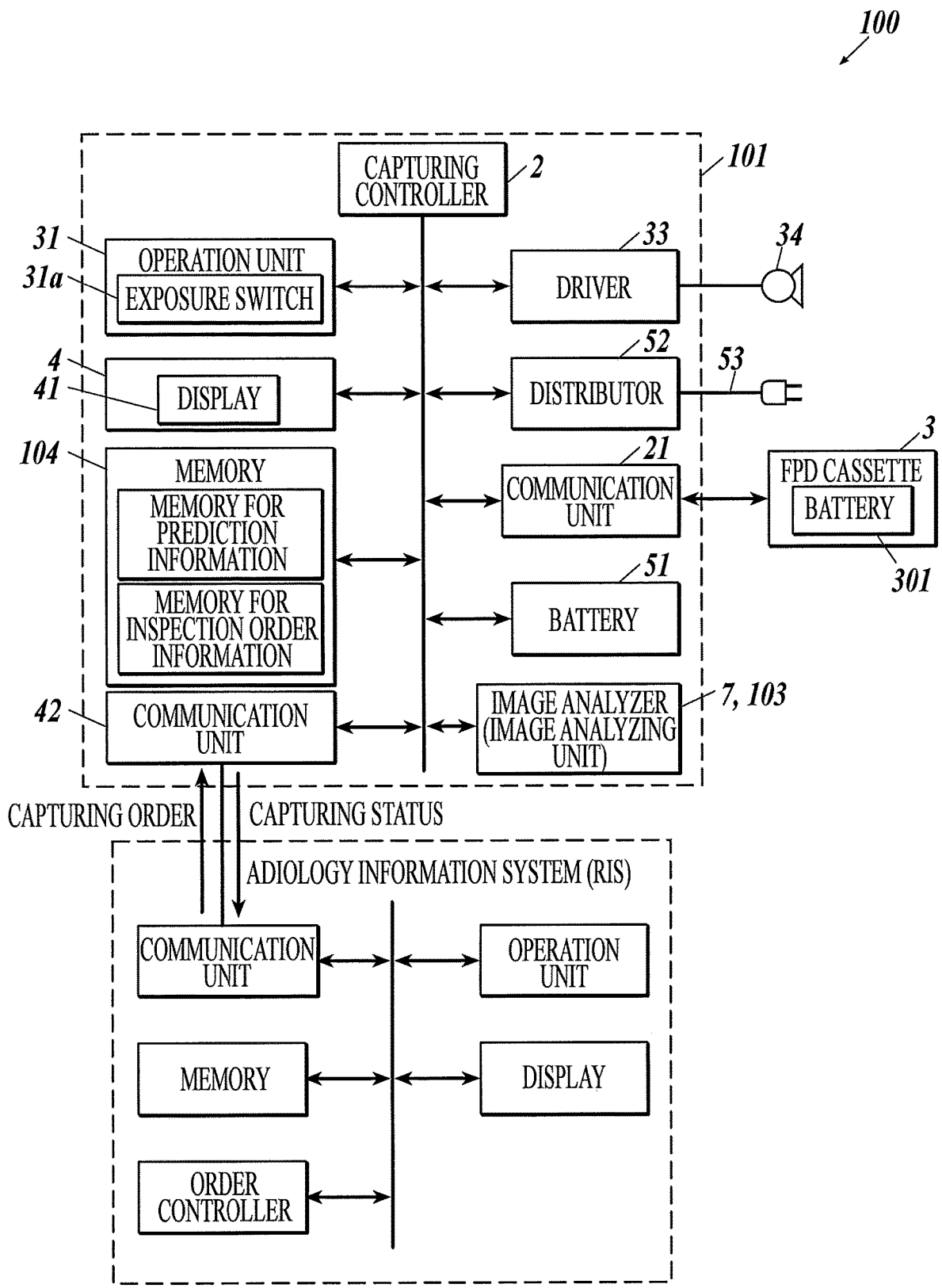
FIG. 35 is a block diagram illustrating a configuration of a radiographic image capturing system according to Example 43 of the first to third embodiments.

With reference to FIG. 35, the FPD 102 notifies an RIS server of the status of a serial capturing operation using the modality performed procedure step (MPPS), just as for a still-image capturing operation. The notification is provided in line with the progress of a capturing operation performed in response to a capturing order.

This allows an existing still-image capturing system to handle both still-image capturing orders and serial capturing orders and their result data through the same process, improving the efficiency of capturing operations.

Alternatively, all the internal image objects, additional settings, and information objects in the capturing controller 2 and the console 4 according to Example 43 may have a structure capable of handling dynamic images, i.e., performing both still-image capturing and serial capturing operations.

This allows a still image to be handled as a dynamic image consisting of a single frame image in the processes of image retrieval, order management, image processing, image display, and image adjustment to simplify the structure of a radiographic image capturing system. This leads to delivery of a high-quality radiographic image capturing system at a low price within a short term.

Figure 36:
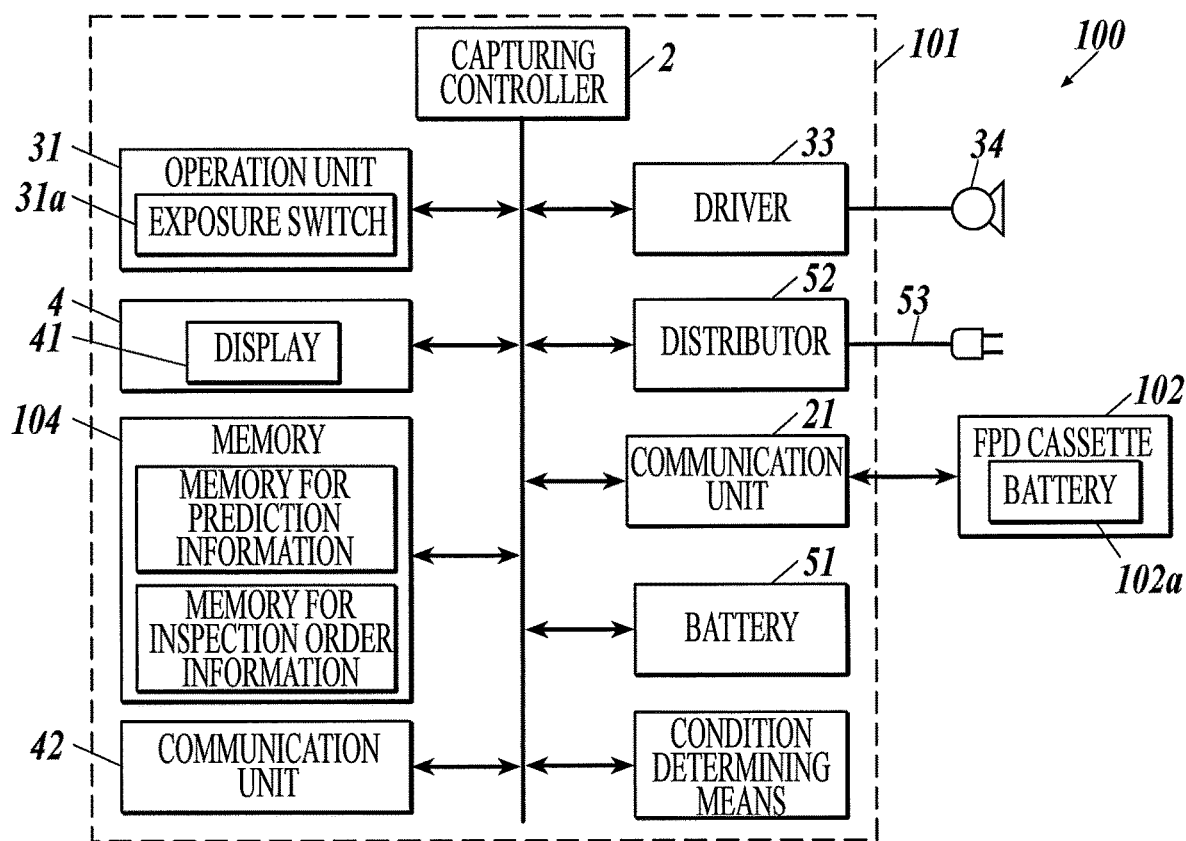
FIG. 36 is a block diagram illustrating a configuration of a radiographic image capturing system according to a variation of Example 43 of the first to third embodiments.

Alternatively, the capturing controller 2 and the console 4 of the radiographic image capturing system according to Example 43 may include a condition determining means, as shown in FIG. 36. The condition determining means determines emission conditions for consecutive capturing operations based on the results of still image capturing operations and sets the determined emission conditions in the radiation emitting apparatus 3.

This eliminates the necessity for scout capturing operations, which are required to determine emission conditions for serial capturing operations, leading to a reduction in radiation exposure.

Example 44

The serial capturing operations include those by continuous radiation and those by pulsed radiation. The former involves a continuous emission of radiation rays. The latter involves emission of pulsed radiation rays several times.

The serial capturing operations by pulsed radiation can reduce radiation exposure of a subject as compared with serial capturing operations by continuous radiation, but still tend to have a total radiation exposure greater than still-image capturing operations, which generate an image with a single exposure. Serial capturing operations face a challenge of how to avoid excess exposure. This is also important to prevent the emission of unnecessary radiation rays to the surrounding environment in capturing during a round using a medical ward.

The console 4 of the radiographic image capturing system 100 according to Example 44 can set the emission condition for static images within the upper limit of emission condition for dynamic images in the radiation emitting apparatus 3.

This can determine the upper limit of emission condition for serial capturing operations, preventing a subject from being accidentally exposed to excess radiation rays during serial capturing operations.

Example 45

To prevent a subject from being exposed to excess radiation rays during serial capturing operations, as described in Example 44, the radiation controller 32 of the radiographic image capturing system 100 according to Example 45 can determine the emission condition in the form of kV-mA·ms and kV-mAs for still-image capturing operations, while the radiation controller 32 prohibits the use of emission conditions in the form of kV-mAs for serial capturing operations.

This can ensure that the time consumed in a single emission operation of pulsed radiation rays is within electric charge accumulation time to reduce excess exposure, which cannot be controlled by the user as a normal exposure in proportion to the amount of electric charges accumulated.

Figure 37:
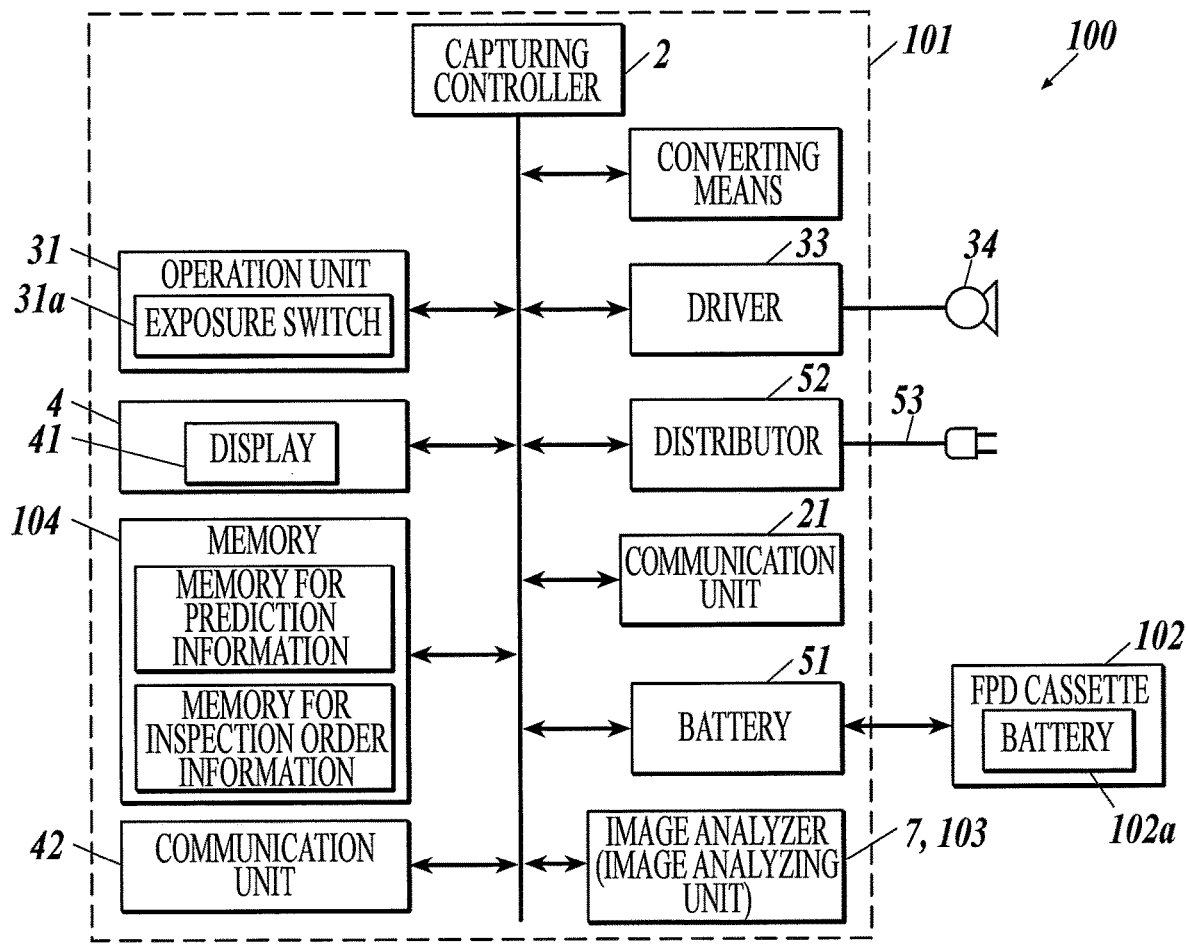
FIG. 37 is a block diagram illustrating a configuration of a radiographic image capturing system according to Example 45 of the first to third embodiments.

Alternatively, in the case where the emission conditions for serial-image capturing operations are set based on kV-mAs in Example 45, as shown in FIG. 37, the converting means may convert the emission conditions in the form of kV-mAs into those in the form of kV-mA·ms in the radiation emitting apparatus 3.

Conversion equations from kV-mAs to kV-mA·ms vary, depending on the type of radiation emitting apparatus. However, the above-mentioned configuration conceals differences in conversion equations during operations of the console 4, thus enhancing the convenience of the user.

Example 46

To prevent a subject from being exposed to excess radiation rays during serial capturing operations, as described in Example 44, the radiation emitting apparatus 3 of the radiographic image capturing system 100 according to Example 46 can determine still-image capturing conditions separately from serial-image capturing conditions and include an upper limit of the emission condition in the serial capturing conditions.

This can determine the upper limit of emission condition for serial capturing operations, preventing a subject from being accidentally exposed to excess radiation rays during serial capturing operations.

Example 47

To prevent a subject from being exposed to excess radiation rays during serial capturing operations, as described in Example 44, the radiation emitting apparatus 3 of the radiographic image capturing system 100 according to Example 47 can independently determine still-image capturing conditions and serial-image capturing conditions.

Figure 38:
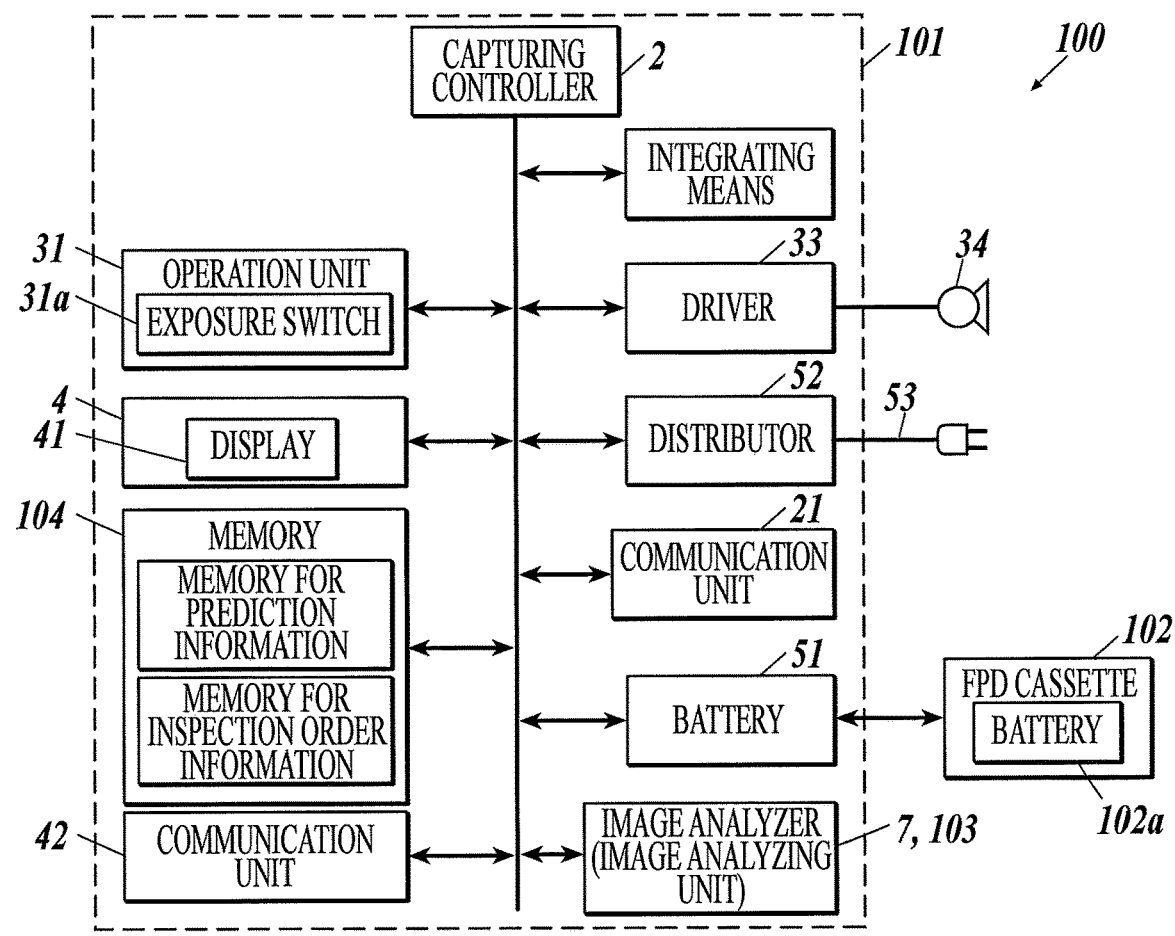
FIG. 38 is a block diagram illustrating a configuration of a radiographic image capturing system according to Example 47 of the first to third embodiments.

The radiographic image capturing system 100 according to Example 47 includes an integrating means for accumulating the dose of pulsed radiation rays emitted to a subject, as shown in FIG. 38.

The integrating means enables the product mAs×msec for all the pulses emitted to the subject to be determined and the overall exposure radiation dose to be estimated.

Alternatively, the calculation in Example 47 may be carried out by the multiplication of mAs×msec of the last pulse of radiation rays in the capturing operations by the total number of captured frames.

This enables the dose of radiation emitted (mAs) to be calculated by multiplying mAs×msec of the last pulse by the total number of captured frames.

<Preview>

Example 48

If the user determines that the dynamic image captured during a round is unsuitable for diagnosis, re-capturing operations are needed.

Unfortunately, the process of a dynamic image captured during a round at the console 4 in the medical cart 101 takes much time because the console 4 has a limited image processing capacity. This may force the subject in a capturing mode to wait until the user determines whether the dynamic image is suitable for diagnosis.

The console 4 of the radiographic image capturing system 100 according to Example 48 can divide dynamic image data received from the FPD 102 into frame image data.

The console 4 can also decimate partial frame image data of the dynamic image data generated at the FPD 102 to generate decimated dynamic image data with a reduced data volume.

The console 4 can also process the decimated dynamic image data to generate processed image data.

Figure 39:
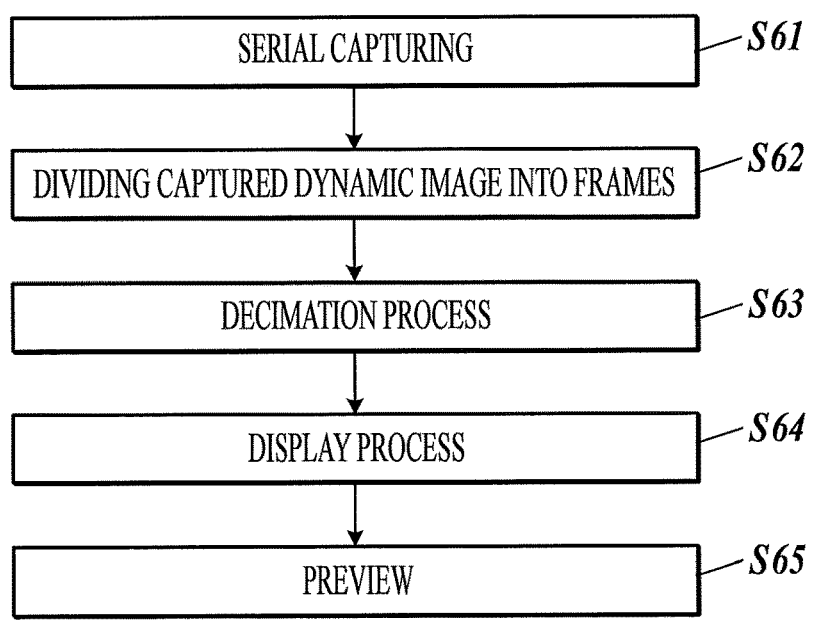
FIG. 39 is a flow chart of a control process of a radiographic image capturing system according to Example 48 of the first to third embodiments.

With reference to FIG. 39, the FPD 102 having these functions in the radiographic image capturing system 100 according to Example 48 performs serial capturing operations (Step S61) and then the console 4 divides a dynamic image into frames (Step S62). If independent frame images are sent from the FPD 102, the division process is unnecessary.

The console 4 performs the decimation process to decimate partial frame images (Step S63). For example, the decimation of frame images every two frames generates a group of frame images with a half number of frame images.

The decimated frame images are subject to a display process to re-organize multiple pieces of frame image data into dynamic image data (Step S64). The dynamic image re-organized based on the dynamic image data is previewed on the display 41 (Step S65).

This allows the user to verify the simplified dynamic image even with a console having a limited processing capability and determine the necessity for re-capturing operations promptly even at a round destination.

The dynamic image based on the image data acquired through the process of the decimated dynamic image data has a significant change between frame images. This helps persons other than medical experts who use the dynamic image for diagnosis determine the necessity for re-capturing operations.

Example 49

If the user determines that the dynamic image captured during a round is unsuitable for diagnosis, re-capturing operations are needed.

Unfortunately, the process of a dynamic image captured during a round at the console in the medical cart takes much time because the console has a limited image processing capacity. This may force the subject in a capturing mode to wait until the user determines whether the dynamic image is suitable for diagnosis.

The console 4 in the radiographic image capturing system 100 according to Example 49 can also decimate partial frame image data of dynamic image data to generate decimated dynamic image data with a reduced data volume.

The console 4 can also process the decimated dynamic image data to generate processed image data and display the dynamic images based on the processed image data on the display 41.

If a dynamic image is displayed at a round destination, then the console 4 decimates the frame images and processes the decimated frame images; otherwise, the console 4 processes the original image data without decimation.

Figure 40:
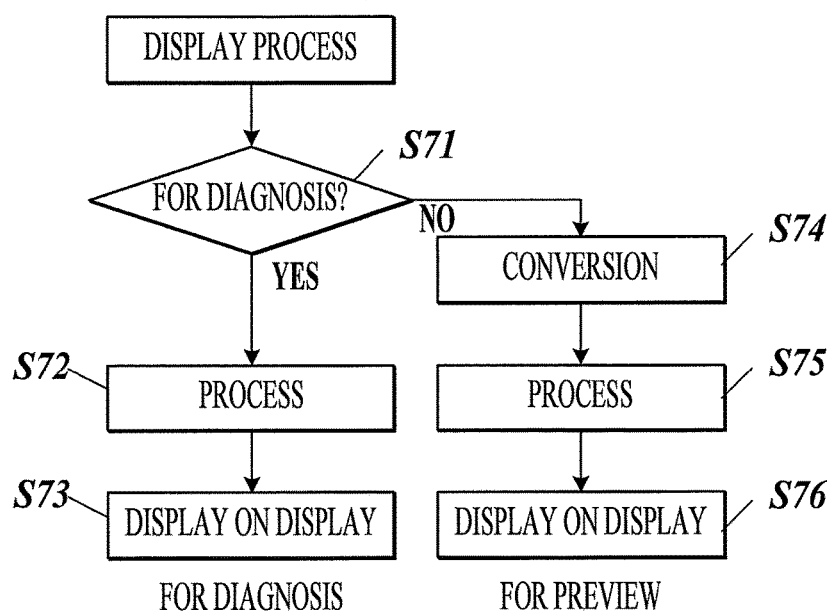
FIG. 40 is a flow chart of a control process of a radiographic image capturing system according to Example 49 of the first to third embodiments.

With reference to FIG. 40, the console 4 having these functions in the radiographic image capturing system 100 according to Example 49 determines whether an instruction to perform image processing for diagnosis has been received (Step S71). If the instruction is image processing for diagnosis (Step S71: Yes), the console 4 processes all the frame images in the dynamic image data (Step S72) and displays the processed image data on the display 41 (Step S73).

If the instruction is not image processing for diagnosis but for preview at Step S71 (Step S71: No), the console 4 decimates the frames of the dynamic image (Step S74), processes the decimated dynamic image data (Step S75), and displays the image of the processed data on the display 41 (Step S76).

This allows the user to verify the simplified dynamic image even with a console having a limited processing capability and determine the necessity for re-capturing operations promptly even at a round destination.

The dynamic image based on the image data acquired through the process of the decimated dynamic image data has a significant change between frame images. This helps persons other than medical experts who use the dynamic image for diagnosis determine the necessity for re-capturing operations.

Example 50

The user needs to determine whether a dynamic image captured during a round is suitable for diagnosis and perform re-capturing operations if the captured dynamic image is determined to be unstable for diagnosis.

In addition, the user needs to verify the dynamic image in parallel with capturing operations to check whether the subject respires at a timing specified during the capturing operations and the motion of the subject does not adversely affect the capturing operation.

Furthermore, the user carries out preparatory settings of the system and preliminarily confirms the capturing operations. Immediately after the start of a capturing operation, the user needs to check the radiation emitting apparatus for a proper emission of radiation rays and the subject for proper positioning. This precludes the confirmation of the quality of a dynamic image immediately after the start of a capturing operation.

Figure 41:
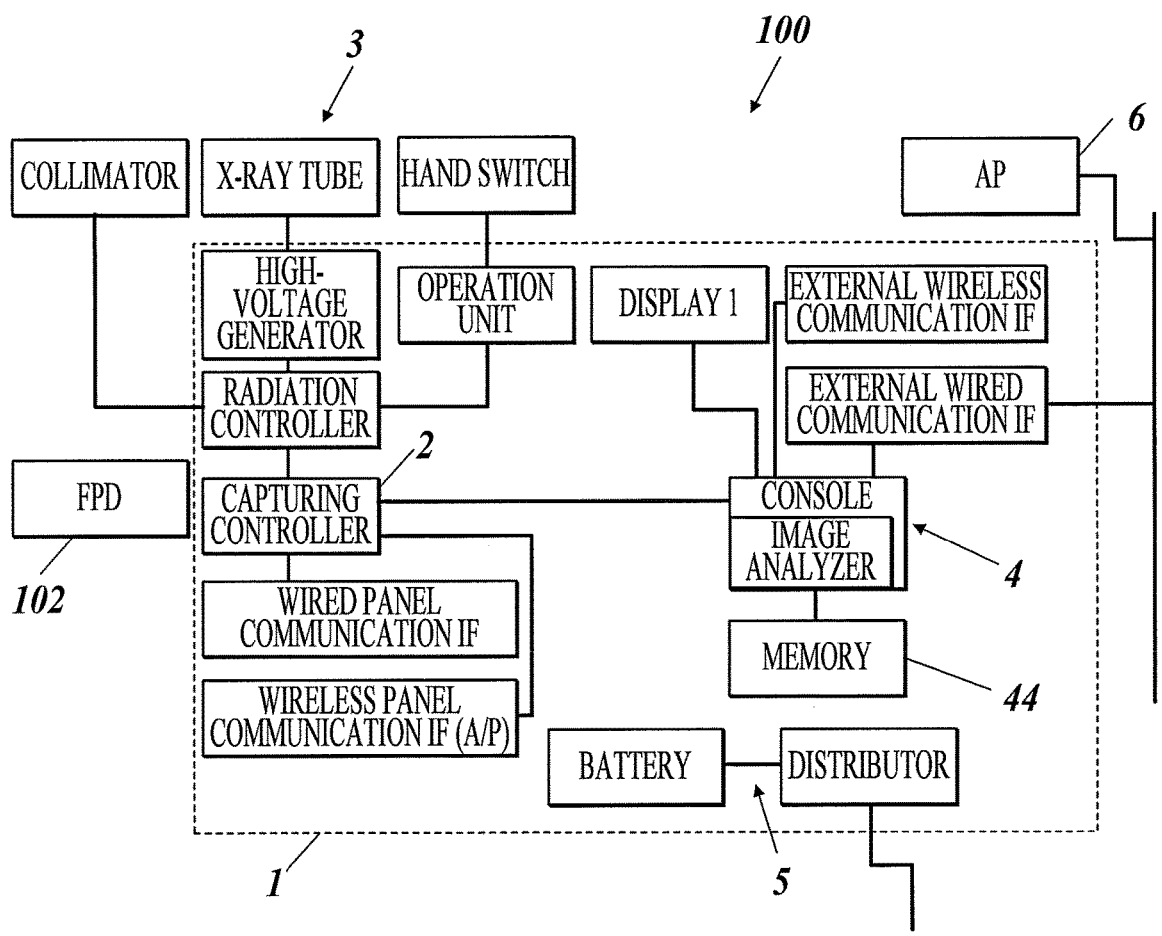
FIG. 41 is a block diagram illustrating a configuration of a radiographic image capturing system according to Example 50 of the first to third embodiments.

To cope with this problem, the console 4 in the radiographic image capturing system 100 according to Example 50 includes a memory 44 for storing image data, as shown in FIG. 41.

The console 4 stores each frame image of a dynamic image transferred from the capturing controller 2 in the memory 44.

The console 4 has a function to display each frame image stored in the memory 44 on the display 41 after the elapse of a predetermined delay time from the time of receiving the frame image from the capturing controller 2.

This enables the user to verify the dynamic image throughout the capturing period by delaying the display by a predetermined time from the capturing even if the user cannot verify the captured dynamic image immediately after the start of the capturing operation because of other work.

Example 51

During the capturing operations with the radiographic image capturing system according to Example 50, the user verifies the dynamic image after a delay time. Since the last capturing operation also has such a delay time, the subject must wait for verification of the dynamic image.

Since a subject with a disease or an elderly person may collapse after the capturing operations, the user has to pay attention to such a subject during the verification of a captured image, placing a heavy burden on the user.

The console 4 of the radiographic image capturing system 100 according to Example 51 includes a memory 44 similar to that of Example 50.

Similar to Example 50, the console 4 can display each frame image stored in the memory 44 on the display 41 after the elapse of a predetermined delay time from the time of receiving the frame image from the capturing controller 2.

The console 4 can reduce the number of frames γ calculated with Expression (2) of the frame images stored in the memory 44 by decimation and display the remaining frame image after the elapse of a predetermined delay time from the time of receiving the frame image from the capturing controller 2.

The number of decimated frames γ=(Total capturing time−Delay time)/Total capturing time (2)

If the result of the decimation in the dynamic image is too rough to deserve verification, the number of decimated frames γ is calculated with Expression (3) to reduce the number of decimated frames:

$$\gamma=(\text{Total capturing time}-\text{Delay time}+\alpha)/\text{Total capturing time} \quad (3)$$

Figure 42:
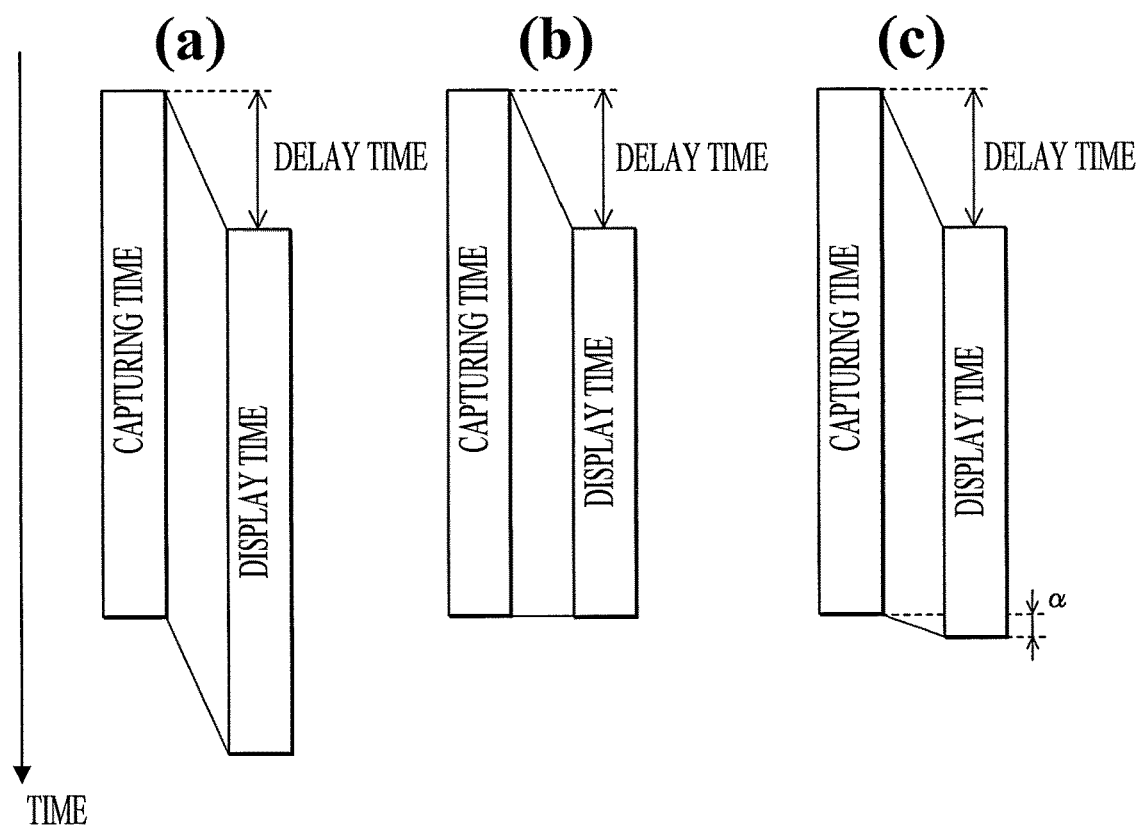
FIG. 42 is a conceptual diagram illustrating the operations of a radiographic image capturing system according to Example 51 of the first to third embodiments.

This delays in displaying a dynamic image from the start of a capturing operation, as shown in FIG. 42, to enable the user to start verification of the dynamic image after completion of the task that must be performed immediately after the start of capturing operations.

The decimation of frames reduces the time to display the dynamic image to less than the capturing time, completing the display of the dynamic image concurrently with the completion of the capturing operation. This can eliminate or shorten the waiting time of the subject.

Example 52

If the user determines that the dynamic image captured during a round is unsuitable for diagnosis, re-capturing operations are needed.

Unfortunately, the process of a dynamic image captured during a round at the console in the medical cart takes much time because the console has a limited image processing capacity. This may force the subject in a capturing mode to wait until the user determines whether the dynamic image is suitable for diagnosis.

Figure 43:
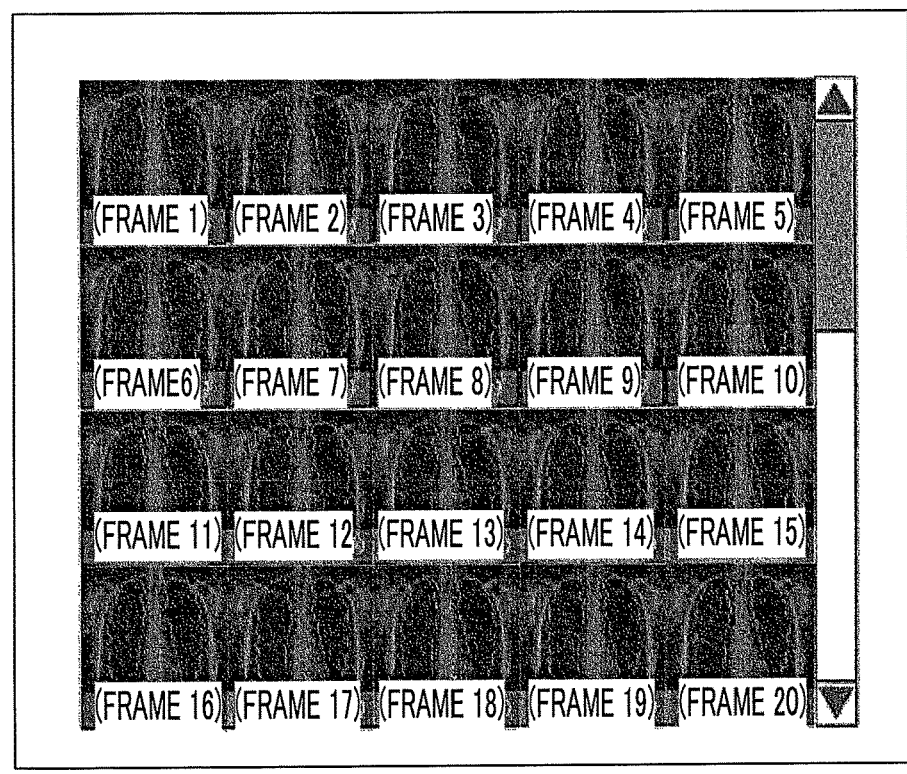
FIG. 43 illustrates an exemplary display on a display of a radiographic image capturing system according to Example 52 of the first to third embodiments.

To cope with this problem, the console 4 of the radiographic image capturing system 100 according to Example 52 displays the frame images of a dynamic image in succession side by side on the display 41, as shown in FIG. 43.

If all the frame images cannot be displayed on the display 41, the user may scroll the screen with the mouse wheel to change frame images displayed.

This allows the user to view frames in succession, check whether any body motion of the subject has adversely affected the capturing operation, and readily determine the necessity for a re-capturing operation.

This allows the user to verify the entire dynamic image more promptly than the verification during play-back, which takes the same time as the capturing operation.

Example 53

If the user determines that the dynamic image captured during a round is unsuitable for diagnosis, re-capturing operations are needed.

Unfortunately, the process of a dynamic image captured during a round at the console in the medical cart takes much time because the console has a limited image processing capacity. This may force the subject in a capturing mode to wait until the user determines whether the dynamic image is suitable for diagnosis.

Figure 44A:
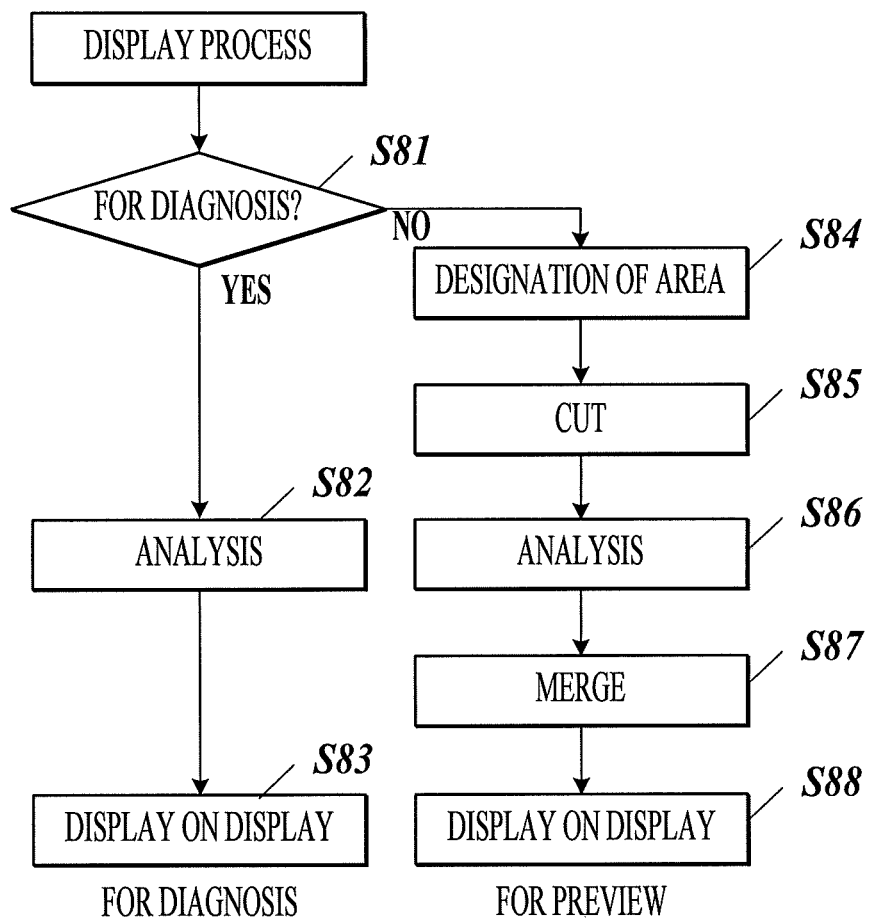
FIG. 44A is a flow chart of a control process of a radiographic image capturing system according to Example 53 of the first to third embodiments.

To cope with this problem, in the case of serial capturing operations for diagnosis (Step S81: Yes), the radiographic image capturing system 100 according to Example 53 analyzes a captured dynamic image (Step S81) to generate a dynamic image and displays the dynamic image in a display process (Step S82), as shown in FIG. 44A.

Figure 44B:
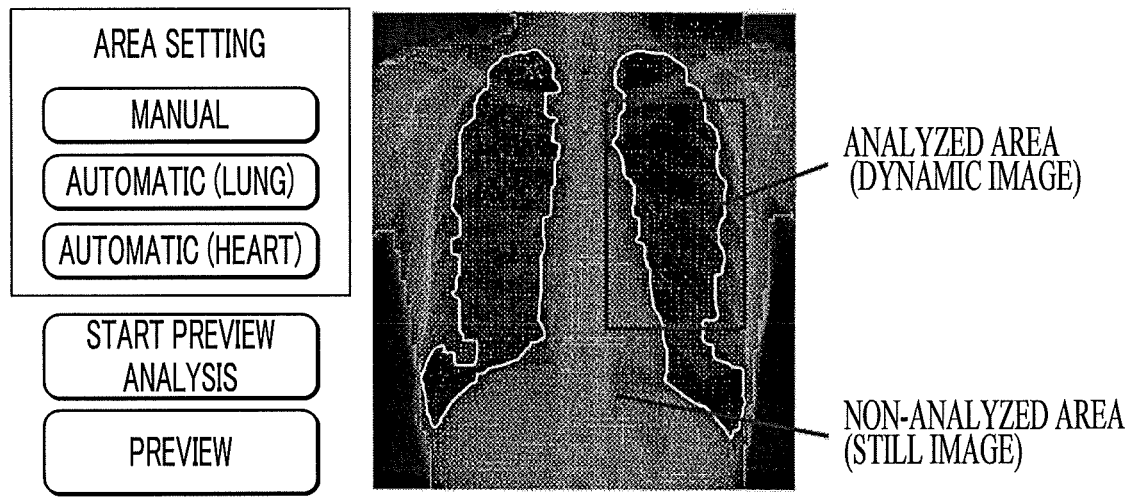
FIG. 44B illustrates an exemplary display on a display of the radiographic image capturing system according to Example 53 of the first to third embodiments.

In the case of serial capturing operations for preview to determine whether the dynamic image is suitable for diagnosis during rounds (Step S81; No), an operation screen as shown in FIG. 44B is displayed to allow the user to specify part of the dynamic image as an area to be analyzed (Step S84), the specified area is cut (Step S85), analysis is performed only on the cut area (Step S86), and the processed area is merged with a non-analyzed area (Step S87) to display the merged image on the display 41 in a display process (Step S88).

The non-analyzed area to be merged may be the first frame of the dynamic image or each frame of the dynamic image.

The area to be analyzed in the captured image may be determined by specifying a rectangular area with mouse or touch panel operations or reading an area predetermined for each target site.

This can narrow the analytical area to reduce the analytical time.

This allows the user to verify a simply-analyzed dynamic images even with a processor having a limited image processing capacity and determine the necessity for re-capturing operations at a capturing site.

Example 54

If the user determines that the dynamic image captured during a round is unsuitable for diagnosis, re-capturing operations are needed.

Unfortunately, the process of a dynamic image captured during a round at the console 4 in the medical cart 101 takes much time because the console 4 has a limited image processing capacity. This may force the subject in a capturing mode to wait until the user determines whether the dynamic image is suitable for diagnosis.

The console 4 of the radiographic image capturing system 100 according to Example 54 can divide dynamic image data received from the FPD 102 into frame image data.

The console 4 also can decimate partial frame image data of multiple pieces of frame image data at predetermined intervals.

The console 4 also can insert black or white frames in spaces between left frame images, i.e., spaces generated by decimating frame images.

The console 4 also has a display function to reorganize the frame images that are subject to the insertion process into a dynamic image and displays the reorganized dynamic image on the display 41.

Figure 45:
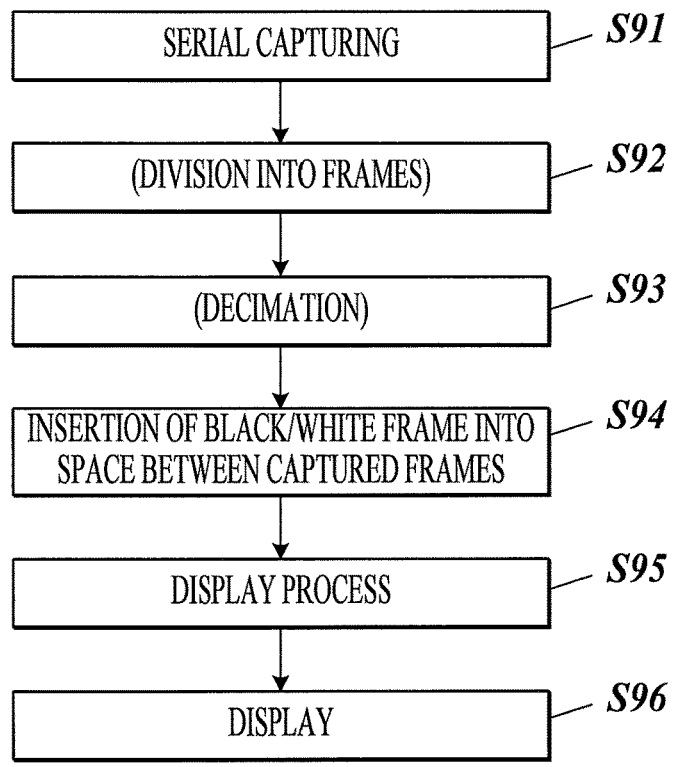
FIG. 45 is a flow chart of a control process of a radiographic image capturing system according to Example 54 of the first to third embodiments.

With reference to FIG. 45, the FPD 102 having the above-mentioned functions in the radiographic image capturing system 100 according to Example 54 provided with the console 4 performs serial capturing operations (Step S91) and then the console 4 divides a dynamic image into frames (Step S92). If independent frame images are sent from the FPD 102, the division process is unnecessary.

The console 4 decimates the frame images (Step S93). For example, the decimation of frame images every two frames generates a half number of frame images.

The console 4 performs the insertion process to insert black frame images (Step S94). As described above, the decimation of frame images every two frames results in the original frame images and the black frame images being disposed alternatively to produce a dynamic image consisting of frame images having the same total number of frames (or the same play-back time) as that of the original dynamic image.

The console 4 performs the display process on the frame images subject to the insertion process to reorganize the multiple pieces of frame image data into dynamic image data (Step S95) and display a dynamic image based on the dynamic image data on the display 41 (Step S96).

A continuous view of consecutive dynamic images or frames causes indiscernible differences between frames and precludes determination of a dynamic image suitable for diagnosis. However, the insertion of black or white frame images between these frames at predetermined intervals facilitates determination of the quality of each frame image without comparison with the quality of the previous frame, preventing wrong judgement.

Example 55

The time length available for capturing a dynamic image is determined by the remaining capacity of the memories in the FPD 102 and in the medical cart. Unfortunately, the user does not know how much longer the capturing operation can be performed in the current capturing mode, resulting in suspension of the capturing operation due to shortage of the memory capacity in the FPD 102 or in the medical cart 101.

To cope with this problem, the memory in the medical cart 101 or the console 4 of the radiographic image capturing system 100 according to Example 55 stores the memory capacities in the FPD 102 and in the medical cart required for each capturing mode.

The capturing controller 2 or the console 4 of the medical cart 101 has a capacity acquiring means for acquiring the memory capacities in the FPD 102 and in the medical cart before capturing operations.

The capturing controller 2 or the console 4 of the medical cart 101 has a calculating means for calculating the remaining time length available for capturing, the number of capturable dynamic images, or the number of capturable still images based on the memory capacities available in the FPD 102 and in the medical cart and the memory capacities in the FPD 102 and in the medical cart required for a selected capturing mode.

The capturing controller 2 or the console 4 of the medical cart 101 has a displaying means for displaying the calculated remaining time length available for capturing, the calculated number of capturable dynamic images, or the calculated number of capturable still images on the display 41.

The remaining time length available for capturing, the number of capturable dynamic images, or the number of capturable still images may be displayed for two or more capturing modes.

This configuration allows the user to preliminarily know the remaining time length available for capturing, the number of capturable dynamic images, or the number of capturable still images based on a capturing mode. This eliminates the risk of a capturing failure due to shortage of the memory capacity in the FPD 102 or in the medical cart after the start of capturing. This also helps the user plan the order of capturing operations on a subject and capturing modes used.

<Cine Playback>

Example 56

If the user determines that the dynamic image captured during a round is unsuitable for diagnosis, re-capturing operations are needed.

Unfortunately, the process of a dynamic image captured during a round at the console in the medical cart takes much time because the console has a limited image processing capacity. This may force the subject in a capturing mode to wait until the user determines whether the dynamic image is suitable for diagnosis.

Figure 46:
FIG. 46 illustrates an exemplary display on a display of a radiographic image capturing system according to Example 56 of the first to third embodiments.

To cope with this problem, the radiographic image capturing system 100 according to Example 56 enables the user to display multiple dynamic images side by side on the display 41 of the console 4 after serial capturing operations, as shown in FIG. 46.

Each dynamic image is acquired by dividing dynamic images into groups by capturing time. In other words, multiple dynamic images captured at different times can be played back in parallel. With reference to FIG. 46, dynamic images captured over 20 seconds are divided into four groups of dynamic images at time intervals of 5 seconds (the four groups started capturing at second 0, second 5, second 10 and second 15, respectively) and the four groups are displayed side by side. The concurrent play-back of these dynamic images, which were captured over 20 seconds, enables verification of these images in five seconds.

This enables the user to view more images at one time than the conventional playback, facilitating finding of an inappropriate image.

Captured images are divided into several groups and the groups of dynamic images are verified in parallel. This enables verification of all the captured images in a shorter time than the actual capturing duration.

<Other Examples>

Example 57

The battery 102*a* in the FPD 102 has a predetermined capacity and the FPD 102 cannot be connected to an electric outlet during the capturing operation at a round destination. A user should pay attention to the battery level during the capturing operation to prevent the FPD 102 from being inoperative during rounds due to running out of battery.

The FPD 102 in the radiographic image capturing system 100 according to Example 57 monitors the state of its own power supply while the power switch is on. If the FPD 102 is not connected with an external power source via a power cable and receives power from its own battery, the FPD 102 operates in the power-saving mode. If the FPD 102 receives power from the medical cart 101 via a power cable, the FPD 102 operates in a normal power consumption mode.

This configuration reduces the power consumption of the battery in the FPD 102, reducing the number of charging operations of the battery in the FPD 102 or shortening the charging duration.

Example 58

In serial capturing operations, a subject is requested to respire at a certain timing under the instructions of the user. The user must issue an instruction on the timing of respiration to the subject. Such instructions may be directly issued by the user orally, but are given by an automated voice in many cases since the user is often busy with capturing operations. Alternatively, such instructions may be given on an instruction screen on a display by switching lights.

Unfortunately, instructions by the automated voice or on the display unsuitable for a target site or a capturing scheme results in an instruction issued to the subject at a wrong timing, causing a capturing failure.

The controller of the console 4 of the radiographic image capturing system 100 according to Example 58 acquires the content of a voice instruction to the subject, the timing of playback of the voice instruction, or the timing of display in response to a capturing order (information containing a target site and a capturing scheme) received from RIS.

The acquisition of the content of an instruction and the timing of playback may be performed by retrieving them from a list of the types of voice instruction and the timing of playback stored in, for example, the memory of the console 4 or by referencing a look-up table.

This configuration ensures that instructions by an automated voice or on the display and the timing of instruction that are suitable for a target site and a user-selected capturing scheme are automatically selected. This configuration also ensures that an appropriate instruction is issued to the subject at a right timing.

Example 59

Independent wiring from the radiation controller 72 in the radiation emitting apparatus 3 to various units in the radiation emitting apparatus 3 (the operation unit 31, the high-voltage generator 33, and the collimator 35) requires a large number of cables. This precludes design or manufacture (installation of wiring) of the radiation emitting apparatus 3.

In addition, changes to the operation unit 31, the high-voltage generator 33, and the collimator 35 also require changes to wiring, which precludes changes to these units.

Figure 47:
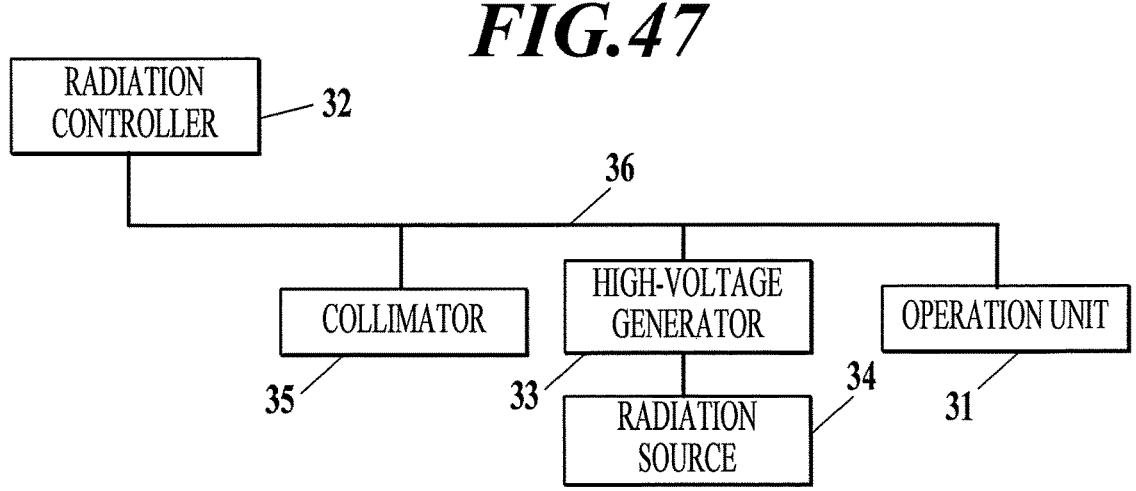
FIG. 47 is a block diagram illustrating a configuration of a radiographic image capturing system according to Example 59 of the first to third embodiments.

To cope with this problem, the radiation emitting apparatus 3 according to Example 59 has the radiation controller 32, the operation unit 31, the high-voltage generator 33, and the collimator 35 connected to a single communication path 36, as shown in FIG. 47. A communication scheme, such as CAN. CANopen, and DeviceNet, can be used for the communication path.

This configuration can simplify wired connections in the radiation emitting apparatus 3, facilitating the designing, manufacture, and modifications of the radiation emitting apparatus 3.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2017-122570 filed on Jun. 22, 2017 is incorporated herein by reference in its entirety.

What is claimed is:

1. A medical cart which obtains dynamic image data including a plurality of sets of frame image data, the medical cart comprising:
   a hardware processor which generates the dynamic image data, and which performs a decimating processing in which some of the frame image data is decimated from the generated dynamic image data; and
   a display which displays a dynamic image based on the decimated dynamic image data wherein the decimating processing is performed based on a result of a determination identifying when a diagnosis is performed.

2. The medical cart according to claim 1, wherein, the decimating processing is performed based on a result of a determination identifying a destination for sending data.

3. The medical cart according to claim 1, wherein, the hardware processor performs an image processing
   on the decimated dynamic image and generates processed image data, and
   the display displays the dynamic image based on the processed image data.

4. The medical cart according to claim 1, wherein, the hardware processor performs an image processing automatically or based on a predetermined operation by the user.

5. The medical cart according to claim 1, wherein, the hardware processor is configured to receive an instruction to perform an image processing for diagnosis, and perform the image processing on the generated dynamic image data.

6. The medical cart according to claim 1, wherein, the hardware processor is configured to determine that an instruction to perform the image processing for diagnosis is not received, and perform an image processing on the decimated dynamic image data.

7. The medical cart according to claim 1, wherein the hardware processor decimates the generated dynamic image data to make the frame image data half or less.

8. The medical cart of claim 1, wherein:
   the decimating process is not performed when the determination determines that the diagnosis is being performed, and
   the decimating process is performed when the determination determines that the diagnosis is not being performed.

9. The medical cart of claim 1, wherein the decimating processing occurs in response to at least one of:
   a determination that image data can be sent and received to an image analyzing unit via a wireless network, and
   a determination that image data is to be displayed as a preview or for verification.

10. A method which obtains dynamic image data including a plurality of frame image data, the method comprising:
    generating the dynamic image data;
    performing a decimating processing in which some of the frame image data is decimated from the generated dynamic image data; and
    displaying a dynamic image based on the decimated dynamic image data,
    wherein the decimating processing is performed based on a result of a determination identifying when a diagnosis is performed.

11. A non-transitory computer-readable storage medium storing a program which obtains dynamic image data including a plurality of frame image data, the program causing a computer to perform:
    generating the dynamic image data;
    performing a decimating processing in which some of the frame image data is decimated from the generated dynamic image data; and
    displaying a dynamic image based on the decimated dynamic image data,
    wherein the decimating processing is performed based on a result of a determination identifying when a diagnosis is performed.

* * * * *